United States Patent [19]

Harnisch

[11] Patent Number: 4,919,848
[45] Date of Patent: Apr. 24, 1990

[54] PROCESS FOR THE QUENCHING OF FLUORESCENCE, AND NEW CATIONIC NAPHTHALENE-PERI-DICARBOXYLIC ACID IMIDE DERIVATIVES

[75] Inventor: Horst Harnisch, Much, Fed. Rep. of Germany

[73] Assignee: Bayer Aktiengesellschaft, Leverkusen, Fed. Rep. of Germany

[21] Appl. No.: 913,888

[22] Filed: Sep. 30, 1986

[30] Foreign Application Priority Data

Oct. 4, 1985 [DE] Fed. Rep. of Germany ....... 3535496

[51] Int. Cl.$^5$ .......................... G03C 1/00; D06L 3/00
[52] U.S. Cl. ........................................ 252/600; 8/102; 8/568; 8/586; 8/606; 162/110; 162/158; 162/162; 250/483.1; 250/487.1; 250/488.1; 546/99
[58] Field of Search ..................... 252/600; 8/102, 568, 8/586, 606; 162/110, 158, 162; 250/483.1, 487.1, 488.1; 546/99

[56] References Cited

U.S. PATENT DOCUMENTS

| | | | |
|---|---|---|---|
| 3,639,642 | 2/1972 | Matter et al. | 162/158 |
| 3,804,838 | 4/1974 | Mirgasson et al. | 546/99 |
| 3,849,331 | 11/1974 | Mingasson et al. | 546/99 |
| 3,898,234 | 8/1975 | Burdeska et al. | 546/99 |
| 3,953,451 | 4/1976 | Hell et al. | 546/99 |
| 4,098,954 | 7/1978 | Raspanti | 162/158 |
| 4,139,532 | 2/1979 | Scheuermann | 540/99 |
| 4,220,777 | 9/1980 | Karg | 546/99 |
| 4,384,121 | 5/1983 | Meyer | 546/99 |
| 4,508,900 | 4/1985 | Schönberger et al. | 546/99 |
| 4,695,405 | 9/1987 | Harnisch | 8/102 X |

FOREIGN PATENT DOCUMENTS

| | | |
|---|---|---|
| 0028777 | 5/1981 | European Pat. Off. . |
| 3618458 | 12/1987 | Fed. Rep. of Germany . |
| 2172402 | 11/1973 | France .................................. 546/99 |
| 1221888 | 2/1971 | United Kingdom . |
| 1342350 | 1/1974 | United Kingdom . |

OTHER PUBLICATIONS

Tsukahara, "Ability of Spectral Sensitization and Quenching...", Bull. Soc. Scient. Photog. Jap. No. 19, 12/1969, p. 11.

FARH F06 384 89 D/22=J5 6076-459 Quat. Amino-Neopentyl Naphthalimide Salts-Used as Optical Whitener, esp. for Polyacrylonitrile HOECHST AG 07.11.79-DE-944867 A60 E23 (24.06.81) *EP-2-8-777 06.11.80 as 155253.

Primary Examiner—Mary C. Lee
Assistant Examiner—Catherine S. Kilby Scalzo
Attorney, Agent, or Firm—Sprung Horn Kramer & Woods

[57] ABSTRACT

To quench the fluorescence generated by anionic optical brighteners, virtually colourless, water-soluble, cationic compounds are used which contain at least one cationic group per molecule or per repeating structural unit and at least two nitro group-free naphthalene-peridicarboxylic acid imide groups per molecule or at least one such group per repeating structural unit.

5 Claims, No Drawings

PROCESS FOR THE QUENCHING OF FLUORESCENCE, AND NEW CATIONIC NAPHTHALENE-PERI-DICARBOXYLIC ACID IMIDE DERIVATIVES

The invention relates to a process for the quenching of the fluorescence generated by anionic optical brighteners by the action of virtually colourless, water-soluble, cationic compounds which contain at least one cationic group per molecule or per repeating structural unit and at least two nitro group-free naphthalene-peridicarboxylic acid imide groups per molecule or at least one such group per repeating structural unit.

Preferred compounds contain one to four cationic groups per molecule or one or two such groups per repeating structural unit and two to six, preferably two to four, peri-dicarboxylic acid imide groups per molecule or one to four, preferably two to four, such groups per repeating structural unit.

The groups mentioned are preferably linked to one another via bridging members. As cationic groups, acyclic and cyclic ammonium groups and acyclic and cyclic sulphonium groups may be particularly mentioned. These can be bonded terminally to the molecule or represent a bridging member.

Particularly preferred compounds are totally free of nitro groups.

The water-soluble, cationic compounds preferably have the general formula

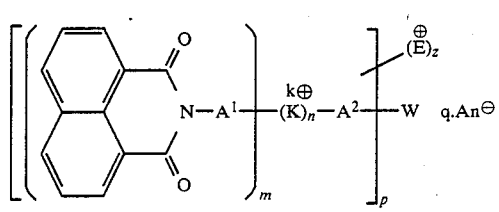

in which
$A^1$, $A^2$ and W represent a bridging member or a single bond,
W also represents hydrogen,
$E^\oplus$ represents a terminal ammonium or sulphonium group
$K^\oplus$ represents a doubly bridging ammonium or sulphonium group,
$An^\ominus$ represents an anion,
m and k represent 1 or 2,
z represents 0, 1, 2, 3 or 4,
n represents 0 or 1 and
p represents 1, 2 or 3,
q corresponds to the sum of the free cationic charges, where $n+z \neq 0$,
in which the naphthalene ring system can also be substituted in the second peri-position by $-CH_2-CH_2-$, $-CO-O-CO-$ or $-CO-NH-CO-$, the naphthalene ring system, $A^1$, $A^2$, W, $-E^\oplus$ and $-K^\oplus-$ and the second peri-dicarboxylic acid imide nitrogen atom can be substituted by non-ionic radicals, and the total structure specified can also be the repeating unit of a high molecular weight compound.

Cyclic ammonium and sulphonium groups are understood to be $N^\oplus$- or $S^\oplus$-containing rings or ring systems as a whole. These can be saturated, partly saturated or pseudoaromatic, saturated and pseudoaromatic being preferred.

Suitable ammonium and sulphonium groups are, for example:

(a) terminal groups $-E^{1\oplus}$:

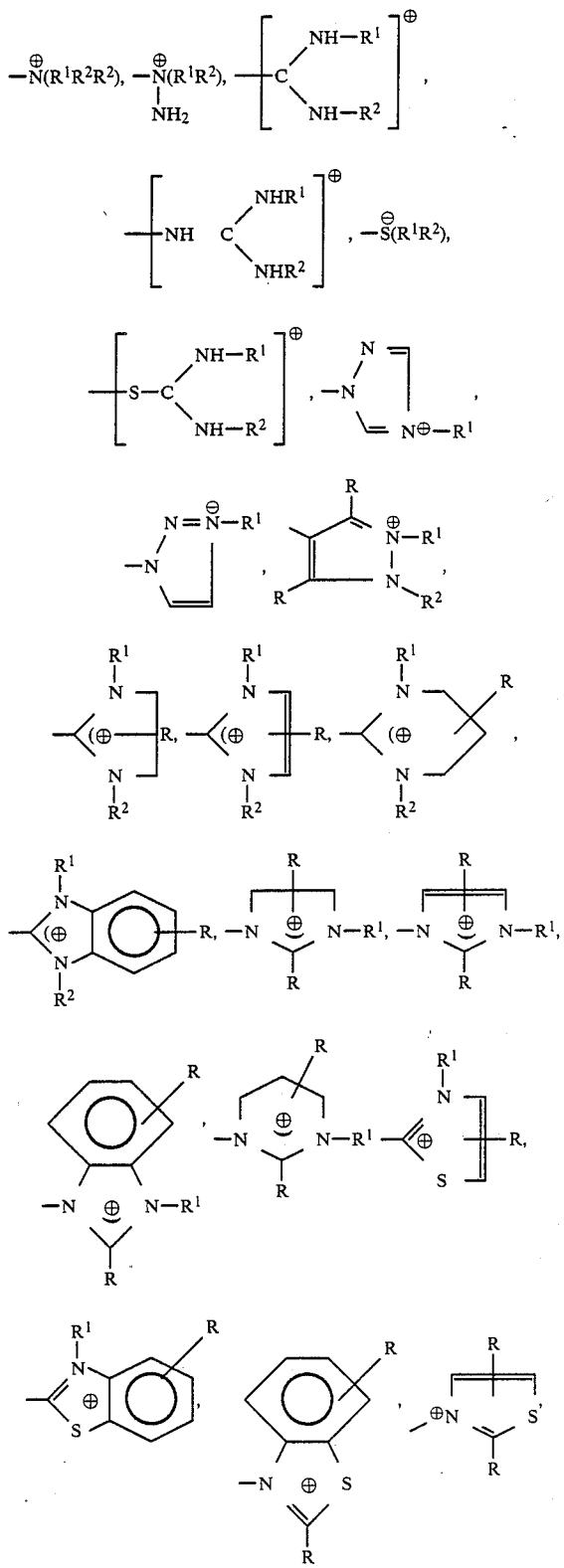

-continued

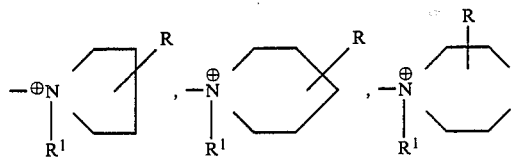
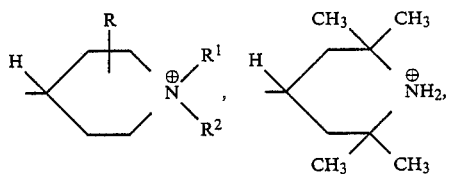
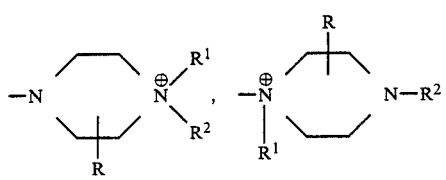
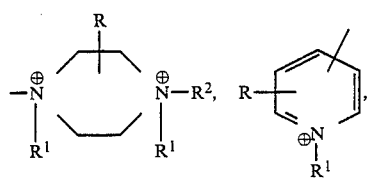
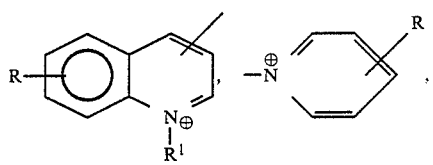
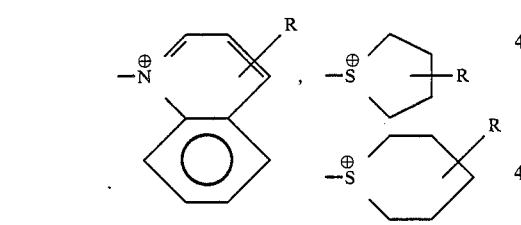

(b) bridging members

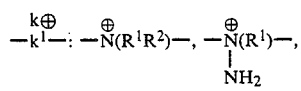
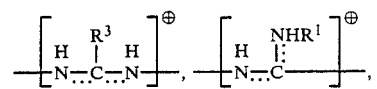
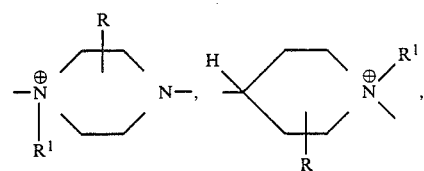

-continued

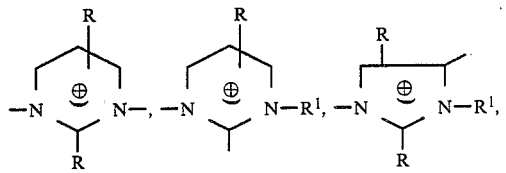
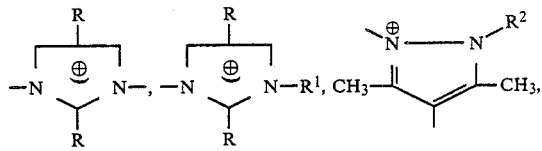
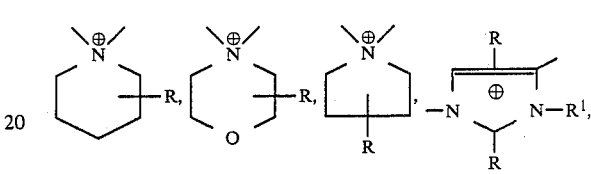
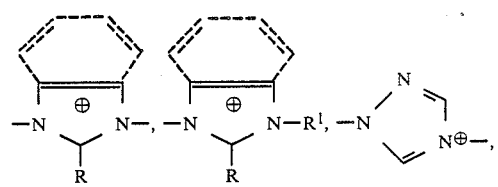
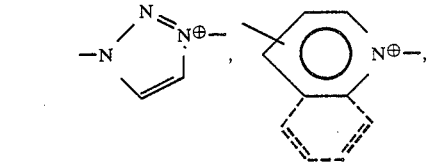
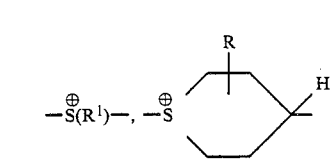
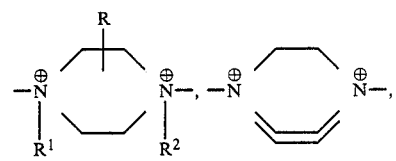
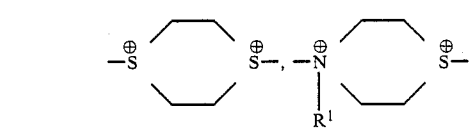

In the formulae:
R denotes hydrogen or 1 to 4 methyl groups,
$R^1$ and $R^2$ denote hydrogen, $C_1$–$C_4$-alkyl, which can be substituted by OH, $NH_2$, $C_1$–$C_4$-alkoxy, halogen, $CONH_2$, CN, COOH, $C_1$–$C_4$-alkoxycarbonyl or $C_1$–$C_4$-alkylcarbonyl, $C_2$–$C_4$-alkenyl, phenyl$C_1$–$C_3$-alkyl, phenylaminocarbonylmethyl, benzoylmethyl or benzimidazolyl-(2)-methyl, each of which can be substituted in the nucleus by nitro, cyano, $C_1$–$C_4$-alkyl, $C_1$–$C_4$-alkoxy, chlorine or bromine, $R^2$ denotes, in addition, cyclohexyl or phenyl, which can be substituted by nitro, $C_1$-$C_4$-alkyl, $C_1$-$C_4$-alkoxy, chlorine or bromine, and $R^3$ denotes hydrogen, $C_1$-$C_4$-alkyl, SH or $NH_2$.

Preferred acylic ammonium groups correspond to the formulae $-N^{\oplus}(R^1R^2R^2)$ and $-N^{\oplus}(R^1R^2)-$, particularly $-N^{\oplus}(CH_3)_2-R^1$ and $-N^{\oplus}(CH_3)_2-$.

Preferred cyclic ammonium groups are piperazinium, piperidinium, morpholinium, pyrrolidinium, imidazolium, pyrazolium and pyridinium radicals. The piperazinium and pyridinium groups are of special significance.

Suitable anions $An^{\ominus}$ are the usual colourless inorganic or organic water-soluble solubilizing anions such as chloride, bromide, iodide, chlorozincate, tetrafluoroborate, sulphate, hydrogen sulphate, methosulphate, ethosulphate, benzenesulphonate, p-toluenesulphonate, methylsulphonate, amidosulphonate, nitrate, hydrogen phosphate, methylphosphonate, methylphosphonate monomethyl ester, acetate, lactate, formate, maleate, succinate, citrate, tartrate and oxalate.

Examples of anionic substituents are the carboxylic acid and sulphonic acid groups.

Examples of non-ionic substituents which may be mentioned in the context of compound (I) are: halogen, such as chlorine and bromine, hydroxy, cyano, alkyl, alkoxy, aralkoxy, aryloxy, cyclohexyloxy, alkylcarbonyloxy, aroyloxy, arylaminocarbonyl, alkoxycarbonyl, alkylcarbonyl, alkylsulphonyl, arylsulphonyl, optionally mono- or dialkylated or closed-ring carbamoyl or sulphamoyl, and in addition as substituents for rings alkyl, aralkyl and aryl and (apart from for II and III) also nitro.

Generally, in the context of the invention, alkyl is preferably understood as being a radical with 1 to 4 C atoms, alkenyl as being allyl or methallyl, aryl as being phenyl or naphthyl and aralkyl as being phenyl-$C_1$-$C_3$-alkyl.

Suitable nitro group-free peri-dicarboxylic acid imide radicals belong to the naphthalimide series (formula II) or the naphthalene-1,4,5,8-tetracarboxylic acid diimide series (formula III):

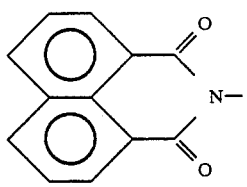

II

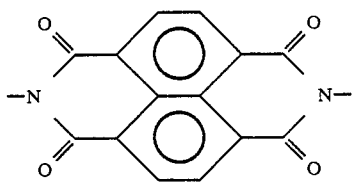

III

The carbon atoms of (II) and (III) can be substituted by non-ionic, anionic or cationic radicals.

The imide nitrogen atoms of (II) and (III), particularly one of the imide nitrogen atoms of (III), can also carry non-ionic substituents, for example alkyl, alkenyl, aralkyl, cycloalkyl, aryl and hetaryl radicals which are optionally bonded to the imide nitrogen atom via $-O-$ or $-N(R)-CO-$, where R represents H or $CH_3$. These radicals are preferably linked directly to the imide nitrogen atom. They can themselves be substituted by non-ionic, anionic or cationic radicals such as $-E^{1\oplus}$.

In (II), the substituents are preferably in the 3-, 4-, 5- and 6-positions.

Preferred substituents on (II) are chlorine, bromine and carboxy in the 4- and/or 5-position and the peri-carboxylic acid anhydride group. The unsubstituted naphthalimide radicals are of particular industrial significance.

Suitable bridging members $A^1$, $A^2$ and W, which connect the radicals (II) and/or (III) to one another or these groups with the ammonium and/or sulphonium radicals or which also link two of these cationic groups with one another, are those which are stable under conditions of application, that is to say for example are not hydrolysed in water. They are, as a rule, doubly or triply bridging and comprise one or more acyclic and/or cyclic nonchromophoric structural elements. Examples which may be mentioned are: optionally substituted $C_1$-$C_{10}$-alkylene, $-C_6H_4-CH_2-$, phenylene, naphthylene, anthracene, phenanthrene, dihydrophenanthrene, fluorenone, hetarylene and cyclohexylene radicals, 5- or 6-membered saturated heterocyclic rings, $-O-$, $-S-$, $-N(R)-$, $-N-$, $-CO-$, $-CS-$, $-SO_2-$, $-SO-$,

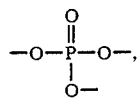

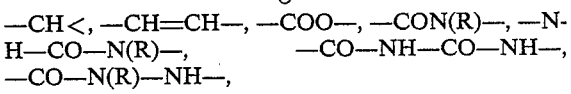

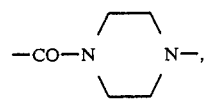

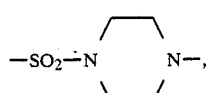

$-NH-CS-N(R)-$, in which R has the meaning specified above. The hydrocarbon radicals and heteroclenes mentioned can also form a common bridge together with 1 to 3 of the remaining bridging members.

Preferred bridging member $A^1$ between an amide nitrogen atom of (II) or (III) and an ammonium or sulphonium group is the bridging member $A^3$, which represents a single bond, 1,3- or 1,4-$C_6H_4-CH_2-$, -xylylene, -phenylene or -cyclohexylene, $C_1$-$C_{10}$-alkylene, which can be interrupted by $-O-$, $-CO-O-$, $-CO-N(R)-$ or

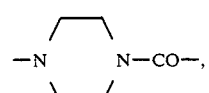

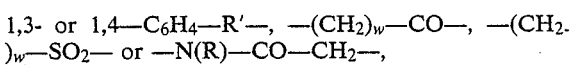

1,3- or 1,4-$C_6H_4-R'-$, $-(CH_2)_w-CO-$, $-(CH_2)_w-SO_2-$ or $-N(R)-CO-CH_2-$, in which R represents hydrogen or methyl, R' represents —CO—(CH$_2$)$_u$—, —SO$_2$—(CH$_2$)$_u$ or —CO—N(R)—C$_1$-C$_5$-alkylene, w represents 1, 2 or 3 and u represents 0, 1, 2 or 3.

Particularly suitable bridging members A$^3$ are the following, in which the side of the bridging member marked, if appropriate, with * is linked to the imide nitrogen atom: C$_1$-C$_7$-alkylene, 1,3- or 1,4—*C$_6$H$_4$—CH$_2$—, —C$_6$H$_4$—, —CH$_2$—C$_6$H$_4$—CH$_2$—, —C$_6$H$_{10}$—, —*—(CH$_2$)$_w$—CO—N(R)— C$_1$-C$_7$-alkylene-, —(CH$_2$)$_w$—CO—C$_1$-C$_7$-alkylene-, —*(CH$_2$)$_v$—N(R)—CO—CH$_2$—,

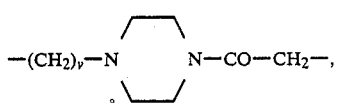

—*C$_6$H$_4$—CO—NH—C$_1$-C$_7$-alkylene, —*C$_6$H$_4$—CO—(CH$_2$)$_w$—, —*C$_6$H$_4$— NH—CO—CH$_2$—, —*N(R)—CO—CH$_2$— or, linked to the noncationic N atom of a piperazinium radical, also —*C$_6$H$_4$— CO—, —*C$_6$H$_4$—SO$_2$—, —*(CH$_2$)$_w$—CO— or *(CH$_2$)$_w$—SO$_2$—. Here, R denotes H or CH$_3$; v=2 or 3 and w=1, 2 or 3.

The bridging members A$^1$ are not present if a cyclic ammonium or sulphonium group is linked to the imide nitrogen via one of its ring C atoms, for example in the following manner:

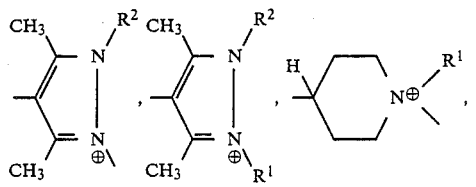

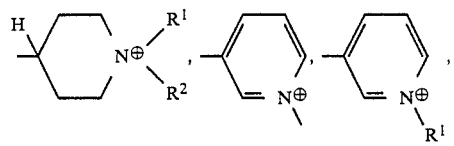

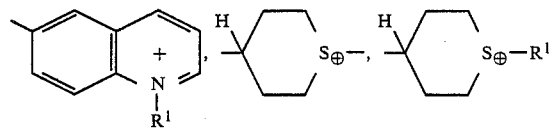

Preferred bridging members -(A$^2$)$_p$-W between the ammonium and/or sulphonium groups correspond to the formula -(A$^4$)$_p$-W$^1$ Here,

A$^4$=-Z-Y-,

Z=C$_1$-C$_5$-alkylene, —C$_6$H$_4$—CH$_2$, xylylene, phenylene, cyclohexylene or a single bond, Y=—O—, —S—, —N(R)—, —N(R)—NH—, —CO—, —CO—NH—CO—, —CO—NH—CH$_2$—, —SO$_2$—, —OCO—, —N(R)CO—, —N(R)—NH—CO—, —CON(R)—, —SO$_2$N(R)—, —COO—, —N(R)—CO—NH—, —N(R)—CH$_2$—CO—, —N(R)—CH$_2$—CO—NH— or a single bond, W$^1$=—CO— or a p-bonded radical from the series comprising C$_1$-C$_{10}$-alkylene, benzene, naphthalene, anthracene, phenanthrene, 9,10-dihydrophenanthrene, cyclohexane, fluoren-9-one (3,6), thiophene (2,5), dibenzofuran (3,6), dibenzothiophene (3,6), dibenzothiophene S-dioxide (2,7), 9H-thioxanthene S-dioxide, (3,6), carbazole (3,6), 9H-xanthen-9-one (2,7), 9-acridone (2,7), 1,3,4-oxadiazole (2,5), 1,2,4-oxadiazole (3,5), 1,3,4-thiadiazole (2,5), s-triazine (2,4,6), piperazine (1,4), 1,2,-dihydro1,2,4,5-tetrazine (3,6), radicals of the formulae

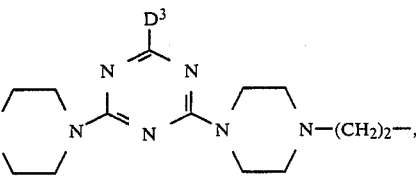

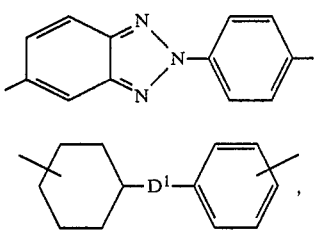

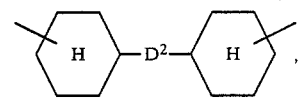

or a single bond.

D$^1$, D$^2$=single bond, optionally —O—interrupted C$_1$-C$_5$-alkylene radical, —O—C$_2$-C$_4$-alkylene—O—, —O—, —N(R)—, —CO—, —CO—NH—, —NH—CO—NH—, 1,1-cyclohexylene or a radical of the formula

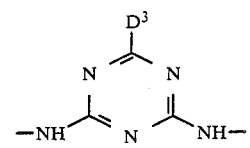

D$_3$=Cl, OR, NR$^1$R$^2$,

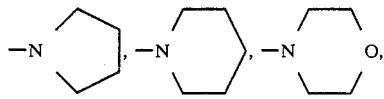

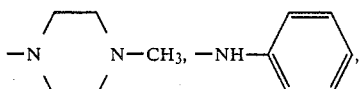

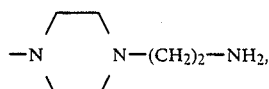

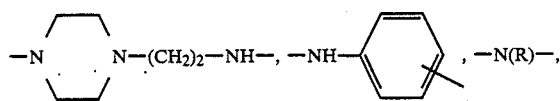

$D^1=$, in addition, $-CH(C_6H_5)-$, $-CH(C_6H_4-)-$, $-N(C_6H_5)-$, $-CH=CH-$, $-S-$, $-SO_2-$, m- or p-phenylene, thiophene(2,5), 1,3,4-oxadiazole(2,5), 1,3,4-thiadiazole(2,5), oxazole(2,5), thiazole(2,5), 1,2-dihydro-1,2,4,5-tetrazine(3,6) or

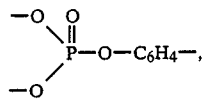

$D^2=$, in addition, $-CH(C_6H_{11})-$ or $-CH(C_6H_{10})-$, and the rings mentioned under $W^1$ can be substituted in the nucleus by $C_1-C_4$-alkyl, $C_1-C_4$-alkoxy or chlorine, and in which R, $R^1$ and $R^2$ have the abovementioned meaning.

Examples of typical bridging members between the ammonium and/or sulphonium groups are the following: $-CH_2-CH_2-$, $-CH_2-CH_2-CH_2-$,

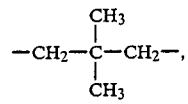

$-CH_2-CO-CH_2-$, $-CH_2-SO_2-CH_2-$, $-CH_2-CO-NH-(CH_2)_2-NH-CO-CH_2-$, $-CH_2-NH-CO-NH-CH_2-$,

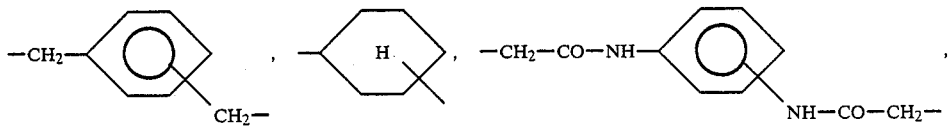

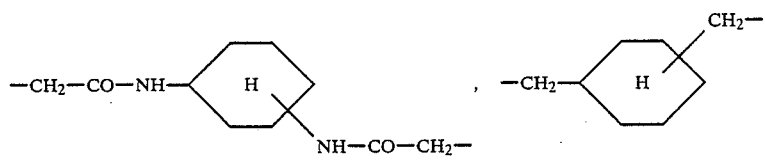

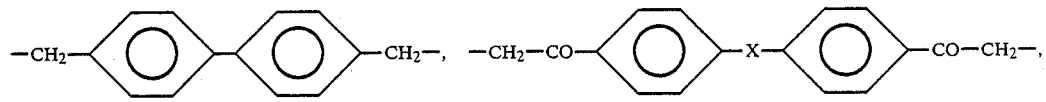

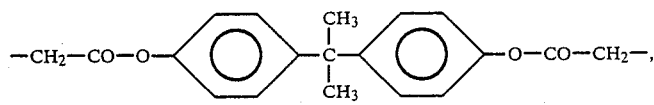

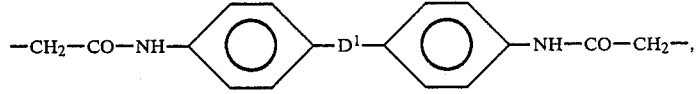

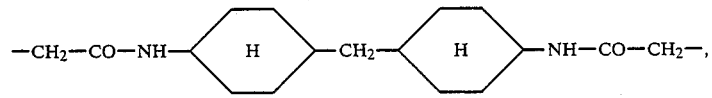

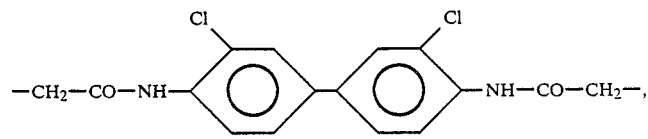

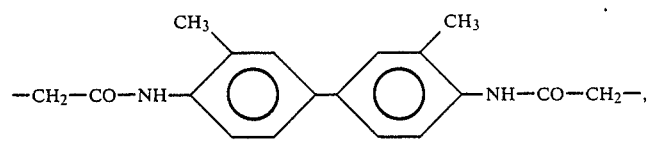

-continued
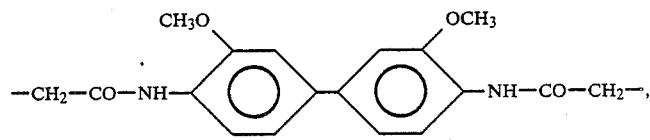
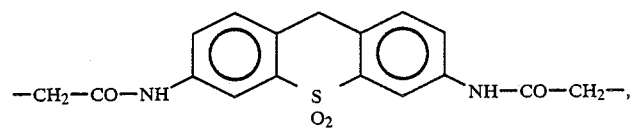
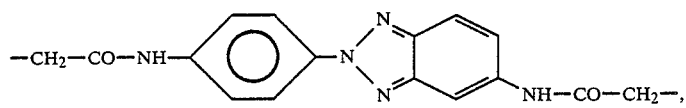
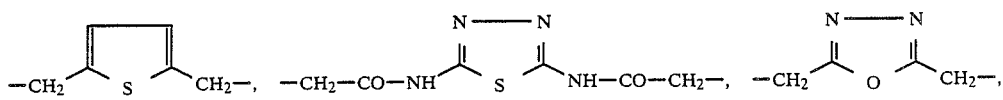
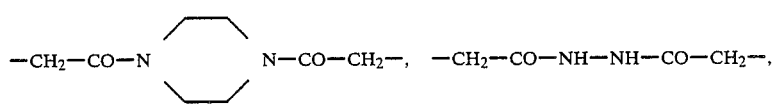
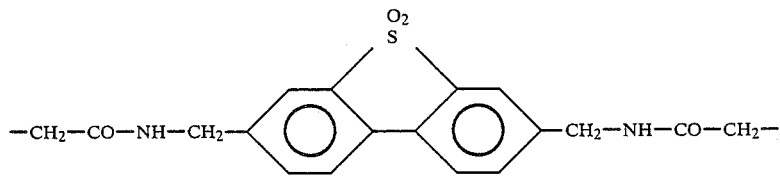
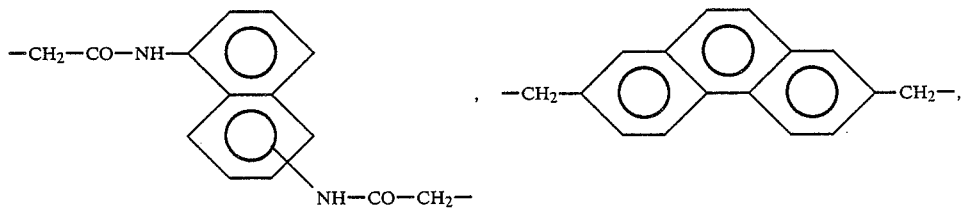
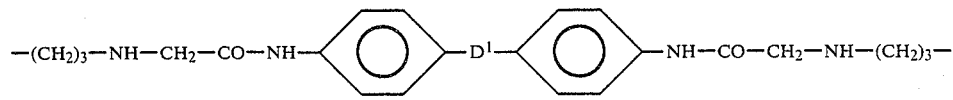
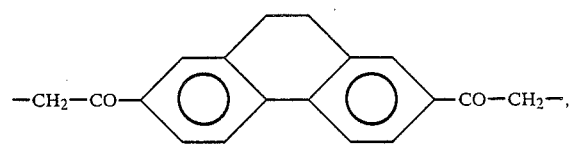

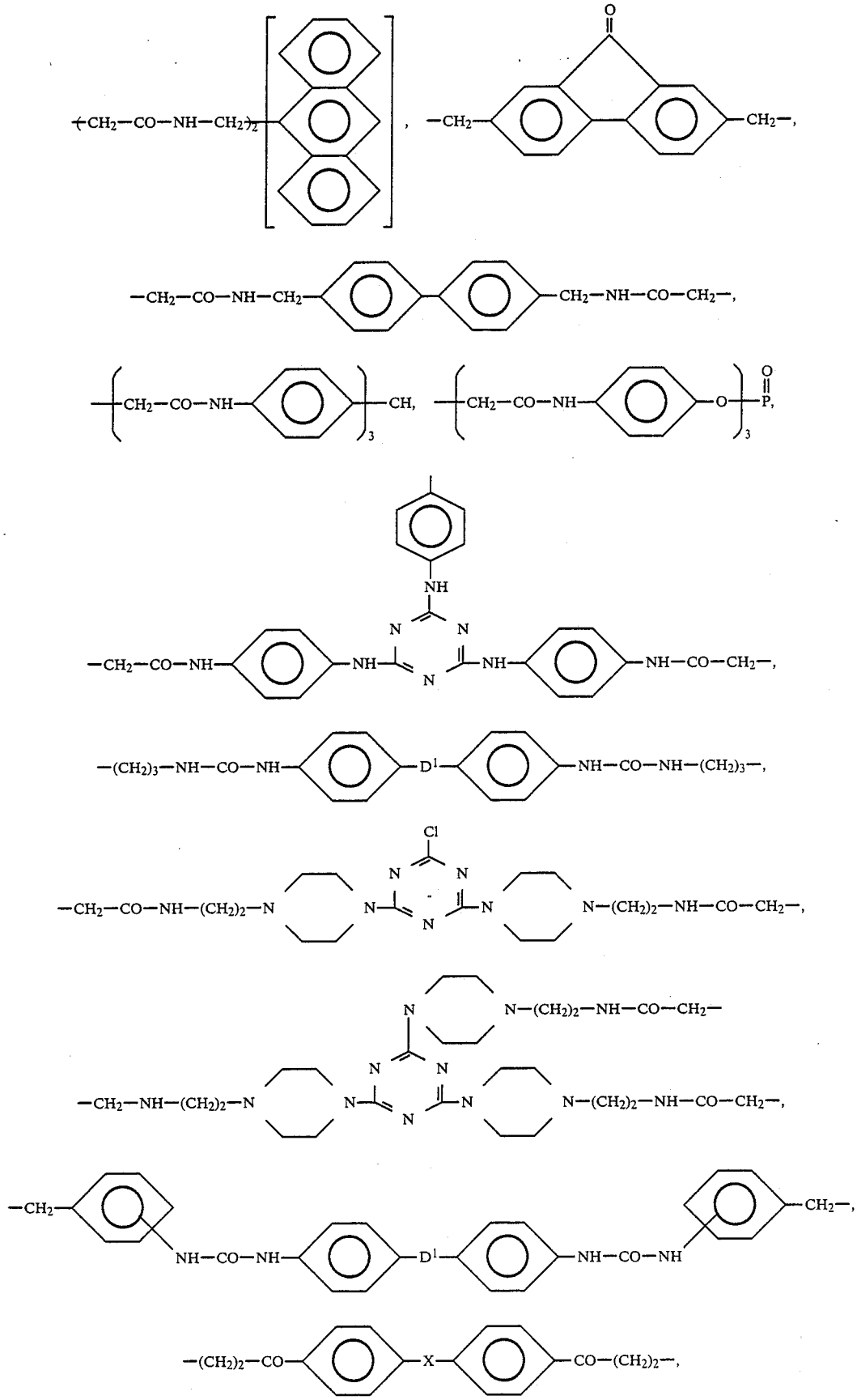

-continued

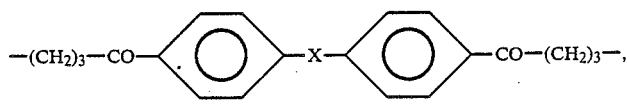

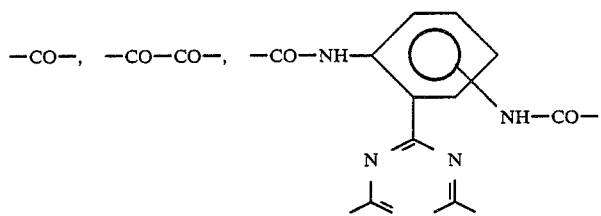

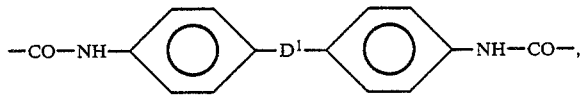

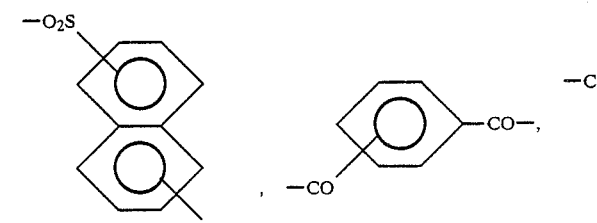

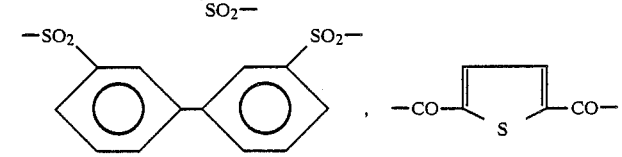

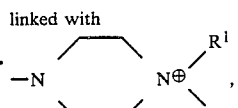

linked with

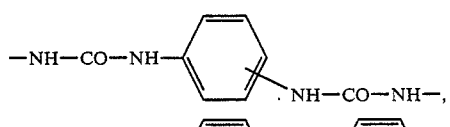

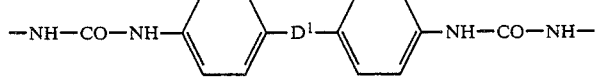

linked with

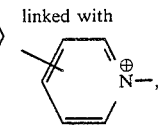

in which
X=—O—, —S— or —N(R)— and
R and D¹ have the abovementioned meaning.

Examples of typical bridging members -A¹-A²-W-A²-A¹-between imide nitrogen atoms or 2 radicals of the formula (II) and/or (III), preferably between an imide nitrogen atom of each of two radicals of the formula (III), are:

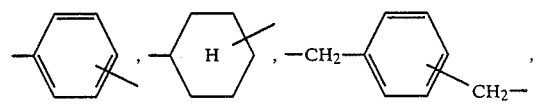

-continued

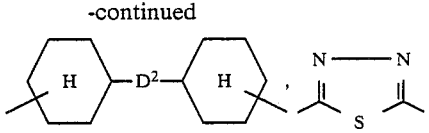

and $C_2$–$C_{10}$-alkylene radicals, which can be interrupted by 1 to 2 —O—, 1 to 2 —NH—, —N(CH$_3$)— or

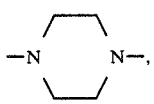

such as for example —(CH$_2$)$_2$—O—(CH$_2$)$_2$—, —(CH$_2$)$_2$—NH—(CH$_2$)$_2$—, —(CH$_2$)$_3$—O—(CH$_2$)$_4$—O—(CH$_2$)$_3$—, —(CH$_2$)$_3$—NH—(CH$_2$)$_3$—, —(CH$_2$)$_3$—N(CH$_3$)—(CH$_2$)$_3$—, —(CH$_2$)$_2$—NH—(CH$_2$)$_2$—NH—(CH$_2$)$_2$—,

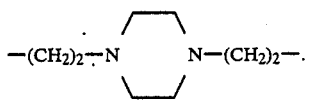

$D^1$ and $D^2$ have the abovementioned meaning.

In the context of the formula I, preferred compounds correspond to the formula

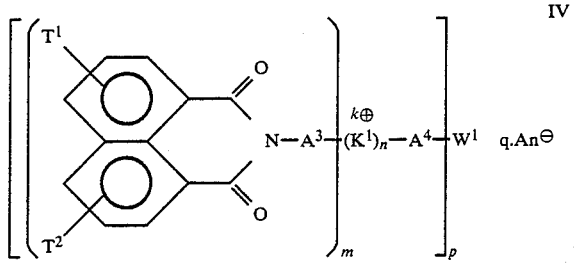

IV in which $T^1$ and $T^2$ each represent hydrogen, chlorine, bromine, hydroxy, alkoxy, benzyloxy, phenoxy, cyclohexyloxy, cyano, carboxy, alkoxycarbonyl, alkylcarbonyl, alkylcarbonyloxy, benzoyloxy, carbamoyl or sulphamoyl radicals, which can be substituted by 1 to 2 alkyl radicals, sulphonyl or carbonylpyrrolidino, -piperidino, -morpholino, -N'-alkyl-piperazino,

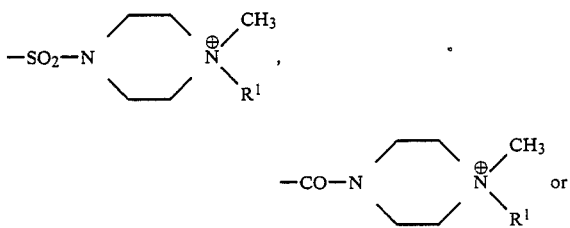

alkylsulphonyl, $T^1$ and $T^2$, also together in the peri-position, represent $-CH_2-CH_2-$, $-CO-O-CO-$ or $-CO-N(T^3)-CO-$, $T^3$ represents hydrogen, -O-alkyl, alkyl, allyl, phenyl, cyclohexyl, phenyl-$C_1$-$C_3$alkyl, pyridyl(2), -(3) or -(4), thiazole-2-yl, benzothiazol-2-yl, 1,2,4-triazol-3-yl, pyrazol-5-yl, imidazol-2-yl, benzimidazol-2-yl, pyrimid-2-yl, -N(R)-CO-alkyl, -N(R)-CO-phenyl, -$A^3$-$E^{1\oplus}$ or in the case where m=1, two $T^3$ groups together also represent a doubly bridging radical -$A^3$-$K^{1\oplus}$-$A^4$- or -$A^3$-$K^{1\oplus}$-$A^4$-$W^1$-$A^4$-$K^{1\oplus}$-$A^3$- with formation of a high molecular weight structure, in which the alkyl radicals contain 1 to 6 C atoms and can be substituted by OH, alkoxy, chlorine or -$E^{1\oplus}$, the alkoxy radicals contain 1 to 4 C atoms and can be interrupted by $-O-$, the phenyl radicals and phenylene radicals and the hetaryl radicals can contain 1 to 2 substituents from the series comprising alkyl, alkoxy, chlorine, bromine, alkoxycarbonyl, alkylsulphonyl, cyano, carboxy, carbamoyl, sulphamoyl, nitro and -$E^{1\oplus}$, in which the indices m and p only denote 1 simultaneously when $T^1$ and $T^2$ together represents peri $-CO-N(T^3)-CO-$, in which n can only be zero when at least one of the radicals $T^1$ and $T^2$ or the radical $T^3$ contains a cationic group -$K^{1\oplus}$- or -$E^{1\oplus}$, in which the grouping -$K^{1\oplus}$-$A^4$-$W^1A^4$-$K^{1\oplus}$- as a whole can also represent

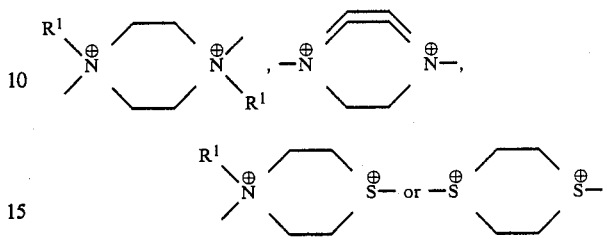

and in which $A^3$, $A^4$, -$K^{1\oplus}$, -$E^{1\oplus}$, $W^1$, $An^\ominus$, R, $R^1$, m, k, n, p and q have the abovementioned meaning.

Preferably, $T^1$ and $T^2$ are in the two peri-positions of the naphthalene ring system. When they are present as univalent radicals, preferred meanings are hydrogen, chlorine, bromine and carboxy.

$T^1$ and $T^2$ together preferably represent $-CO-N(T^3)-CO-$. Among the radicals $T^3$, those which link with a carbon atom to the imide nitrogen are preferred.

When m=2 and p=1, the two radicals $A^3$ can be different from one another.

When p=1, the radical -$A^4$-$W^1$ is preferably =$R^1$ or $R^2$ (as substituent on $K^{1\oplus}$.

In the context of the formula (IV), a preferred compound type corresponds to the formula

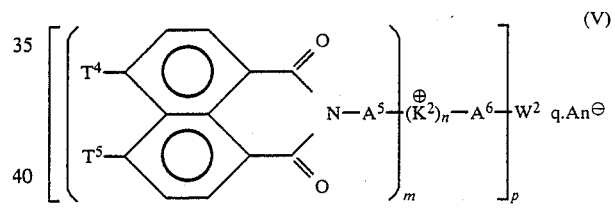

(V)

in which $T^4$ and $T^5$ represent hydrogen, chlorine or bromine, or $T^4$ and $T^5$ together represent a $-CO-N(T^6)-CO-$ group, $T^6$ represents hydrogen, OH, $C_1$-$C_6$-alkyl which is optionally substituted by 1 to 2 OH groups, chlorine, $C_1$-$C_4$-alkoxy or COOH, allyl, phenyl, or benzyl which can be substituted by 1 or 2 $C_1$-$C_4$-alkyl, chlorine, $C_1$-$C_2$-alkoxy, bromine, carboxy, cyano, $C_1$-$C_2$-alkoxycarbonyl, $C_1$-$C_2$-alkylsulphonyl, carbamoyl or sulphamoyl, $\beta$-aminoethylphenyl, pyridyl-(2)- or -(3)-, benzothiazol-(2)-yl, 1,2,4-triazol-3-yl, cyclohexyl, -$A^5$-$E^{2\oplus}$ or, in the case where m=1, n=0 and p=1, represents a grouping of the formula -$A^5$-$K^{2\oplus}$-$A^6$- or -$A^5$-$K^{2\oplus}$-$A^6$-$W^2$-$A^6$-$K^{2\oplus}$-$A^5$-, $A^5$ and $A^6$ or the two radicals $A^5$ being bonded to 2 different 1,4,5,8-naphthalenetetracarboxylic acid diimide molecules and thus making the specified structure as a whole into the repeating unit of a high molecular weight compound, $A^5$ represents a single bond, $C_1$-$C_5$-alkylene, m- or p—$C_6H_4$—$CH_2$—, $A^6$ represents a single bond, $-CH_2-$, $-CH_2-CO-O-$, $-CH_2-CO-N(R)-$, $-CH_2-SO_2-N(R)-$, $-(CH_2)_2-CO-N(R)-$, $-CH_2-CO-NH-CH_2-$, $C_1$-$C_5$-alkylene- N(R)—CO—, C₁-C₅-alkylene-N(R)—SO₂—, C₁-C₅-alkylene-N(R)—CO—NH—, —CH₂—C₆H₄—NH—CO—, —CH₂—C₆H₄—NH—SO₂—, —CH₂—C₆H₄—NH—CO—NH—, —(CH₂)_w—CO—, —(CH₂)_w—CO—C₆H₄—NH—CO—, —(CH₂)_w—CO—C₆H₄—NH—SO₂—, —(CH₂)_w—CO—C₆H₄—NH—CO—NH—, in addition: —SO₂—, —CO— or —CONH—, when K²⊕=piperazinium, and —NH—CO—NH—, when K²⊕=pyridinium, K²⊕ represents

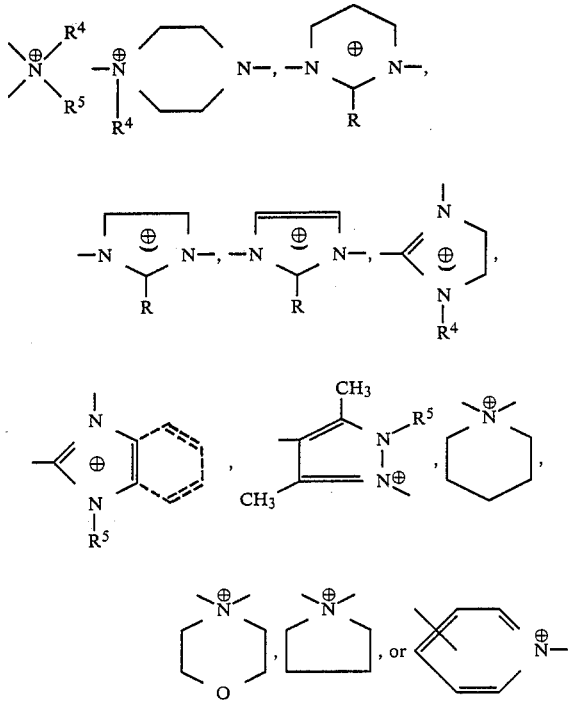

or -E²⊕ represents

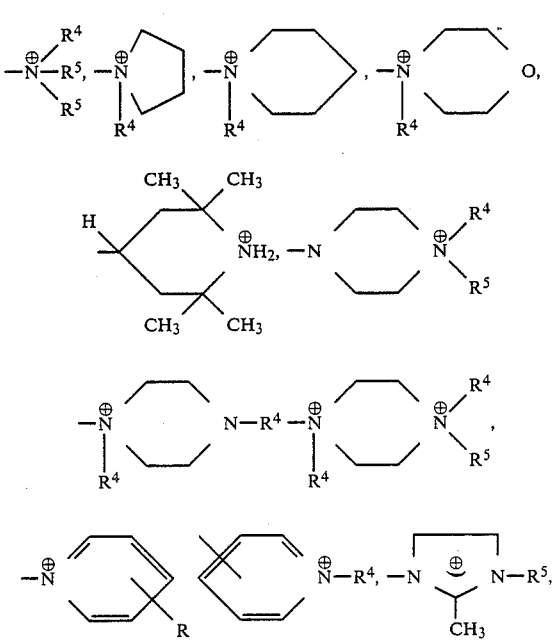

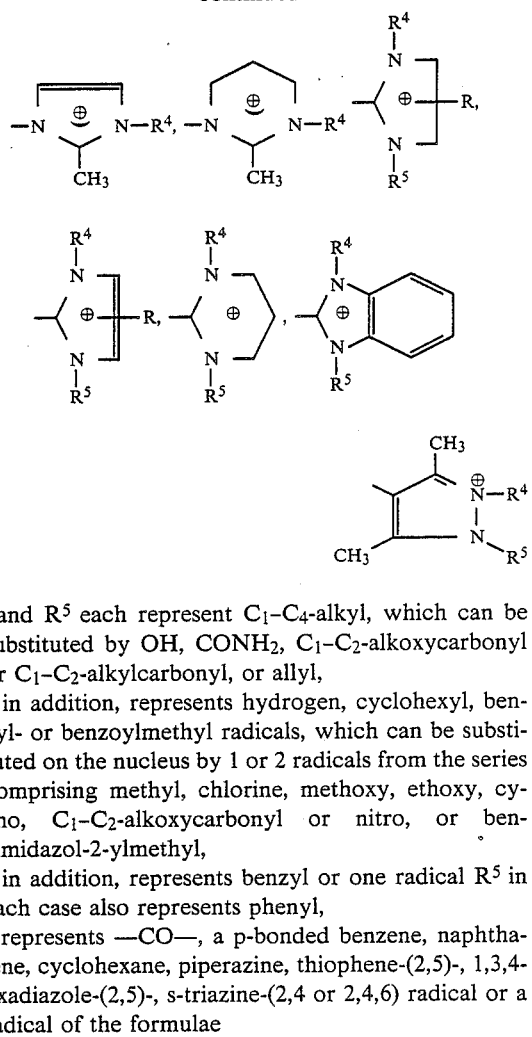

R⁴ and R⁵ each represent C₁-C₄-alkyl, which can be substituted by OH, CONH₂, C₁-C₂-alkoxycarbonyl or C₁-C₂-alkylcarbonyl, or allyl, R⁴, in addition, represents hydrogen, cyclohexyl, benzyl- or benzoylmethyl radicals, which can be substituted on the nucleus by 1 or 2 radicals from the series comprising methyl, chlorine, methoxy, ethoxy, cyano, C₁-C₂-alkoxycarbonyl or nitro, or benzimidazol-2-ylmethyl, R⁵, in addition, represents benzyl or one radical R⁵ in each case also represents phenyl, W² represents —CO—, a p-bonded benzene, naphthalene, cyclohexane, piperazine, thiophene-(2,5)-, 1,3,4-oxadiazole-(2,5)-, s-triazine-(2,4 or 2,4,6) radical or a radical of the formulae in which, in the case where p=1, one of the specified free valences is saturated by hydrogen, D⁴ and D⁵ each represent CH₂, a C₂-C₅-alkylene radical (particularly —CH₂—, —CH(CH₃)—, —C(CH₃)₂ and —CH₂CH₂—) which is optionally interrupted by —O—, —N(R)—, -O-C₂-C₄-alkylene-O- or a radical of the formula

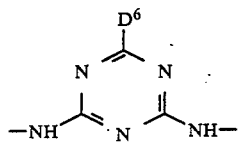

where $D^6 = Cl$, $OR$, $-N(R^4R^5)$.

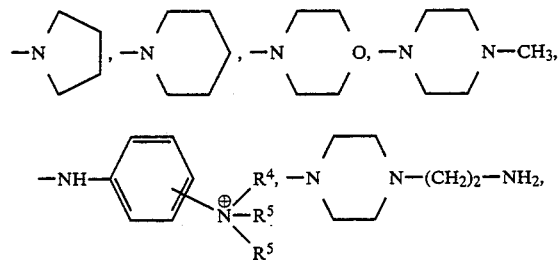

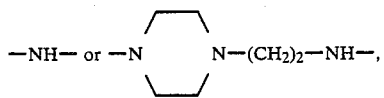

$D^4$, in addition, represents 1,1-cyclohexylene, p-phenylene, $-CH(C_6H_5)-$, $-CH(C_6H_4-)-$, $-S-$, $-SO_2-$, $-CO-NH-$, $-NH-CO-NH-$,

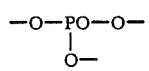

or a single bond,
it being possible for the rings mention in $D^4$, $D^5$, and also in $W^2$, to be substituted by $CH_3$, $CH_3O$ or $Cl$,
in which, in the case where p=2, the grouping $-K^2\oplus-A^6-S^2-A^6-W^2\oplus-$ as a whole can also represent

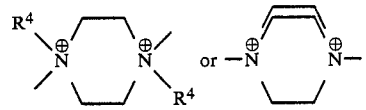

in which the indices m and p only denote 1 simultaneously when $T^4$ and $T^5$ form a cyclic peridicarboxylic acid imide grouping,
in which n, p, q, $An^\ominus$ and R have the same meaning as in formula IV,
and in which n can only be zero when $T^6$ contains a cationic group $-K^2\oplus-$ or $-E^2\oplus$.
Of the compounds (V), the compounds

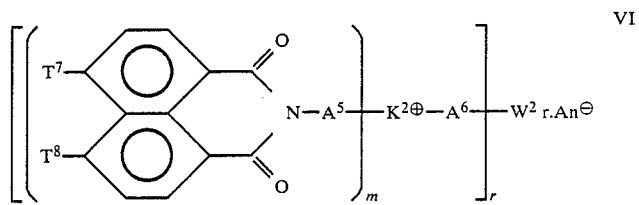

VI with
$T^7$ and $T^8$ = hydrogen, chlorine or bromine,
r=2 or 3,
in which
the radicals $A^6$ and - when m=2 - the radicals $A^5$ can be different from one another, and

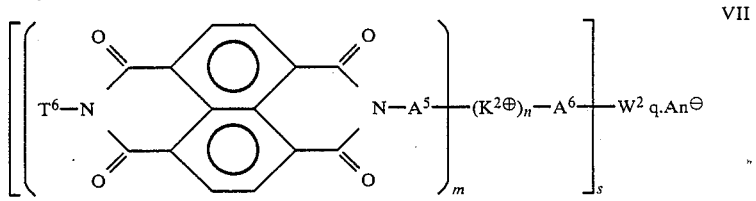

VII with s=1 or 2 should be emphasized.
In (VI), $T^7$ and $T^8$ preferably represent hydrogen, and, in formula (VII), m preferably one denotes 2 when s represents 1 and $-A^6-W^2$ represents $R^4$ or $R^5$.
Of the compounds (VI) and (VII), the following should be mentioned particularly:
A.
VI with m=1 and
VII with m and n=1.
B.

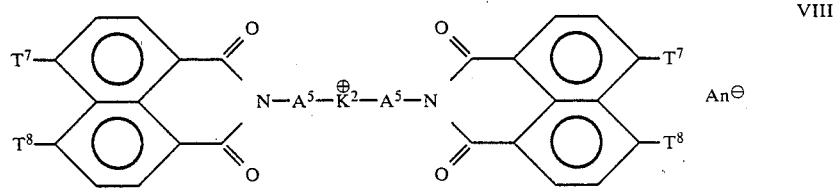

VIII and

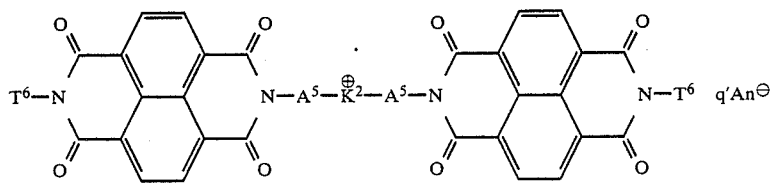 IX in which the two radicals $A^5$, $T^6$, $T^7$, $T^8$ can be identical or different in each case and $T^7$ and $T^8$ denote particularly hydrogen.

Of the compounds (VII), the following should be mentioned in addition:

C.

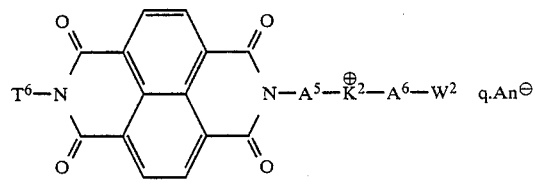 X in which $W^2$ is terminal and also represents hydrogen.

D.

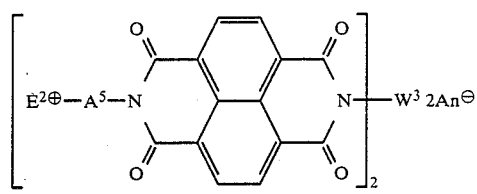 XI in which
$W^3$ represents $C_2$–$C_{10}$-alkylene, which can be interrupted by 1 or 2 —O—, —NH—, —N(CH$_3$)— or

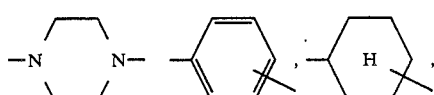

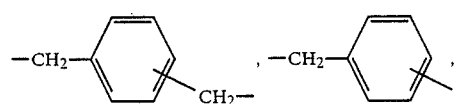

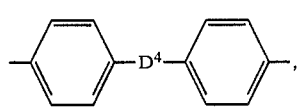

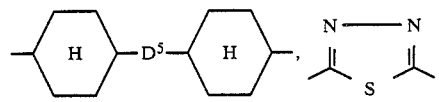

and
$D^4$ and $D^5$ have the abovementioned meaning.

E. Compounds with the repeating unit

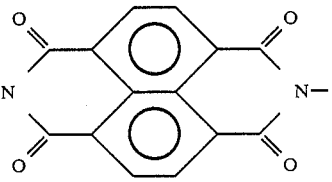 XII

F. Compounds with the repeating unit

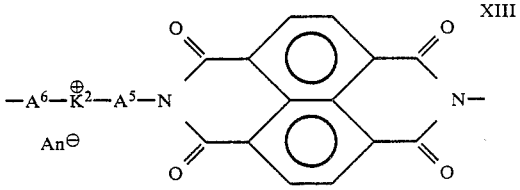 XIII

Of the tetracarboxylic acid diimide derivatives mentioned under A–C, those with $T^6 = -A^5-E^{2\oplus}$ may be particularly emphasized.

The invention also relates to compounds of the general formula (VI), compounds of the general formula (VII) and processes for their preparation.

Compounds (VI) are prepared by reaction
(a) of compounds of the formula

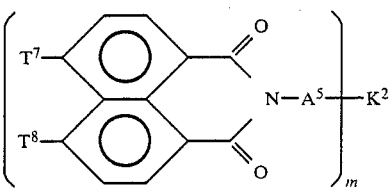 XIV in which
$T^7$, $T^8$, $A^5$ and m have the same meaning as in formula VI and
-K$^2$ denotes the non-cationic terminal basic precursor of -K$^{2\oplus}$, in the molar ratio r:1 with compounds of the formula $(L-A^6)_r W^2$ in which $A^6$, r and $W^2$ have the same meaning as in formula VI and L denotes a group which can be cleaved off as an anion, (b) of compounds of the formula $$[T^7\text{-, }T^8\text{-naphthalimide-}N-A^5\text{-}]_m L \qquad \text{XVI}$$

in which $T^7$, $T^8$, $A^5$ and m have the same meaning as in formula VI and

L denotes a group which can be cleaved off as an anion, in the molar ratio r:1 with compounds of the formula $$(K^2-A^6-)_r W^2 \qquad \text{XVII}$$

in which $K^2$-, $A^6$, r and $W^2$ have the abovementioned meaning, (c) of compounds of the formula (XIV) in equimolar ratio with compounds of the formula (XVI), (d) of compounds of the formula $$\left[\left(T^7\text{-, }T^8\text{-naphthalimide-}N-A^5-B^2-A^6\right)_m-W^2\right]_r \qquad \text{XVIII}$$

in which

-$B^2$- represents —N($R^5$)—,

[piperazine, tetrahydropyrimidine, imidazoline structures]

[benzimidazole structure]

or, for the preparation of further compounds of the formula I, also represents

[various structures including —S—, piperazinium, thiomorpholinium]

$T^7$, $T^8$, $A^5$, m, R, $R^5$, $A^6$, r and $W^2$ have for the same meaning as in formula VI, in the ratio 1:r with compounds of the formula $$R^4\text{—L} \qquad \text{XIX}$$

in which $R^4$ has the same meaning as in formula VI and

L represents a group which can be cleaved off as, anion.

The reaction is expediently carried out in a solvent such as dimethylformamide, N-methylpyrrolidone, dimethylsulphoxide, acetonitrile, ethylene glycol, diethylene glycol, triethylene glycol, polyglycol mixtures, preferably with an average molecular weight of about 400, acetone, methyl ethyl ketone, cyclohexanone, toluene, chlorobenzene, o-dichlorobenzene, water and homogeneous or inhomogeneous mixture of these in the temperature range from 20°–180° C., preferably 40°–150° C.

The other naphthalimide derivatives of the formula I with n=1 can also be prepared in an analogous fashion.

Suitable radicals -$K^2$ and, in the more general meaning, -$K^1$ or -K correspond to the following formulae:

—N($R^4R^5$), —N(piperazine)N—$R^5$, H-N(piperidine)N—$R^5$,

—N=C(R)-N (tetrahydropyrimidine), N(R)-N=(imidazoline)-$R^5$, —N—$R^1$ / NH$_2$, —N=C(R)N—, —N=C(R)N—, imidazoline-$R^5$, benzimidazole-$R^5$, dimethyldihydropyrazine-$R^5$, —N(piperidine), —N(morpholine)O, —N(pyrrolidine), various pyridyl/quinolinyl amidine structures, benzimidazoline-R, pyrazole-N—

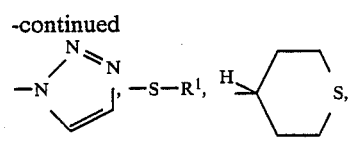

Here, R, $R^4$ and $R^5$ have the abovementioned meaning.

Radicals L which can be cleaved off as an anion are the leaving groups, known from alkylation agents, such as halogen (chlorine, bromine, iodine) and arylsulphonic acid ester radicals such as tosylate or benzenesulphonate.

Some of the starting materials of the formula (XIV) are known, particularly as starting compounds for cationic optical brighteners, as used for the whitening of polyacrylonitrile fibres.

Suitable starting compounds of the formula XIV are, for example: naphthalic acid N-(3-dimethylaminopropyl)-imide, 4-chloronaphthalic acid N-(2-diethylaminoethyl)-imide, 4-bromonaphthalic acid N-(α-dimethylaminobenzyl)-imide, 4,5-dichloro-naphthalic acid N-(β-N'-methyl-piperazinoethyl)imide, naphthalic acid N-(methyl-pyridyl)-(4))-imide, naphthalic acid N-(β-N'-morpholinoethyl)-imide.

Examples of suitable starting compounds of the formula XV are 1,2- dichloroacetone, 1,4-bischloromethylbenzene, 1,4-bisbromomethylbenzene, 2,4-bis-chloromethyl-1,5-dimethylbenzene, 1,3,5-tris-chloromethylbenzene, 4,4'-bischloromethylbiphenyl, 1,4-bischloromethylnaphthalene, 2,6-bischloromethylnaphthalene, 4,4'-bischloromethyl-benzophenone, -diphenyl sulphone, -diphenylamine, -N-methyl-diphenylamine, -triphenylamine, -diphenyl ether, -diphenyl sulphide, -diphenylmethane, -triphenylmethane, -diphenylpropane-(2), tris-(4-chloromethyl-phenyl)-methane, 2,5-bischloromethyl-thiophene, -1,3,4-oxadiazole, -1,3,4-thiadiazole, N,N',N''-trischloromethyl-s-triazine-2,4,6-trione, N,N',N''-trismethylolcyanuric acid p-toluenesulphonic acid triester, 4,4'-bis-chloroacetamido-benzoic acid anilide, 4,4'-bis-(chloroacetamidomethyl)-biphenyl (U.S. patent specification No. 4,370,486), 4,4'-bis-(chloroacetamido)-triphenyl-methane, -diphenylmethane or -3,3'-dimethoxy-biphenyl, 4,4',4''-tris-(chloroacetamido)-triphenylmethane, 4,4',4''-tris-(chloroacetamido)triphenylphosphate, bis-(4,-chloroacetamidocyclohexyl)methane, 2,2-bis-(4-chloroacetamidocyclohexyl)-propane(2), 4,4'-bis-chloroacetyl-diphenyl ether, 4,4'-bis-chloroacetyldiphenyl sulphide, 4,4'-bis-(chloroacetureido)-diphenylmethane, 4,4',4''-tris-(chloroacetureido)-triphenylmethane (from 4,4',4''-triaminotriphenylmethane and 3 equivalents of chloroacetylisocyanate), 3,6-bischloroacetamido-9H-thioxanthene-S-dioxide, 4,4'-bis-(chloroacetoxyphenyl)propane-(2), 2,4-(bis-(p-chloroacetamidophenylamino)-6-chloro-1,3,5-triazine, 2,4,6-tris(p-chloroacetamidophenylamino-1,3,5-triazine, 2,4-bis-(β-chloroacetamidoethylpiperazino)-6-morpholino-1,3,5-triazine, N,N'-bis-chloroacetyl-piperazine, N,N'-bis-(ω-bromoacetophenyl)-urea, N,N'-bis-(ω-chloroacetophenyl)-guanidine, N,N'-bis-chloroacetyl-hydrazine.

Examples of suitable starting compounds of the formula XVI are: N-chloroacetamido-naphthalimide, 4-chloro-N-chloroacetamido-naphthalimide, 4,5-dichloro-N-chloroacetamido-naphthalimide, 4-bromo-N-chloroacetamido-naphthalimide, N-(2-p-toluenesulphonyl-oxyethyl)-naphthalimide, N-(2-bromoethyl)-naphthalimide, N-(3-N'-methyl-N'-chloroacetamidopropyl)-naphthalimide, N-(p-chloroacetamidophenyl)-naphthalimide, N-(ω-bromoacetophenyl)-naphthalimide.

The starting materials of the formula XIV and XVI are advantageously prepared by condensing anhydrides of the formula

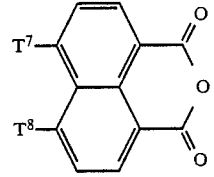

XX in which $T^7$ and $T^8$ have the abovementioned meaning, in the molar ratio m:1, cleaving off m equivalents of water, with compounds of the formula

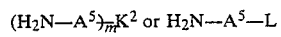

$(H_2N-A^5)_{\overline{m}}K^2$ or $H_2N-A^5-L$

XXI          XXII in which $A^5$, m, $K^2$ and L have the abovementioned meaning.

Examples of suitable starting compounds of the formula XXI are: 1-amino-3-dimethylamino-propane, 1-amino-3-methylamino-propane, 1-amino-2-diethylamino-ethane, 1-amino-3-cyclohexylamino-propane, 1-amino-2,2-dimethyl-3-dimethylamino-propane, bis-(3-aminopropyl)-methylamino, bis-(3-aminopropyl)amine, diethylenetriamine, triethylenetetramine, 4-amino-1-diethylamino-n-pentane, glycine choline ester, choline β-aminoethyl ether, 2-(2-amino-ethylamino)-ethanol, 2-[(3-aminopropyl)-methylamino]-ethanol, N-(3-aminopropyl)pyrrolidine, N-(2-aminoethyl)-morpholine, N-(2-aminoethyl)piperidine, N-methyl-N'-(2-aminoethyl)-piperazine, 1-(2-aminoethyl)-imidazole, 3- and 4-amino-N,N-dimethylbenzylamine, 4-aminomethyl-N,N-dimethylbenzylamine, 4-aminomethylpyridine, 3-aminopyridine, 2-aminomethyl-benzimidazole, 4-amino-1,3,5-trimethyl-pyrazole, furthermore as starting components for further analogous compounds of the formula I also 1-(3-aminopropyl)-1,2,3- or -1,2,4-triazole, aminoguanidine, 2-mercaptoethylamine or 2-aminobenzothiazole.

Examples of suitable starting compounds of the formula (XXII) are 3-chloropropylamine, 4-amino-ω-chloroacetophenone, 3-aminobenzyl chloride, 3-chloro-1-aminopropan-2-one.

The reaction is expediently carried out in one of the abovementioned solvents in the temperature range from 60°–180° C., preferably 80°–130° C., advantageously in the presence of catalytic amounts of acid such as glacial acetic acid and advantageously by removing the reaction water by azeotropic distillation.

The reaction of (XX) with (XXI) to give (XIV) and of (XIV) with (XV) or (XVI) can, as a rule and advantageously, occur without intermediate isolation of (XIV).

The starting compounds of the formula (XVII) are obtained simply either by reacting a compound of the formula XV in the molar ratio p:1 with a compound $K^2$-H, $K^2$ having the abovementioned meaning, and simultaneously or subsequently cleaving off p equivalents of H-L using alkali, or by adding p equivalents of a compound of the formula $K^2$-Z-N(R)-H or N-methyl-piperazine, in which $K^2$, R and Z have the abovementioned meaning, to an isocyanate of the formula $W^2(NCO)_p$.

The reaction of (XV) with p equivalents of $K^2$-H is carried out expediently in a dipolar aprotic solvent such as dimethylformamide, N-methyl-pyrrolidone, dimethylsulphoxide or also in acetonitrile, acetone, polyethylene glycol, preferably with an average molecular weight of about 400, in the temperature range from 15°-100° C., preferably 20°-60° C.

Anhydrous aromatics such as toluene, xylene, chlorobenzene and o-dichlorobenzene are particularly suitable for the p-fold addition of $K^2$-Z-N(R)-H or N-methyl-piperazine to $W^2(NCO)_p$. The reaction is preferably carried out at room temperature and the temperature can be allowed to increase to 40°-70° C. during the exothermic reaction.

Examples of suitable compounds of the formula $K^2$-H are dimethylamine, diethylamine, di-n-butylamine, methyl-n-butylamine, dibenzylamine, N-methyl-benzylamine, N-methyl-ethanolamine, pyrrolidine, piperidine, morpholine, N-methyl-piperazine, N-methylimidazole.

Particularly suitable isocyanates $W(NCO)_p$ are: phenyl isocyanate, benzyl isocyanate, phenylene-1,4-diisocyanate, toluylene-2,4-diisocyanate, xylylene-1,3-diisocyanate, naphthylene-1,5-diisocyanate, bis-(4-isocyanatophenyl)-methane, 2,2-bis-(4-isocyanatophenyl)-propane, tris-(4-isocyanatophenyl)-methane, bis-(4-isocyanatophenyl) ether.

Compounds of the formula $K^2$-Z-N(R)-H are, for example, 1-amino-3-dimethylamino-propane, 1-amino-2-diethylamino-ethane, 4-amino-N,N-dimethyl-benzylamine, N,N,2,2-tetramethylpropane-1,3-diamine (=dimethylamineneopentamine), N-(2-aminoethyl)-morpholine, N-(3-amino-propyl)piperidine.

Examples of compounds of the formula $R^4$-L are: dimethyl sulphate, diethyl sulphate, methyl chloride, methyl bromide, methyl iodide, methyl p-toluenesulphonate, ethyl iodide, propyl bromide, n-butyl bromide, ethylene oxide (+glacial acetic acid), propylene oxide (+glacial acetic acid), aziridine (+glacial acetic acid), acrylonitrile (+glacial acetic acid), chloroacetic acid, ethyl bromoacetate, ethyl acrylate, acrylic acid dimethylpropylamide, chloroacetamide, chloroacetonitrile, 2-methoxyethyl bromide, 3-chloropropyl bromide, allyl bromide, cyclohexyl bromide, benzyl chloride, p-methyl-benzyl chloride, p-chlorobenzyl chloride, 3,4-dichloro-benzyl chloride, o-, m and p-cyanobenzyl chloride, p-methoxybenzyl chloride, p-nitrobenzyl chloride, 1-phenyl-ethyl bromide, 2-phenylethyl chloride, 3-phenylpropyl chloride, ω-chloroacetophenone, ω-bromo-p-chloroaceto-phenone, ω-bromo-propiophenone, 3-benzoyl-propyl bromide, N-phenyl-chloroacetamide, N-p-tolyl-chloroacetamide, N-(4-chlorophenyl)chloroacetamide, 2-chloromethyl-benzimidazole, bromoacetone and, for $R^4$=H, also acids such as HCl, glacial acetic acid or lactic acid.

Compounds of the formula (I) which contain terminal $-E^{1\oplus}$ can be prepared by reacting the corresponding noncationic basic precursor of $-E^{1\oplus}$, which corresponds to the formula $-E^1$, in equimolar ratio with compounds of the formula $R^1$-L, $R^1$ and L having the abovementioned meaning. The reaction conditions are the same as for (XVIII)+(XIX). Suitable radicals $-E^1$ are the same as mentioned for $-K^2$.

Some of the compounds of the naphthalenetetracarboxylic acid diimide type (VII), particularly (X), are known (DE-B 1,225,191, FR-A 1,512,338, SU-A 253,047 and 259,875; Pharm. Chem. J. 5 (1971) 515–519, Khim. Farm. Zh. 8 (1974) 11–13, 12 (1978) 50 and 16 (1982) 801–806). The others are accessible in an analogous fashion. Unsymmetric naphthalenetetracarboxylic acid diimides can also be prepared analogously to DE-A-3,309,060.

Typical anionic optical brighteners are those which belong to the stilbene, distyrylbenzene, distyrylbiphenyl and 1,3-diphenyl-pyrazoline series, particularly 4,4'-bistriazinylaminostilbene 2,2'-disulphonic acids, 4,4'-bis-triazolylstilbene 2,2'-disulphonic acids, naphtho-triazolylstilbene mono- or disulphonic acids and 4,4'-bis-(sulphostyryl)biphenyl types. They are described by, inter alia, H. Gold in K. Venkataraman, The Chemistry of Synthetic Dyes, Vol. V, p. 535–678, and in Ullmanns Encyclopädie der technischen Chemie [Ullmann's Encyclopaedia of Industrial Chemistry] (4th edition, volume 17, pages 459 to 473. The cationic naphthalene-peri-dicarbonate acid imide compounds emphasize the white tone on the treated substrates by quenching the blue fluorescence of the anionic whiteners. The process can be carried out so that whitened substrates such as natural, semi-synthetic or synthetic substrates, for example natural or regenerated cellulose, paper pulps or paper sheets, paper coatings, silk, wool, jute, hemp and also synthetic polyamides, or also residues of whiteners are treated with the naphthalene-peri-dicarboxylic acid imide compounds.

The process according to the invention can also be used to obtain pale, clear colour tones on cellulose materials if the naphthalene-peri-dicarboxylic acid imide compounds are added to the dyebath, or if the cellulose materials are after- or pre-treated with the compounds. In this manner, the disadvantageous influence of washing agent whiteners on the colour tone is avoided or neutralized.

The process according to the invention is particularly well suited for the preparation of non-brightened paper when using whitened paper as raw material, for rapid, easy removal of undesired residues of optically brightened paper pulps in paper machines and for the inactivation of undesired residues of aqueous or organic, water-miscible solutions or dyebaths of anionic whiteners in dyeing equipment, dyeing machines, storage vessels and supply lines. Undesired whitening or fluorescence effects still caused by these residues in subsequent application processes which are themselves whitener-free are avoided.

In the coating of paper, the cationic naphthalene-peri-dicarboxylic acid imide derivatives can be distributed in the coating compound (such as starch) and thus applied to the paper surface by means of the coating operation.

In the preparation of non-whitened paper from whitener-containing scrap paper, the cationic naphthalene-peri-dicarboxylic acid imide derivatives, because of their good substantivity, are rapidly absorbed onto the fibres after addition to the aqueous cellulose fibre suspension and are thus not left behind in the water during the formation of paper sheets.

In whitened, finished paper, the whitening can be neutralized by impregnating the paper with the aqueous solution of the cationic naphthalene-peri-dicarboxylic acid imide derivative. This effect can also be used specifically for the generation of written or pictorial motifs or watermarks.

The treatment of fabrics, for example cotton, can be carried out in aqueous medium according to known processes, for example the Foulard or padding mangle process.

The solubility in water of the naphthalene-peri-dicarboxylic acid imide compounds is generally at least 1 g/l at 20° C. Concentrated, about 10 to 30% strength by weight organic or organic-aqueous stable solutions, which are infinitely miscible with water at room temperature, are advantageously prepared from the crystalline compounds.

The same solvents as are used, as is known, for the preparation of stable liquid formulations of cationic substantive dyes are advantageously suitable, for example ethylene glycol, diethylene glycol, triethylene glycol, 2-methoxy-propanol, ethylene carbonate, 1,2-propylene carbonate, butyrolactone, caprolactone, 2-cyanoethanol, lactic acid and N-methyl-pyrrolidone. About 5 to 50, preferably 10 to 30, % by weight of a water-soluble carbonamide- or carbonimide-group-containing compound, such as urea, caprolactam, pyrrolidone or dicyanodiamide, are preferably additionally added to such solutions. Further conventional additives, such as, for example, o-hydoxybiphenyl as bactericide in 0.3 to 2% strength by weight, are also advantageous.

For the preparation of the liquid formulation, intermediate isolation of the fluorescence quencher active ingredient in crystalline form can frequently be dispensed with, that is to say the synthesis is carried out in a solvent intended for the liquid formulation in such a manner that the stable solution of the fluorescence quencher is obtained directly.

About 1 to 5, preferably 1 to 3, parts by weight are employed per part by weight of the optical brightener. The amount employed relative to dry substrate is preferably between 0.05 and 0.3% by weight. The application occurs, for example, at pH values from 3 to 9.5, preferably 4 to 8.5, at temperatures from 10° to 100° C., preferably 18° to 60° C., and particularly at 20° to 40° C.

Cationic fluorescence quenchers are already known from DE-A-1,912,647 and DE-A-2,448,293. Compared to these compounds, the compounds of the process according to the invention show increased and more complete fluorescence quenching action.

The superiority is particularly evident in the neutral to weakly alkaline application range of pH 7 to 9.5. Since virtually complete neutralization of the white effect caused by anionic whiteners is achieved even when relatively small amounts are employed, significantly less impairment of the newly applied anionic whitener occurs during a desired re-whitening of the cellulose substrate, so that relatively small amounts of whitener are adequate for creation of a particular white effect.

The fluorescence quenchers to be used according to the invention are characterized in addition by good resistance to the influence of hydrolysis and of light and by a high substantivity on cellulose. They are virtually colourless and do not create any undesired discolorations on the brightener-containing substrate.

It is noteworthy that the optical brighteners in which the fluorescence has been quenched are fixed in the substrate by fluorescence quenchers of the process according to the invention and are thus extracted from the substrate with water to an even lesser extent than without treatment with the fluorescence quencher.

Colourless cationic naphthalimide compounds have hitherto only been used as optical brighteners, particularly for the whitening of polyacrylonitrile fibres. It is therefore surprising that an almost opposite effect, namely the neutralization of brightener effects by quenching fluorescence, can be achieved with the constitutionally very similar cationic naphthalene-peri-dicarboxylic acid imide compounds in a fashion which is outstandingly suitable industrially.

Cationic naphthalimide compounds and their use for the whitening of polyarylonitrile fibres are described, for example, by R. Anliker et al., Das Aufhellen von Polyacrylinitrilfasern [The brightening of polyacrylonitrile fibres], in Textilveredlung [Textile Finishing] 11 (1976), 369 and 370, and A. Dorlars, C-W. Schellhammer, J. Scrhoeder, Heterocyclen als Bausteine neuer optischer Aufheller [Heterocyclic compounds as components of new optical brighteners], Angew. Chem. 87 (1975), 693.

PREPARATION EXAMPLES

Example 1

282 g of naphthalic acid N-(3-dimethylaminopropyl)imide (1 mol) and 175.5 g of 4,4'-bis-(chloroacetamidophenyl)-methane (0.5 mol) are heated for 3 hours at 100° C. in 1330 g of polyglycol (average molecular weight 400), a clear viscous solution forming initially from which a colourless crystalline precipitate is subsequently deposited. After cooling to room temperature, the reaction mixture is diluted, with stirring, with 3.3 l of isopropanol, the crystalline precipitate is filtered off by suction, washed with isopropanol until the washings are colourless and dried at 60° C. in vacuo. 444 g (97% of theory) of compounds of the formula

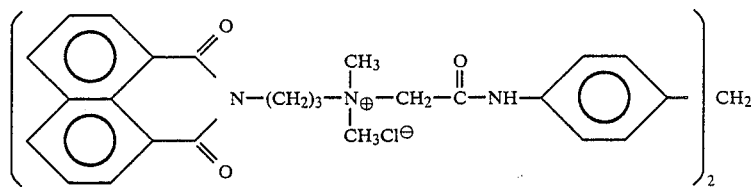

to be obtained.

The substance is virtually pure according to thin-layer chromatography. 1 shows fluorescence quenching on the fluorescing silica plate. Rf value: 0.3 (eluant: 45% by volume of butyl acetate, 33% by volume of glacial acetic acid, 9% by volume of formic acid and 13% by volume of water).

Preparation of a Stable Liquid Formulation 20 g of compound of the formula 1, 15 g of ε-caprolactam and 65 g of ethylene glycol are warmed to 80° C. with stirring, a clear solution resulting. After cooling, this is ready for use. The turbidity point is under −5° C. The solution is stable to storage for at least 6 months at +5° C. to +40° C. It is infinitely miscible with water.

Preparation of the Starting Compounds

A. Naphthalic acid N-(3-dimethylaminopropyl)-imide 258 g of naphthalic acid anhydride are suspended in 1.5 l of toluene, treated initially with 2 g of glacial acetic acid, then dropwise with 133 g of 1-amino-3-dimethylamino-propane with stirring and boiling on the water separator, and boiled for a further 1 hour on the water separator, a total of about 24 ml of water separating off. The mixture is cooled to 90° C., 300 ml of water are added, the 2-phase mixture is stirred under reflux for 30 minutes, the lower aqueous phase is separated from the hot mixture, 6 g of Tonsil and 12 g of activated charcoal are added, the remaining, still absorptive water is removed by azeotropic distillation on the water separator and filtered hot from the clearing agents and the clear toluene solution is evaporated to dryness on the rotary evaporator. 352 g (96% of theory) of naphthalic acid N-(3-dimethylaminopropyl)-imide are obtained as an almost colourless crystalliine powder. Melting point: 117° C., m/e=282 ($M^{61}$).

B. 4,4'-Bis-(Chloroacetamidophenyl)-methane 119 g of 4,4'-diaminodiphenylmethane (0.6 mol) are dissolved in 1.5 l of toluene at 60° C., cooled to room temperature, treated dropwise with stirring with 147 g (1.3 mol) of chloroacetyl chloride, the temperature of the exothermic reaction being allowed to increase to 40° C. and the liberated hydrochloric acid being passed into an alkaline absorption facility. During the reaction, 4,4'-bis-(chloroacetamidophenyl)-methane precipitates from the solution in the form of colourless crystals. The suspension is heated for 2 hours at 105° C. and cooled to room temperature. The crystalline precipitate is filtered off by suction, washed with toluene and dried at 50° C. in vacuo. 208 g (98% of theory) of 4,4'-bis-(chloroacetamidophenyl)-methane are obtained. Melting point: 238° C., m/e=350 ($M^{\oplus}$, 2 Cl).

One-pot Method

The compound of the formula 1 can advantageously also be obtained directly in the form of a stable solution which is ready for use without intermediate isolation of the starting components, by combining the toluene suspensions of the starting compounds prepared, but not isolated, under A. and B., adding 1.8 kg of ethylene glycol and 410 g of ε-caprolactam in place of the polyglycol and distilling off the toluene at 100° C. with the aid of a slight waterjet vacuum during the 3-hour reaction. 2785 g of approximately 20% strength solution of 1 are obtained.

The following compounds are prepared in an analogous fashion:

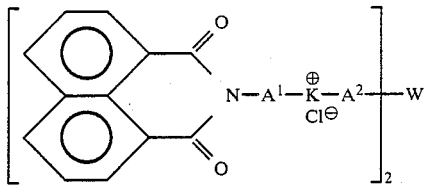

| Example | A¹ | ⊕K⁻ | A² | W |
|---|---|---|---|---|
| 2 | –⟨C₆H₄⟩–CH₂– | –N⁺(CH₃)₃ | –CH₂–CO–NH– | –⟨C₆H₄⟩–SO₂–⟨C₆H₄⟩– |
| 3 | –CH₂–C(CH₃)₂–CH₂– | –N⁺(CH₃)₃ | –CH₂–CO–NH– | –⟨C₆H₄⟩–O–⟨C₆H₄⟩– |
| 4 | –CH₂–CH₂– | –N⁺(CH₂CH₃)₂ | –CH₂–CO–NH– | –⟨cyclohexyl(H,H)⟩–CH₂–⟨cyclohexyl(H,H)⟩– |
| 5 | –CH₂– | pyridinium N⁺ | –CH₂–CO–NH– | –⟨C₆H₄⟩–C(CH₃)₂–⟨C₆H₄⟩– |
| 6 | –CH₂– | imidazolinium (N⁺(CH₃)–CH₂–CH₂–N(CH₃)=C(CH₃)) | –CH₂–CO–NH–CH₂– | –⟨C₆H₄⟩–⟨C₆H₄⟩– |
| 7 | –⟨C₆H₄⟩–CO– | DABCO-type bicyclic N⁺(CH₃) | –CH₂– | –CO– |
| 8 | –⟨C₆H₄⟩–CH₂– | –N⁺(CH₃)₂–CH₂–C₆H₅ | –CH₂–CO–NH– | –⟨C₆H₄⟩– |

-continued
| Example | $A^1$ | $\overset{\oplus}{-K-}$ | $A^2$ | W |
|---|---|---|---|---|
| 9 | $-CH_2-CH_2-$ |  | $-CH_2-CO-$ | 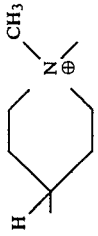 |
| 10 | $-(CH_2)_3-$ | 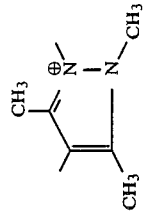 | $-CH_2-SO_2-NH-$ |  |
| 11 | — |  | $-CH_2-CO-O-$ |  |
| 12 | — |  | $-CH_2-CO-NH-$ |  |
| 13 |  |  | $-CH_2-$ |  |
| 14 |  |  | $-CH_2-CO-NH-$ |  |
| 15 |  |  | $-CH_2-CO-$ |  |

-continued

| Example | A¹ | ⊕K— | A² | W |
|---|---|---|---|---|
| 16 | —(CH₂)₂—CO—NH—(CH₂)₃— | —N⊕(CH₃)₂— | —CH₂—CO—NH— | cyclohexyl (H) |
| 17 | —CH₂—CO—NH—CH₂—C(CH₃)₂—CH₂— | —N⊕(CH₃)₂— | —CH₂—CO— | 4-(N-methyl-N-phenylamino)phenyl |
| 18 | —CH₂—CH(CH₃)—(CH₂)₃— | —N⊕(C₂H₅)₂— | —CH₂— | thiophen-2,5-diyl |
| 19 | —CH₂—CO— | N-methylpiperazinium (⊕N(CH₃)—...—N—) | —CH₂— | 2,5-dimethylphenyl |
| 20 | —CO—(CH₂)₂—C₆H₄— | —N⊕(CH₃)(CH₂—CH₂—OH)— | —CH₂—CO—NH— | 3,4'-dimethylbiphenyl |
| 21 | —CO—CH₂—C₆H₄— | pyrrolidinium (⊕N) | —CH₂—CO— | 4-methylphenoxy-4-methylphenyl (diphenyl ether) |
| 22 | —CH₂—C₆H₄—CH₂—CO—NH— | —N⊕(CH₃)₂— | —CH₂—CO—NH— | dimethyl-dibenzothiophene-S,S-dioxide |

-continued

| Example | $A^1$ | $-\overset{\oplus}{K}-$ | $A^2$ | W |
|---|---|---|---|---|
| 23 | $-NH-CO-CH_2-$ | (N-methylmorpholinium) | $-CH_2-CO-NH-$ | bis(4-methylphenylamino)-methoxy-triazine |
| 24 | $-CH_2-$ | (1,2-dimethylbenzimidazolium) | $-CH_2-$ | $-CO-$ |
| 25 | — | (1-methyl-3-methylpyridinium) | $-CH_2-$ | diacetyl-pyrazole |
| 26 | $-(CH_2)_3-CO-NH-(CH_2)_2-$ | $\underset{C_2H_5}{\overset{C_2H_5}{-N^{\oplus}}}-$ | $-CH_2-SO_2-NH-$ | bis(4-methylphenylamino)-(diphenylmethyl-phenyl)-triazine |
| 27 | $-(CH_2)_2-$ | $\underset{\phantom{x}}{\overset{CH_3}{-S^{\oplus}}}-$ | $-CH_2-CO-NH-$ | morpholino-chloro-triazine with 4-methylphenylamino |
| 28 | $-(CH_2)_2-$ | (1,2,4-triazolium) | $-CH_2-CO-NH-$ | bis(azepan-1-yl)-triazine with $-(CH_2)_2-N$ linker |

-continued

| Example | A¹ | ⊕K— | A² | W |
|---|---|---|---|---|
| 29 | —NH—CO—CH₂— | | —CH₂—CO— | piperazine ring (N—N) |
| 30 | —N(CH₃)—CO—CH₂— | —N⁺(CH₃)(nC₄H₉)(CH₃)— | —CH₂—CO—NH— | — |
| 31 | 4-methylphenyl—CO—(CH₂)₃— | —N⁺(CH₃)₂(CH₃)— | —CH₂—CO—NH— | NH—C(=NH)—NH— bridging two 4-methylphenyl groups |
| 32 | —CH₂—CO—O—(CH₂)₂— | —N⁺(CH₃)₂(CH₃)— | —CH₂—CO—NH— | 3,3'-dichlorobiphenyl-4,4'-diyl |
| 33 | 3-methylcyclohexyl—CH₂— | —N⁺(CH₃)₂(CH₃)— | —CH₂—CO—NH— | triazine with three NH-(4-methylphenyl) substituents |
| 34 | —CH₂—CO—NH— | N-methylpyridinium (3-methyl) | —CH₂—CO—NH— | —(CH₂)₂— |
| 35 | — | [—N(H)—C(NH₂)=N(H)—]⁺ₙ | —CH₂— | 4-methylphenyl |

-continued

| Example | A¹ | | A² | W |
|---|---|---|---|---|
| 36 | —(CH₂)₂—N(ring)N—CO—CH₂— | ⊕K— | —CH₂—CO—NH— | (aryl-NH-C(=N(CH₃)₂)-N=C(NH-aryl)) |
| 37 | (phenyl)—NH—CO—CH₂— | CH₃-N⊕(CH₃)- ; morpholinium N⊕-CH₃ | —CH₂—CO— | piperazine —N(ring)N— |
| 38 | —(CH₂)₃—N(CH₃)—CO—CH₂— | CH₃-N⊕(CH₃)- | —CH₂— | 2,5-dimethylthiophene |

The following compounds are also prepared in an analogous fashion:
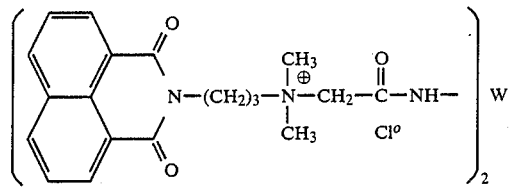
| Example | W |
|---|---|
| 39 | 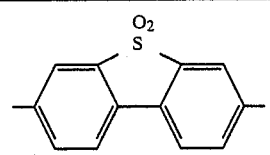 |
| 40 | 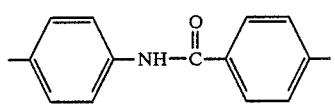 |
| 41 | 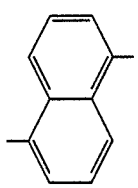 |
| 42 | 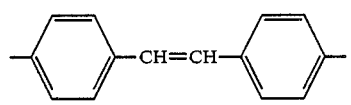 |
| 43 | 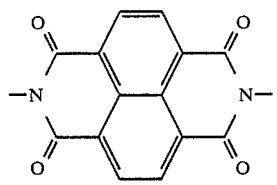 |
| 51 | 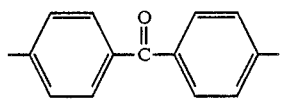 |
| 52 | 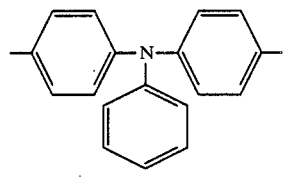 |
| 53 | 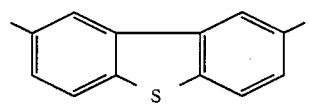 |

-continued
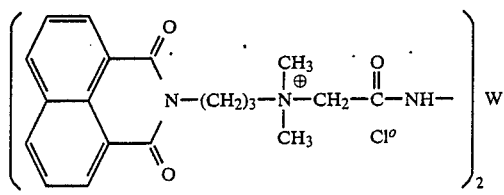
| Example | W |
|---|---|
| 54 | 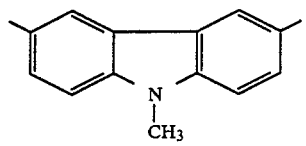 |
| 55 | 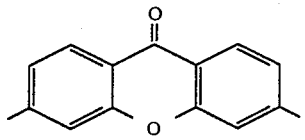 |
| 56 | 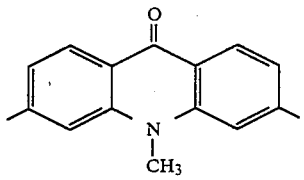 |
| 57 | 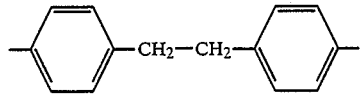 |
| 58 | 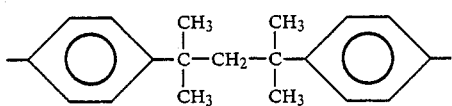 |
| 59 | 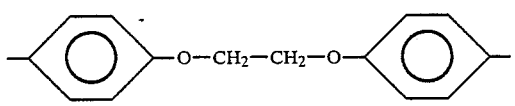 |
| 60 | 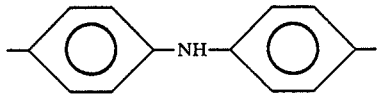 |
| 61 | 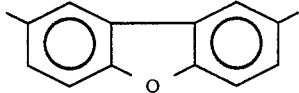 |
| 62 | 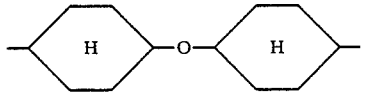 |
| 63 | 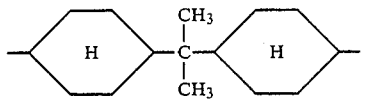 |

-continued
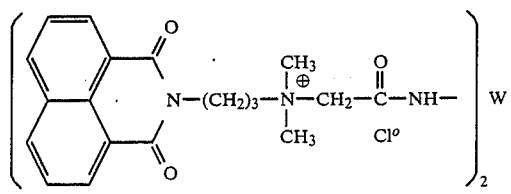
| Example | W |
|---|---|
| 64 |  |
| 65 | 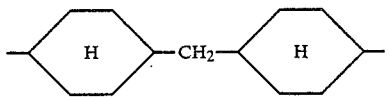 |
| 66 | 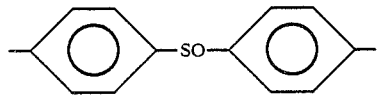 |
| 67 | 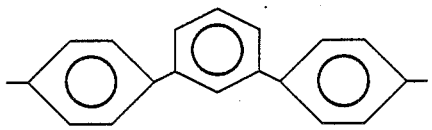 |
| 68 | 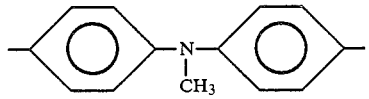 |
| 69 | 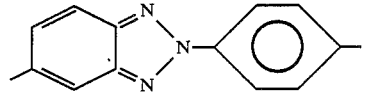 |
| 70 | 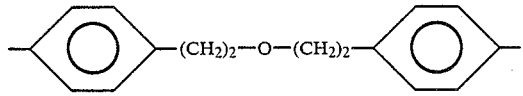 |
| 71 |  |
| 72 | 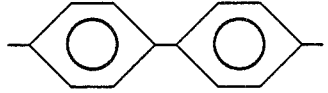 |
| 73 | 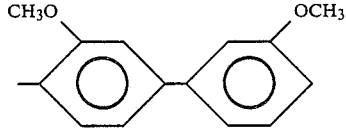 |
| 74 | 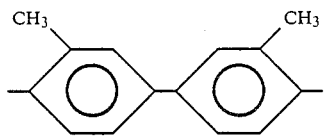 |

-continued
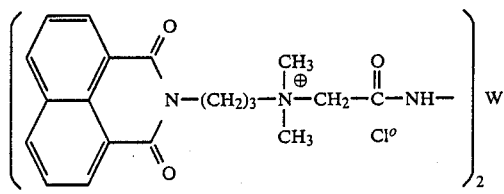
| Example | W |
|---|---|
| 75 | 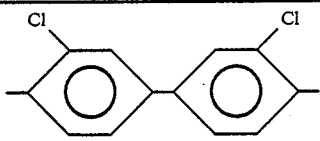 |
| 76 | 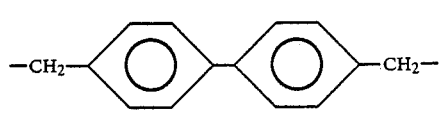 |
| 77 | 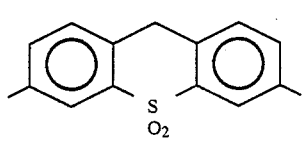 |
| 78 | 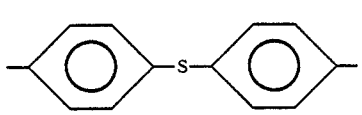 |
| 79 | 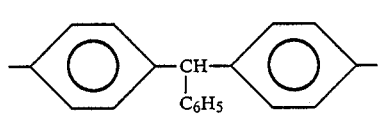 |
| 80 | 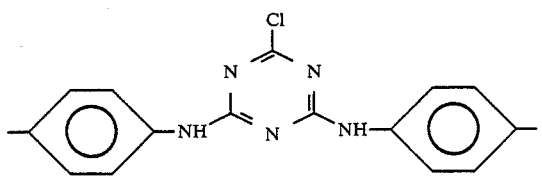 |
| 81 | 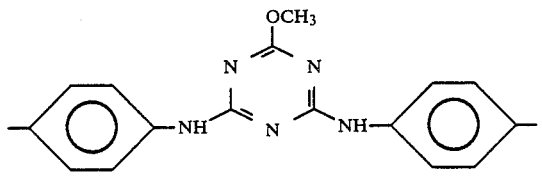 |
| 82 | 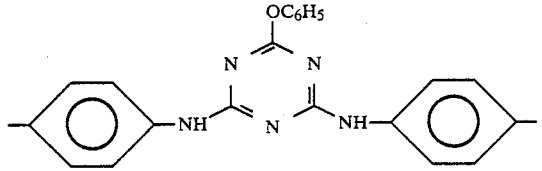 |
| 83 | 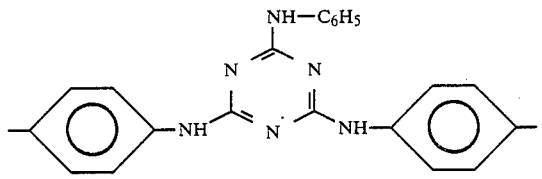 |

-continued
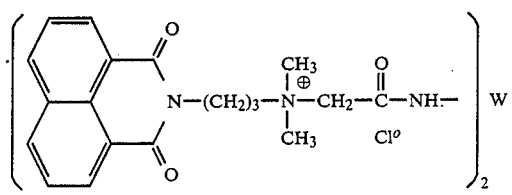
| Example | W |
|---|---|
| 84 | 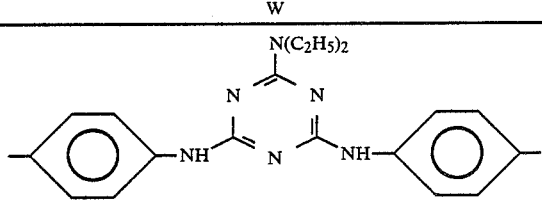 |
| 85 | 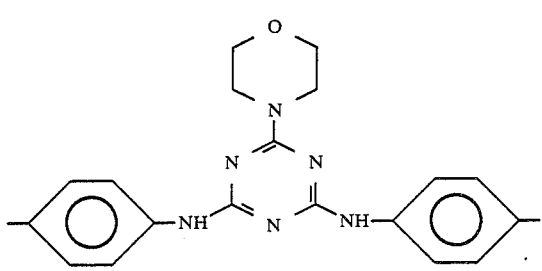 |
| 86 | 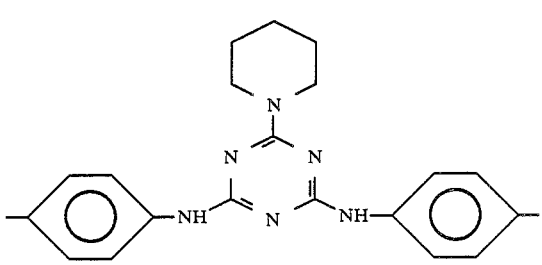 |
| 87 | 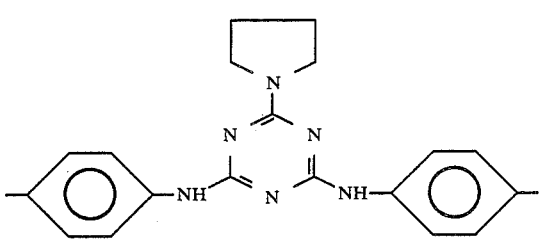 |
| 88 | 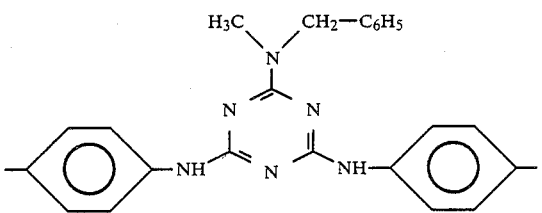 |
| 89 | 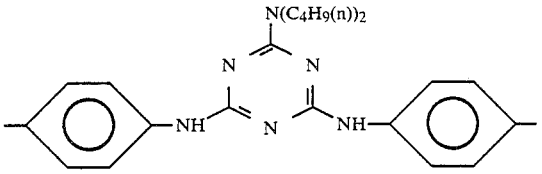 |

-continued
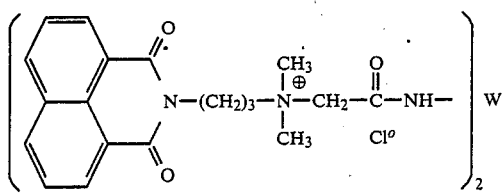
| Example | W |
|---|---|
| 90 | 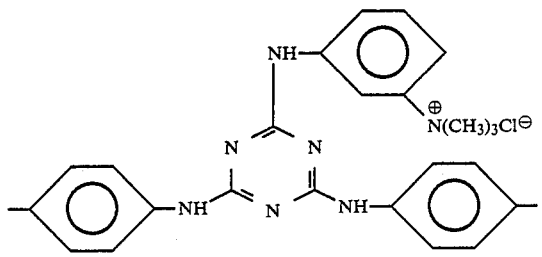 |
| 91 | 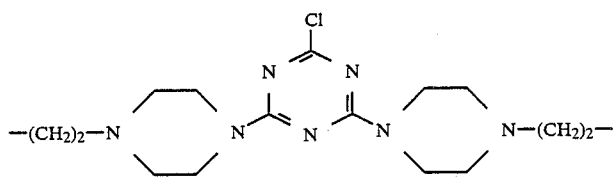 |
| 92 | 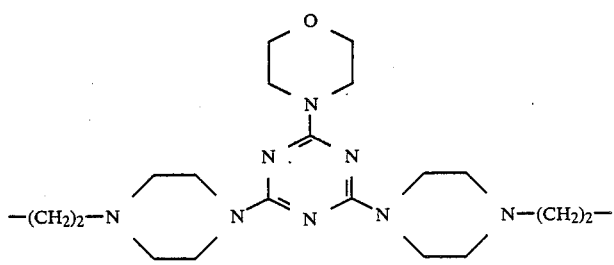 |
| 93 | 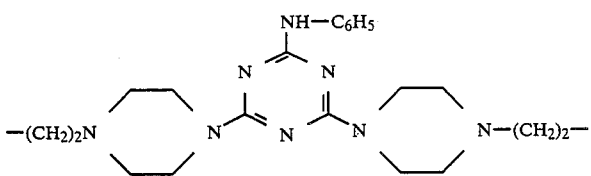 |
| 94 | 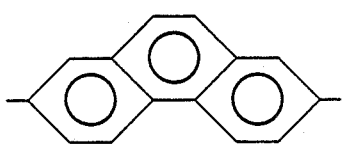 |
| 95 | 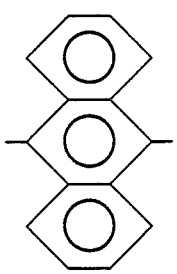 |

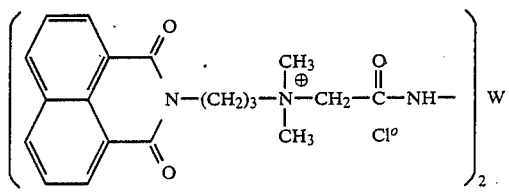
| Example | W |
|---|---|
| 96 |  |
The following compounds are also prepared in an analogous fashion:
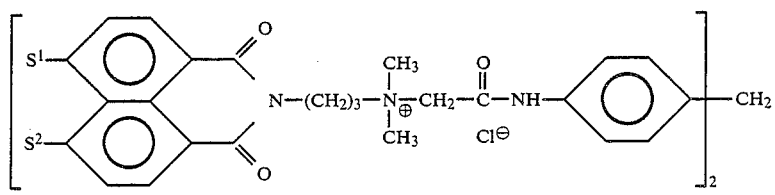
| Example | S¹ | S² |
|---|---|---|
| 97 | Cl | H |
| 98 | Cl | Cl |
| 99 | CH₃—O— | H |
| 100 | C₂H₅—O— | H |
| 101 | CH₃—O— | CH₃—O— |
| 102 | C₆H₅—CH₂—O— | H |
| 103 | C₆H₅—CH₂—O— | C₆H₅—CH₂—O— |
| 104 | C₂H₅—O—CO— | H |
| 105 | C₂H₅—O—CO— | C₂H₅—O—CO— |
| 106 | CH₃—SO₂— | H |
| 107 | Br | H |
| 108 | Br | Br |
| 109 | CH₃—CO—O— | H |
| 110 | C₂H₅—CO—O— | C₂H₅—CO—O— |
| 111 | 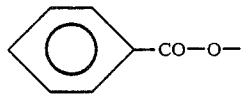 | H |
| 112 | 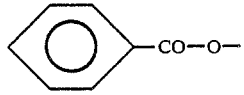 | 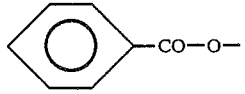 |
| 113 | 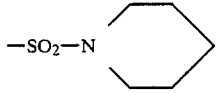 | H |
| 114 | 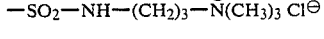 | H |
| 115 |  | H |
| 116 | 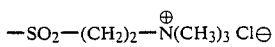 | H |
| 117 | 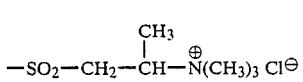 | H |

-continued

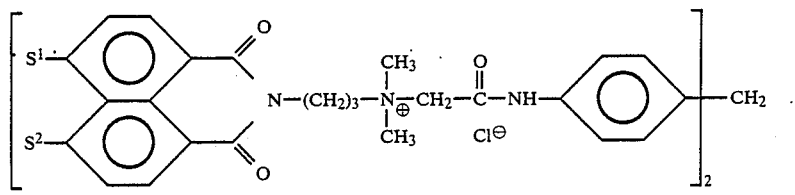

| Example | S¹ | S² |
|---|---|---|
| 118 | 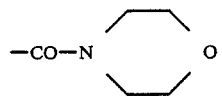 | 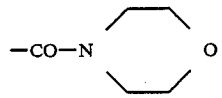 |
| 119 | 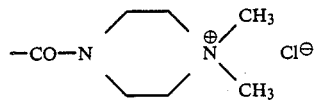 | 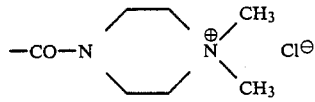 |
| 120 | 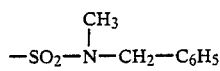 | H |
| 121 | —CO—N(C₄H₉-n)₂ | —CO—N(C₄H₉-n)₂ |
| 122 | —CH₂—NH—CO—CH₂-N⁺(CH₃)₃ Cl⁻ | H |
| 123 | —CH₂—N⁺—(CH₃)₃ Cl⁻ | H |

EXAMPLE 124

85 g of naphthalic acid N-(3-dimethylaminopropyl)imide (0.3 mol) and 52 g of 4,4′,4″-Tris-(chloroacetamidophenyl)-methane (0.1 mol) are heated for 20 hours at 100° C. in 600 g of polyglycol (average molecular weight 400) under nitrogen, a clear solution forming initially from which a colourless crystalline precipitate is deposited subsequently. 1.5 l of acetone are now added at 60° C., and the suspension is cooled to room temperature with stirring. The crystalline precipitate is filtered off by suction, washed with acetone and dried at 60° C. in vacuo. 135 g (98.5% of theory) of compound of the formula

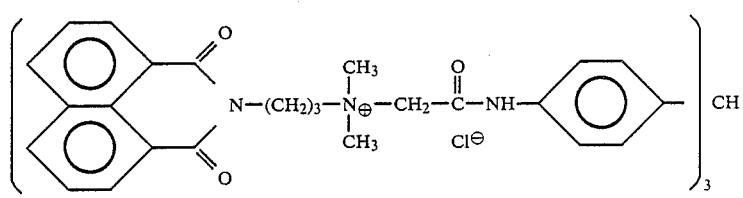

are obtained.

The substance is practically pure according to thin-layer chromatography (silica gel, eluant as for compound 1); RF value: 0.12.

4,4′,4″-Tris-(chloroacetamidophenyl)-methane is accessible analogously to the bis-compound set out in Example 1B. from 4,4′,4″-trisaminophenyl-methane and 3.2 equivalents of chloroacetyl chloride in boiling toluene in 95% yield. Melting point: 240° C.; m/e=517 M+, 3 Cl).

The following compounds are prepared in analogous fashion to compound 124:

| Example | W |
|---|---|
| 125 | 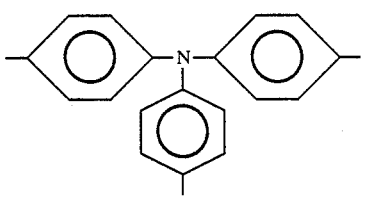 |

| Example | W |
|---|---|
| 126 | 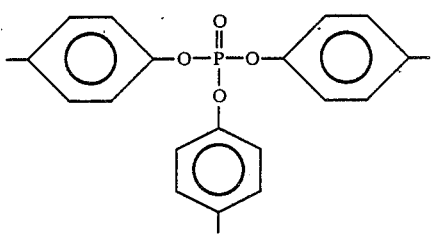 |
| 127 | 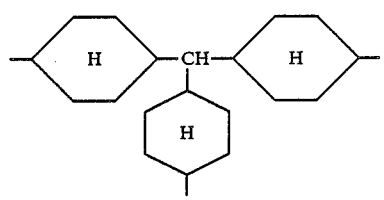 |
| 128 | 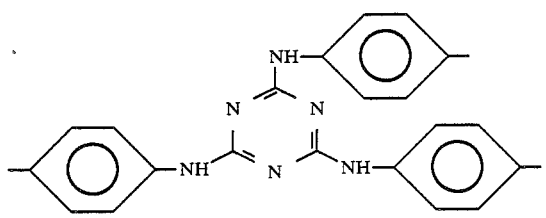 |
| 129 | 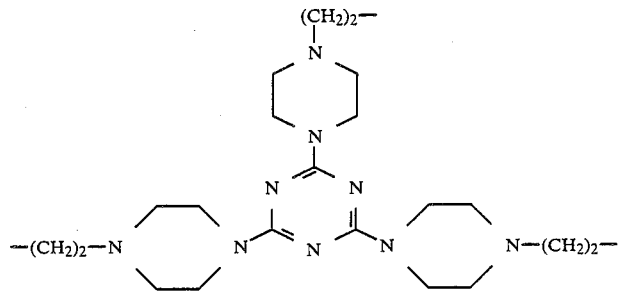 |

EXAMPLE 130

69 g of N-(3-N'-methyl-N'-chloroacetamidopropyl)-naphthalimide (0.2 mol) and 45 g of 4,4'-bis-(3-dimethylaminopropylureidophenyl)-methane (0.1 mol) are heated for 8 hours at 100° C. in 500 g of polyglycol (average molecular weight 400), a solution being obtained which is ready for use and which contains 18.6 per cent by weight of fluorescence quencher of the following formula as active ingredient Preparation of the Starting Compounds

A.

N-(3-N'-Methyl-N'-chloroacetamidopropyl)-naphthalimide 79 g of naphthalic acid anhydride (0.4 mol) are reacted, analogously to Example 1A., on the water separator, with 36 g of 1-amino-3-methylamino-propane (about (0.4 mol) in 500 ml of boiling toluene with addition of 1 ml of glacial acetic acid and worked up. After

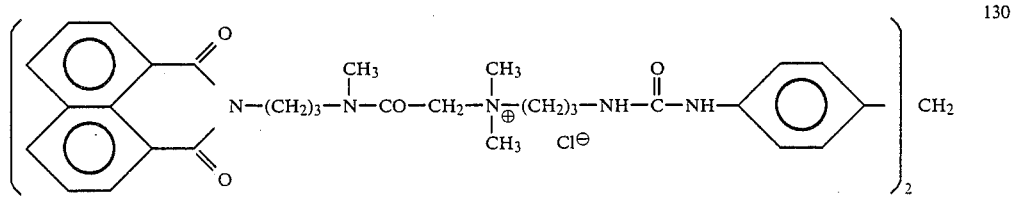

130

The substance is practically pure according to thin-layer chromatography. RF value: 0.19 (eluant as for compound 1).

recrystallization from methyl-cyclohexane, 78 g (73% of theory) of naphthalic acid N-(3-methylaminopropyl)-imide of melting point 108° C.; m/e=268 (M⊕) are obtained.

67 g of naphthalic acid N-(3-methylaminopropyl)-imide (0.25 mol) are treated dropwise in 600 ml of toluene at 20°–40° C. with 29 g of chloroacetyl chloride (0.257 mol) with stirring, heated for 4 hours at 105° C. and cooled to room temperature. The crystalline precipitate is filtered off by suction, washed with toluene and dried at 60° C. in vacuo. 81 g (94% of theory) of N-(3-N'-methyl-N'-chloroacetamidopropyl)-naphthalimide of melting point 152° C.; m/e=344 (M$^\oplus$, Cl) are obtained.

B.
4,4'-Bis-(3-dimethylaminopropylureidophenyl)-methane 25 g of bis-(4-isocyanatophenyl)-methane are dissolved in 250 ml of anhydrouw acetonitrile, treated dropwise with 20.4 g of 1-amino-3-dimethylamino-propane with cooling at 20°–30° C. and stirred for 20 hours at room temperature. The crystalline precipitate is filtered off by suction, washed with acetonitrile and dried at 50° C. in vacuo. 39.8 g (88% of theory) of 4,4'-bis-(3-dimethylaminopropylureidophenyl)-methane of melting point 178° C.; m/e=454 (M$^\oplus$) are obtained.

The following compounds are prepared in an analogous fashion:

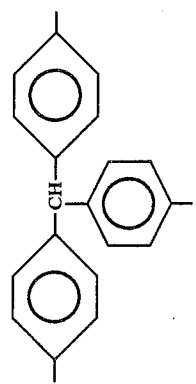
| Example | A¹ | ⊕K— | A² | p | W |
|---------|----|----|----|----|----|
| 131 | —(CH₂)₃—N(CH₃)—CO—CH₂— | —N⁺(CH₃)₂— | —(CH₂)₃—NH—CO—NH— | 3 | 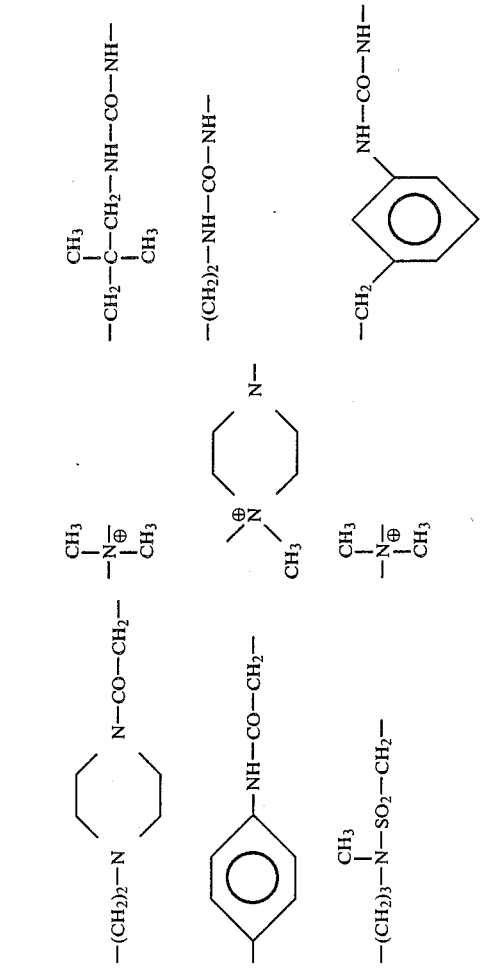 |
| 132 | —(CH₂)₂—N(cyclic)—CO—CH₂— | —N⁺(CH₃)₂— | —CH₂—C(CH₃)₂—CH₂—NH—CO—NH— | 2 | |
| 133 | —C₆H₄—NH—CO—CH₂— | —N⁺(CH₃)(cyclic) | —(CH₂)₂—NH—CO—NH— | 2 | |
| 134 | —(CH₂)₃—N(CH₃)—SO₂—CH₂— | —N⁺(CH₃)₂— | —CH₂—C₆H₃(NH—CO—NH—)— | 2 | |
| 135 | —NH—CO—CH₂— | pyridinium ⊕N— | —CO—NH— | 2 | |

-continued

| Example | A¹ | ⊕K— | p | W |
|---------|-----|-----|---|---|
| 136 | —N(CH₃)—CO—CH₂— | —⊕N(C₂H₅)₂— | 2 | naphthalene |
| 137 | 4-CH₃-C₆H₄—CO—CH₂— | cyclic ⊕N(CH₃)(CH₂)₅N— | — | —(CH₂)₄— |
| 138 | —O—CO—CH₂— | morpholinium ⊕N(CH₃)₂—CH₂CH₂OCH₂CH₂ | 2 | 4,4'-diphenyl ether |
| 139 | 4-CH₃-C₆H₄—NH—CO—CH₂— | —⊕N(C₂H₅)₂— | 2 | 3,4'-biphenyl |
| 140 | —(CH₂)₃—N(CH₃)—CO—CH₂— | —⊕N(CH₃)₂— | 2 | 2,5-thiophene | where A² groups are:
- 136: —(CH₂)₂—NH—CO—NH—
- 137: —CO—NH—
- 138: —(CH₂)₂—NH—CO—NH—
- 139: —(CH₂)₃—CH(CH₃)—NH—SO₂—
- 140: 4-CH₂-C₆H₄—CH₂—NH—CO—

-continued $$\left\{ \begin{array}{c} \text{(naphthalimide)} \\ N-A^1-\overset{\oplus}{K}-A^2-W \end{array} \right\}_p \cdot p \cdot Cl^\ominus$$

| Example | A¹ | ⊕K— | A² | p | W |
|---|---|---|---|---|---|
| 141 | —(CH₂)₃—N(CH₃)—SO₂—CH₂— | H₃C—N⊕(CH₃)—(piperidine)— | — | 2 | 2-chloro-4,6-dimethyl-triazine |
| 142 | (p-phenylene)—NH—CO—CH₂— | H₃C—N⊕(CH₃)—(piperidine)— | — | 3 | 2,4-dimethyl-triazine |
| 143 | —(CH₂)₃—N(CH₃)—CO—CH₂— | pyridinium (N⊕) | —CH₂—NH—CO—NH— | 2 | diphenylmethane (two phenyls with —CH₂—) |
| 144 | (p-phenylene)—CO—CH₂— | —N⊕(CH₃)₂—CH₂—CH₂OH | —CH₂—CO—NH—CH₂— | 2 | biphenyl |
| 145 | —CH₂—CO—CH₂— | —N⊕(CH₃)₃ | —(CH₂)₃—NH—CO—NH— | 2 | cyclohexyl (H) |
| 146 | —(CH₂)₃—N(CH₃)—CO—CH₂—* | *N⊕(imidazolium N—CH₃) | — | 2 | phenyl |

-continued

| Example | A¹ | —⊕K— | —A² | p | W |
|---|---|---|---|---|---|
| 147 | —NH—CO—CH₂—* | 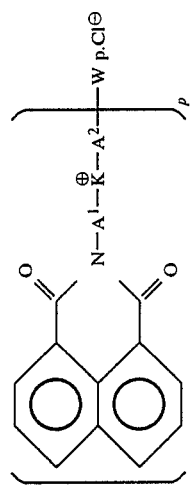 | — | 2 | 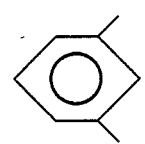 |
| 148 | 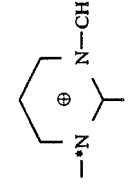 | $\begin{matrix}CH_3\\|\\-N^\oplus-CH_3\\|\\CH_3\end{matrix}$ | <br>—CH₂— | 2 | 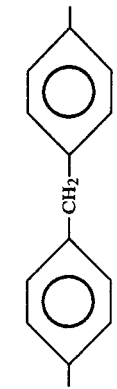 |
| 149 | $\begin{matrix}CH_3\\|\\-CH_2-CO-CH-\end{matrix}$ | $\begin{matrix}CH_3\\|\\-N^\oplus-CH_3\\|\\CH_3\end{matrix}$ | —(CH₂)₃—NH—CS—NH— | 2 | 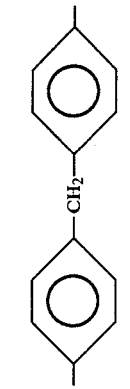 |
| 150 | 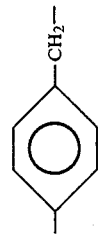—NH—CO—CH₂— | $\begin{matrix}CH_3\\|\\-N^\oplus-CH_3\\|\\CH_3\end{matrix}$ | —(CH₂)₃—NH—CH₂—CO—NH— | 2 | 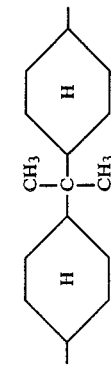 |
| 151 | 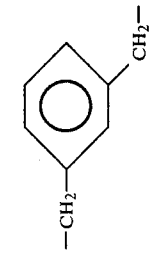 | $\begin{matrix}CH_3\\|\\-N^\oplus-CH_3\\|\\CH_3\end{matrix}$ | $\begin{matrix}CH_3\\|\\-CH_2-C-CH_2-NH-CO-NH-\\|\\CH_3\end{matrix}$ | 2 | 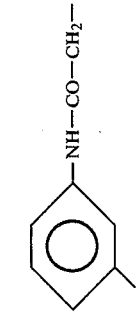 |

-continued
| Example | A¹ | K | p | W |
|---|---|---|---|---|
| 152 | 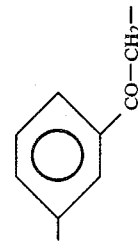—CO—CH₂— | 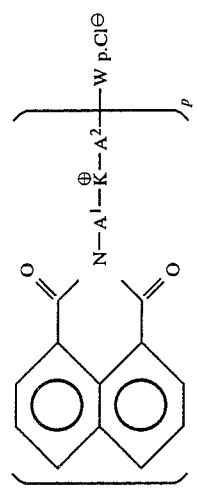⊕K— | 2 | —CO— |
| 153 | —(CH₂)₃—N(CH₃)—CO—CH₂— | —N⊕(CH₃)₂— | 2 | 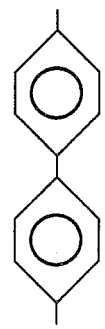 |
| 154 | —CH₂—CO—CH₂— | 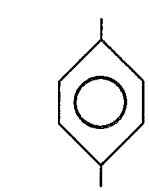 | 2 | 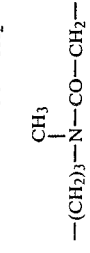 |
|  | | —S⊕(CH₃)— | | |
Row 154 K: —S⊕(CH₃)—
Row 153 W: biphenyl linker
Row 154 A¹: —(CH₂)₂—NH—CO—NH—

The following compounds are also prepared in an analogous fashion:

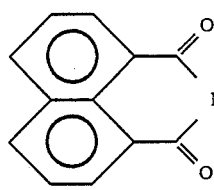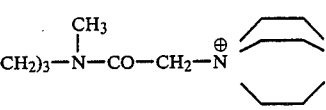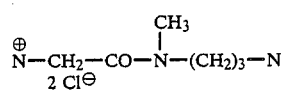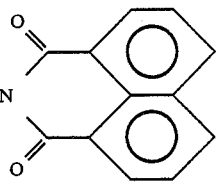

155

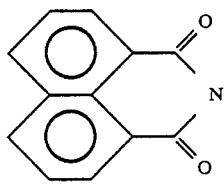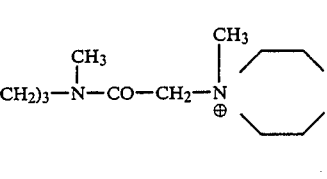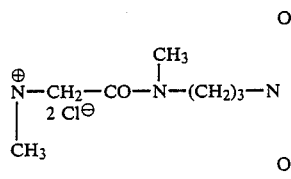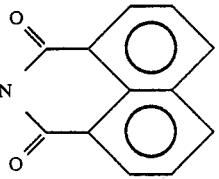

156

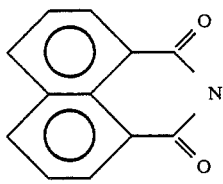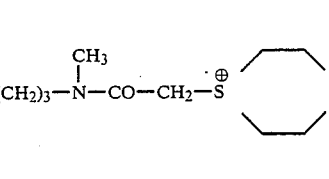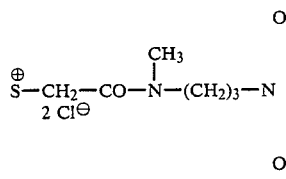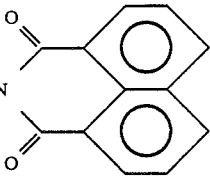

157

EXAMPLE 158

50.5 g of bis-(3-naphthalimido-N-propyl-methylamine (0.1 mol) are treated dropwise in 2 l of water-free chlorobenzene at 70°–75° C. with 10.5 ml of dimethyl sulphate with stirring, stirred for 6 hours at 70°–75° C., cooled to room temperature and stirred for 30 minutes with 1.3 l of acetone. The colourless crystalline precipitate is filtered off by suction, washed with acetone and dried at 40° C. in vacuo. 60 g (95% of theory) of compound of the formula

Preparation of the Starting Material 99 g of naphthalic acid anhydride (0.5 mol) are suspended in 1.3 l of toluene, treated initially with 1.5 g of glacial acetic acid, then dropwise with 36.3 g of bis-(3-aminopropyl)-methylamine (0.25 mol) with stirring and boiling on the water separator, and then boiled for a further 5 hours on the water separator, a total of 9 ml of water separating off. 3 g of activated charcoal and 6 g of Tonsil are added, the suspension is boiled for 20 minutes on the water separator, the hot solution is filtered, and the filtrate is evaporated to dryness on the rotary evaporator. The residue is recrystallized from 600 ml of ethyl-

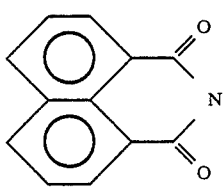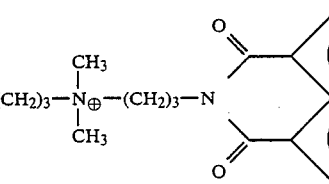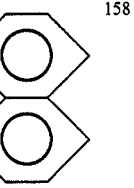

158 are obtained.

The substance is virtually pure according to thin-layer chromatography (silica gel, eluant as for compound 1); RF value: 0.53).

ene glycol monomethyl ether, washed with ethanol and dried at 60° C. in vacuo. 88 g (70% of theory) of bis-(3-naphthalimido-N-propyl)-methylamine of melting point 166° C., m/e=505 (M⊕) are obtained.

The following compounds are prepared analogously to 158.

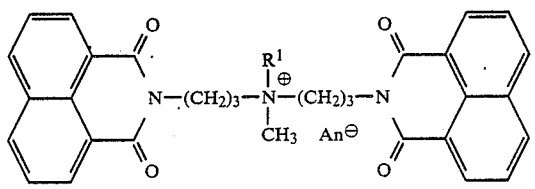
| Example | R¹ | An⊖ |
|---|---|---|
| 159 | C₆H₅—CH₂— | Cl⊖ |
| 160 | benzimidazol-2-yl—CH₂— | Cl⊖ |
| 161 | CH₃O—CO—CH₂— | Br⊖ |
| 162 | C₂H₅— | CH₃—C₆H₄—SO₃⊖ |
| 163 | n-C₄H₉— | Br⊖ |
| 164 | —CH₂—CH₂—OH | CH₃—COO⊖ |
| 165 | 4-Cl—C₆H₄—CH₂— | Cl⊖ |
| 166 | CH₂=CH—CH₂— | Br⊖ |
| 167 | C₆H₅—CO—CH₂— | Cl⊖ |
| 168 | C₆H₅—NH—CO—CH₂— | Cl⊖ |
| 169 | CH₃—(CH₂)₂— | J⊖ |
| 170 | NH₂—CO—CH₂— | Cl⊖ |
| 171 | NC—CH₂— | Cl⊖ |
| 172 | CH₃—CO—CH₂— | Br⊖ |
| 173 | 4-O₂N—C₆H₄—CH₂— | Cl⊖ |
The following compounds are also prepared analogously to 158:
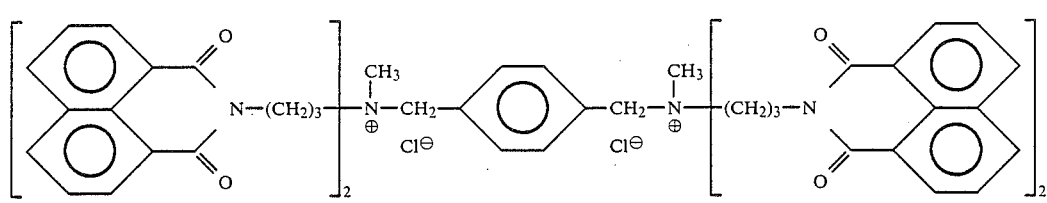
174

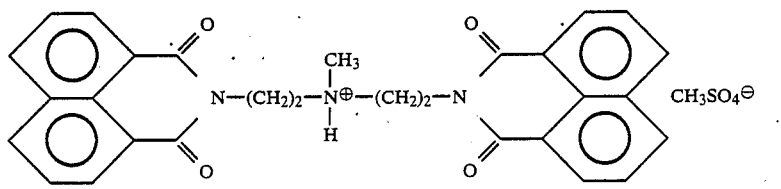

175

(Precursor prepared from 2 naphthalic acid anhydride+diethylenetriamine in place of bis-(3-aminopropyl)-methylamine; colourless crystals, melting point >300° C., m/e=463 (M⊕)).

in the form of almost colourless, high-melting-point crystals are obtained.

EXAMPLE 178

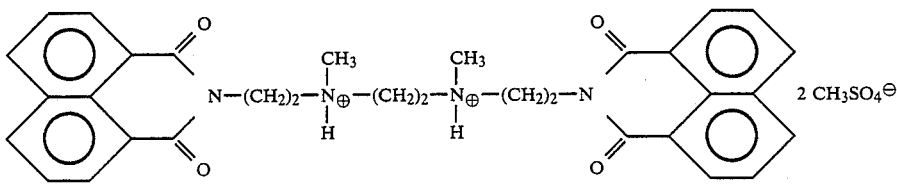

176

2 CH₃SO₄⊖

(Precursor prepared from 2 naphthalic acid anhydride+triethylenetriamine in place of bis-(3-aminopropyl)-methylamine; colourless crystals, melting point >300° C., m/e=506 (M⊕)).

EXAMPLE 177

50.6 g of N,N'-bis-(2-naphthalimido-N''-ethyl)-diamino-ethane (0.1 mol, prepared from 2 naphthalic acid anhydride+triethylenetetramine) and 15 g of acetimino ethyl ether hydrochloride (0.12 mol) are boiled for 2 hours in 300 ml of acetonitrile. After cooling, the crystalline precipitate is filtered off by suction, washed with acetone and dried at 50° C. in vacuo. 56 g (99% of theory) of compound of the formula 0.1 mol of compound of the formula 176, in the form of the free base, are reacted with 43 ml of dimethyl sulphate in 2 l of chlorobenzene at 70°–75° C. (6 hours) analogously to Example 158, but with addition of 0.25 mol of triisopropanolamine as proton scavenger. After addition of 1.3 l of acetone, the colourless, crystalline substance is isolated. Yield 93% of theory. It corresponds to the formula

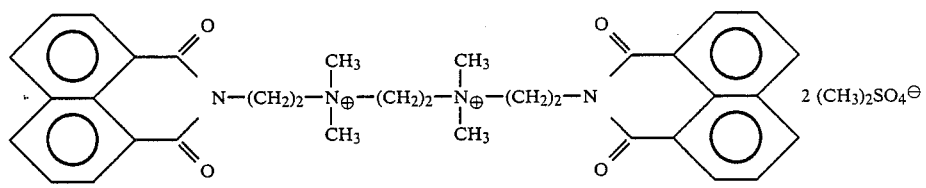

178

2 (CH₃)₂SO₄⊖

Colourless, easily water-soluble, high-melting-point crystals.

EXAMPLES 179–192

The following compounds are prepared analogously to Example 130, but using the respective starting components in the molar ratio 1:1:

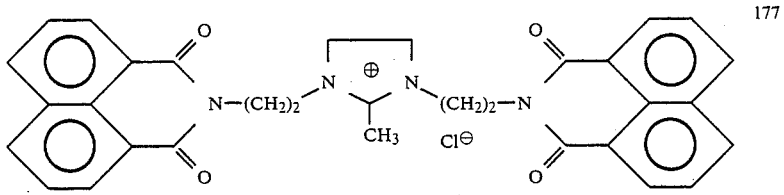

177

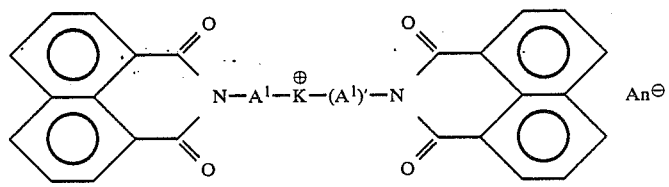

| Example | —A¹— | $\overset{\oplus}{-K-}$ | —(A¹)'— | An⊖ |
|---|---|---|---|---|
| 179 | —NH—CO—CH₂— | $-\overset{\oplus}{N}$⟨pyridinium⟩ | —CH₂— | Cl⊖ |
| 180 | $-\overset{CH_3}{N}-CO-CH_2-$ | $-\overset{CH_3}{\underset{CH_3}{\overset{\|}{N}^{\oplus}}}-$ | $-CH_2-\overset{CH_3}{\underset{CH_3}{\overset{\|}{C}}}-CH_2-$ | Cl⊖ |
| 181 | —⟨C₆H₄⟩—CO—CH₂— | $-\overset{CH_3}{\underset{CH_3}{\overset{\|}{N}^{\oplus}}}-$ | —CH₂—⟨C₆H₄(CH₃)⟩— | Br⊖ |
| 182 | —(CH₂)₂—N⟨piperazine⟩N—CO—CH₂— | $-\overset{CH_3}{\underset{CH_3}{\overset{\|}{N}^{\oplus}}}-$ | —⟨C₆H₃(CH₃)₂⟩— | Cl⊖ |
| 183 | —⟨C₆H₄⟩—NH—CO—CH₂— | $-\overset{\oplus}{N}\underset{CH_3}{\diagdown}$ ... N— (diazabicyclic) | —CO—CH₂— | Cl⊖ |
| 184 | $-(CH_2)_3-\overset{CH_3}{\overset{\|}{N}}-SO_2-CH_2-$ | piperidinium ($-\overset{\oplus}{N}-$) | —(CH₂)₂— | Cl⊖ |
| 185 | —⟨C₆H₄(CH₃)⟩—CH₂— | $-\overset{CH_3}{\underset{\oplus}{\overset{\|}{S}}}-$ | —(CH₂)₂— | Cl⊖ |
| 186 | —⟨C₆H₄(CH₃)⟩—CO—CH₂— | $-\overset{CH_3}{\underset{CH_3}{\overset{\|}{N}^{\oplus}}}-$ | —(CH₂)₃—NH—CO—(CH₂)₂— | Cl⊖ |
| 187 | —CH₂—CO—CH₂— | N-methylimidazolium | —CH₂— | Br⊖ |
| 188 | $-(CH_2)_3-\overset{CH_3}{\overset{\|}{N}}-CO-CH_2-$ | $-\overset{CH_3}{\underset{CH_3}{\overset{\|}{N}^{\oplus}}}-$ | $-CH_2-CO-\overset{CH_3}{\overset{\|}{N}}-(CH_2)_3-$ | Cl⊖ |

-continued

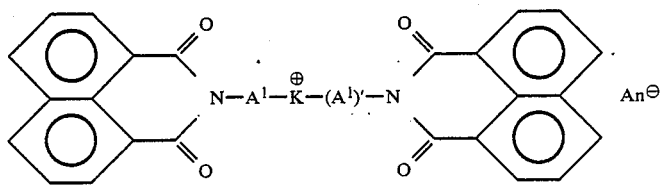

| Example | —A¹— | —K⊕— | —(A¹)'— | An⊖ |
|---|---|---|---|---|
| 189 | ⌬-NH—CO—CH₂— | —N⁺(CH₃)(CH₂—C₆H₅)— | —CH₂—CO—NH-⌬ | Cl⊖ |
| 190 | —(CH₂)₃—N(CH₃)—CO—CH₂— | N-methylpyridinium⊕ | — | Cl⊖ |
| 191 | —NH—CO—CH₂— | N-methylmorpholinium⊕ | —CH₂—CO—N(piperazine)N—(CH₂)₂— | Cl⊖ |
| 192 | —(CH₂)₃—N(CH₃)—CO—CH₂— | —N⁺(CH₃)(CH₃)— | —(CH₂)₃— | Cl⊖ |

EXAMPLE 193

43.6 g of naphthalene-1,4,5,8-tetracarboxylic acid N,N'-bis-(3-dimethylaminopropyl)-diimide (0.1 mol) and 33 g of 4-chloro-benzyl chloride (about 0.2 mol) are refluxed for 20 hours in 1 l of acetonitrile. After cooling, the colourless crystalline precipitate is filtered off by suction, washed with acetonitrile and dried at 50° C. in vacuo. 73.8 g (97% of theory) of compound of the formula

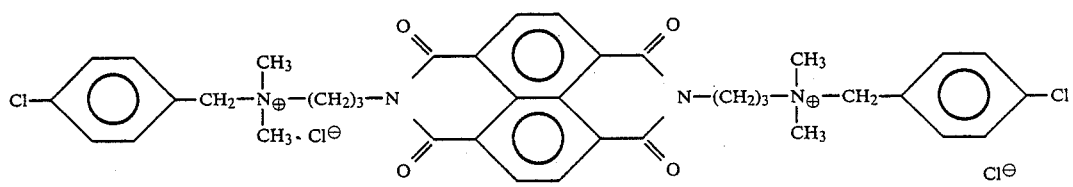

are obtained as a practically colourless crystalline powder.

The substance is virtually pure according to thin-layer chromatography (silica gel, eluant as for compound 1). RF value: 0.22.

Preparation of the Starting Compound 304 g of naphthalene-1,4,5,8-tetracarboxylic acid are refluxed for 15 minutes in 1 l of dimethylformamide and cooled. The crystalline precipitate is filtered off by suction, washed with ethanol and dried at 50° C. in vacuo. 235 g (about 88% of theory) of pure naphthalene-1,4,5,8-tetracarboxylic acid dianhydride are obtained. Melting point: >300° C.; m/e=268 (M+).

53.6 g of naphthalene-1,4,5,8-tetracarboxylic acid dianhydride (0.2 mol) are suspended in 1 l of toluene, treated initially with 2 g of glacial acetic acid, then dropwise with 41 g of 1-amino-3-dimethylaminopropane (0.4 mol) with stirring and boiling on the water separator and boiled for a further 2 hours on the water separator, a total of about 7 ml of water separating off. During the reaction, the reaction product dissolves apart from slight impurities. The mixture is filtered hot and the filtrate cooled. The crystalline precipitate is filtered off by suction, washed with a little toluene and dried at 50° C. in vacuo. 72 g (about 83% of theory) of naphthalene-1,4,5,8-tetracarboxylic acid, N,N'-bis-(3-dimethylaminopropyl)-diimide are obtained as a gold-yellow crystalline powder with metallic lustre and melting point 227° C.: m/e=436 (M⊕).

The following compounds are prepared analogously to 193:

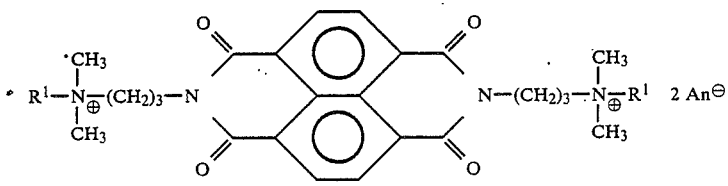
| Example | R¹ | An⊖ |
|---|---|---|
| 194 | 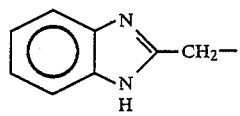 | Cl⊖ |
| 195 | 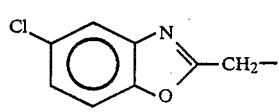 | Cl⊖ |
| 196 | 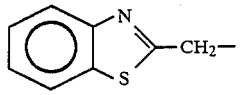 | Cl⊖ |
| 197 |  | Cl⊖ |
| 198 |  | Cl⊖ |
| 199 |  | Cl⊖ |
| 200 | 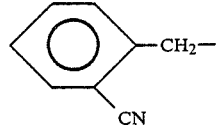 | Cl⊖ |
| 201 | 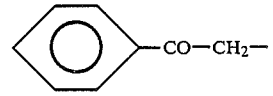 | Br⊖ |
| 202 | 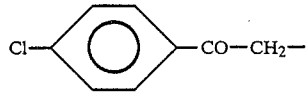 | Cl⊖ |
| 203 | 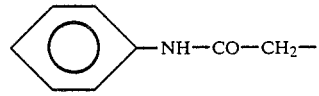 | Cl⊖ |
| 204 | 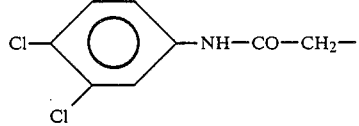 | Cl⊖ |

-continued $$R^1-\overset{CH_3}{\underset{CH_3}{N^\oplus}}-(CH_2)_3-N-CO-\text{[naphthalene-1,2,5,6-tetrayl]}-CO-N-(CH_2)_3-\overset{CH_3}{\underset{CH_3}{N^\oplus}}-R^1 \quad 2\,An^\ominus$$

| Example | R¹ | An⊖ |
|---------|-----|-----|
| 205 | O₂N—C₆H₄—CH₂— | Cl⊖ |
| 206 | CH₃OOC—C₆H₄—NH—CO—CH₂— | Cl⊖ |
| 207 | C₆H₅—CH(CH₃)— | Br⊖ |
| 208 | C₆H₅—(CH₂)₃— | Br⊖ |
| 209 | (2-thienyl)—CH₂— | Cl⊖ |
| 210 | C₆H₅—C₆H₄—CO—CH₂— | Br⊖ |
| 211 | CH₃—CO—CH₂— | Br⊖ |
| 212 | HO—(CH₂)₂— | CH₃—COO⊖ |
| 213 | CH₃— | CH₃SO₄⊖ |
| 214 | C₂H₅— | I⊖ |
| 215 | CH₂=CH—CH₂— | Br⊖ |
| 216 | H₂N—CO—CH₂— | Cl⊖ |
| 217 | NC—CH₂— | Cl⊖ |
| 218 | C₂H₅OCO—CH₂— | Br⊖ |
| 219 | HOOC—CH₂— | Cl⊖ |
| 220 | n-C₃H₇— | I⊖ |
| 221 | n-C₄H₉— | Br⊖ |
| 222 | Cl—(CH₂)₃— | Br⊖ |
| 223 | CH₃O—(CH₂)₂— | Br⊖ |
| 224 | H₂N—CO—CH₂—CH₂— | CH₃COO⊖ |
| 225 | NC—C₆H₄—CH₂— and C₆H₄(CN)—CH₂— (mixture) | Cl⊖ |
| 226 | 4-Br—C₆H₄—CO—CH₂— | Br⊖ |

-continued $$R^1-\overset{CH_3}{\underset{CH_3}{\overset{|}{N}}}-(CH_2)_3-N\underset{O}{\overset{O}{\underset{||}{\overset{||}{C}}}}\text{(naphthalene diimide core)}\underset{O}{\overset{O}{\underset{||}{\overset{||}{C}}}}N-(CH_2)_3-\overset{CH_3}{\underset{CH_3}{\overset{|}{N}}}-R^1 \quad 2\,An^\ominus$$

| Example | R¹ | An⊖ |
|---|---|---|
| 227 | CH₃— | CH₃—C₆H₄—SO₃⊖ |
| 228 | CH₃— | CH₃—P(=O)(OCH₃)—O⊖ |
| 229 | C₆H₁₁— (cyclohexyl) | Br⊖ |
| 230 | naphthyl—CH₂— | Cl⊖ |
| 231 | HOCH₂—CH(OH)—CH₂— | CH₃COO⊖ |

The following compounds are also prepared analogously to 193:

$$E^\oplus-A^3-N\underset{O}{\overset{O}{\underset{||}{\overset{||}{C}}}}\text{(naphthalene diimide core)}\underset{O}{\overset{O}{\underset{||}{\overset{||}{C}}}}N-A^3-E^\oplus \quad 2\,An^\ominus$$

| Example | E⊕— | —A³— | An⊖ |
|---|---|---|---|
| 232 | Cl—C₆H₄—CH₂—N⁺(CH₃)₂— | —CH₂—C₆H₄— | Cl⊖ |
| 233 | CH₃—C₆H₄—CH₂—N⁺(CH₃)₂— | —CH₂—C₆H₄— (meta) | Cl⊖ |
| 234 | C₆H₅—CH₂—⁺N(pyridinium)— | —CH₂— | Cl⊖ |
| 235 | (C₂H₅)₃N⊕— | —(CH₂)₂— | Cl⊖ |

-continued
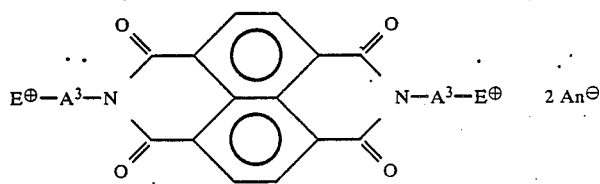
| Example | E⊕— | —A³— | An⊖ |
|---|---|---|---|
| 236 | 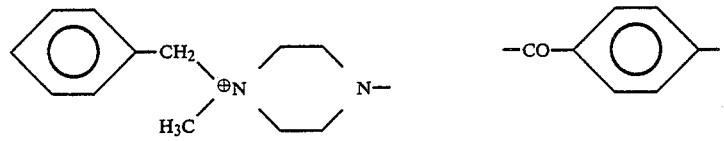 | —CO—⬡— | Cl⊖ |
| 237 | 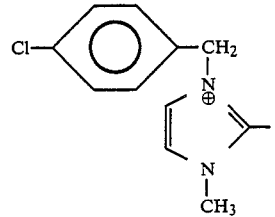 | —CH₂— | Cl⊖ |
| 238 | 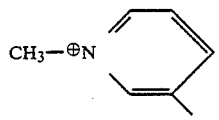 | — | CH₃SO₄⊖ |
| 239 | 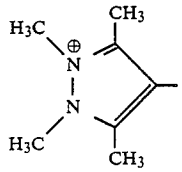 | — | CH₃SO₄⊖ |
| 240 | 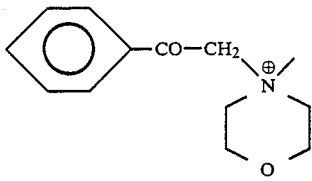 | —(CH₂)₂— | Br⊖ |
| 241 | 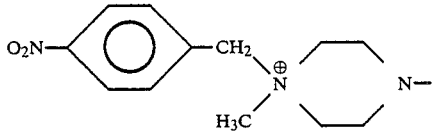 | (CH₂)₂—NH—CO—CH₂— | Cl⊖ |
| 242 | 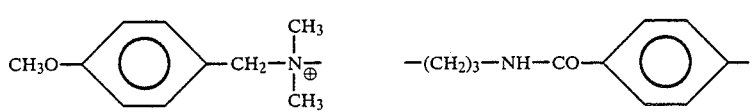 | —(CH₂)₃—NH—CO—⬡— | Cl⊖ |
| 243 | 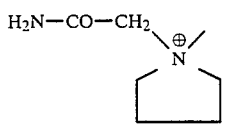 | 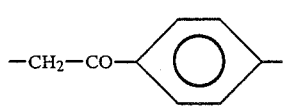 | Cl⊖ |

-continued
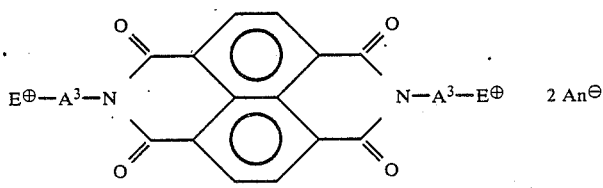
| Example | E⊕— | —A³— | An⊖ |
|---|---|---|---|
| 244 | 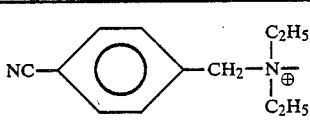 | —(CH₂)₃—CH(CH₃)— | Cl⊖ |
| 245 | 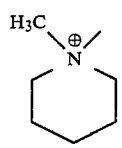 | —(CH₂)₃— |  |
| 246 | 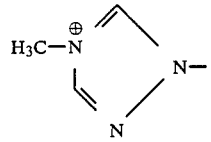 | 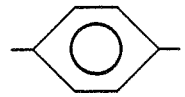 | I⊖ |
| 247 | 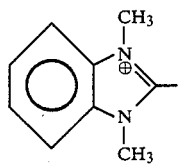 |  | CH₃SO₄⊖ |
| 248 | 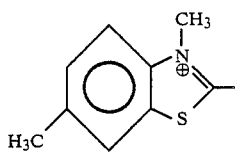 | 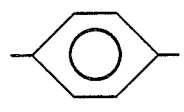 | I⊖ |
| 249 | 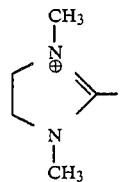 | —(CH₂)₂— | CH₃SO₄⊖ |
| 250 | 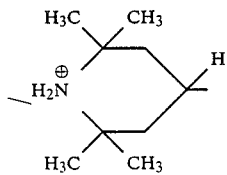 | — | 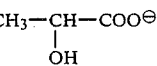 |
| 251 | 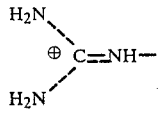 | — | HSO₄⊖ |

-continued

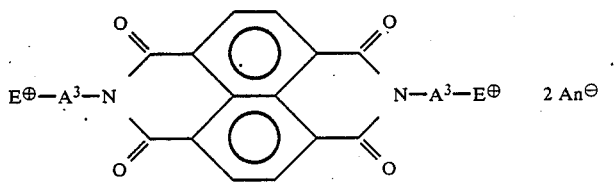

| Example | $E^\oplus-$ | $-A^3-$ | $An^\ominus$ |
|---|---|---|---|
| 252 | 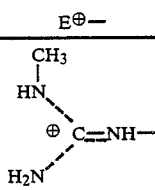 | — | $CH_3SO_4^\ominus$ |
| 253 | 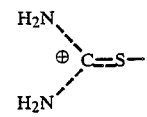 | $-CH_2-\overset{O}{\underset{\|}{C}}-NH-$ | $Cl^\ominus$ |
| 254 | 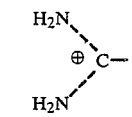 | 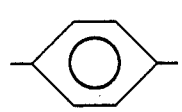 | $NO_3^\ominus$ |
| 255 | 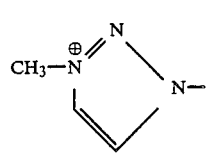 | 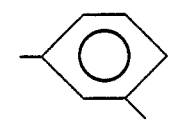 | $I^\ominus$ |
| 256 | $(CH_3)_3N^\oplus-$ | 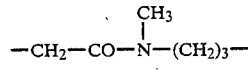 | $CH_3SO_4^\ominus$ |
| 257 | 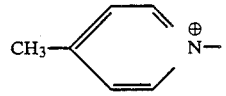 | $-CH_2-CO-\underset{\underset{CH_3}{\|}}{N}-(CH_2)_3-$ | $Cl^\ominus$ |
| 258 | 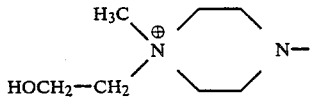 | $-SO_2-$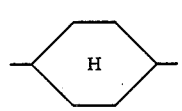 | $Br^\ominus$ |
| 259 | $(CH_3)_3N^\oplus-$ | 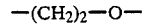 H | $I^\ominus$ |
| 260 | 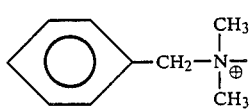 | $-(CH_2)_2-O-$ | $Cl^\ominus$ |

EXAMPLE 261

43.6 g of naphthalene-1,4,5,8-tetracarboxylic acid N,N′-bis-(3-dimethylaminopropyl)-diimide (0.1 mol) and 35 g of 4,4′-bis-(chloroacetamidophenyl)-methane (0.1 mol), preparation see Example 1) are refluxed for 20 hours in 1 l of acetonitrile. After cooling, the crystalline precipitate is filtered off by suction, washed with acetonitrile and dried at 50° C. in vacuo. 76 g (about 97% of theory) of a high molecular weight compound with repeating structural units of the formula

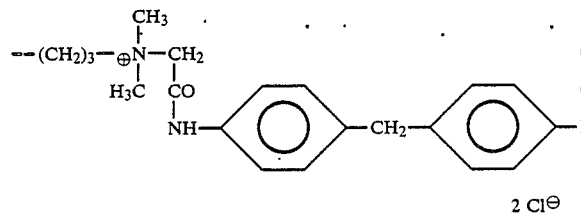
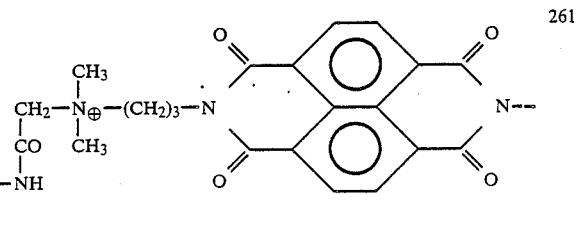
261
are obtained as a high-melting-point, almost colourless, water-soluble crystalline powder. The substance is virtually free from starting components (silica gel, eluant as for compound 1) according to thin-layer chromatography. RF value about 0.
High molelcular weight compounds with the following repeating structural units are prepared in analogous fashion:

| Example | $-\overset{\oplus}{K^1}-$ | $-A^3-$ | $-A^4-$ | $-W^1-$ | $An^\ominus$ |
|---|---|---|---|---|---|
| 262 | (see structure below) | | | | $Cl^\ominus$ |
| 263 | $CH_3-\overset{\|}{\underset{\|}{\overset{\oplus}{N}}}-CH_3$ | $-(CH_2)_3-$ | $-CH_2-CO-NH-$ | H (cyclohexyl) | $Cl^\ominus$ |
| 264 | $C_2H_5-\overset{\|}{\underset{\|}{\overset{\oplus}{N}}}-C_2H_5$ | $-(CH_2)_2-$ | $-CH_2-SO_2-NH-$ | 4,4′-dimethoxybiphenyl | $Cl^\ominus$ |
| 265 | (N-methyl piperidinium with N—) | $-CO-CH_2-$ | $-CH_2-CO-NH-$ | diphenyl sulfone (dimethyl) | $Cl^\ominus$ |
| 266 | (N,N-dimethyl morpholinium) | $-(CH_2)_2-$ | $-CH_2-CO-O-$ | 4,4′-isopropylidenediphenyl | $Cl^\ominus$ |

Example 262:

$-A^3-\overset{\oplus}{K^1}-A^4-W^1-A^4-\overset{\oplus}{K^1}-A^3-N\begin{pmatrix}\text{naphthalene diimide}\end{pmatrix}$ 2 $An^\ominus$

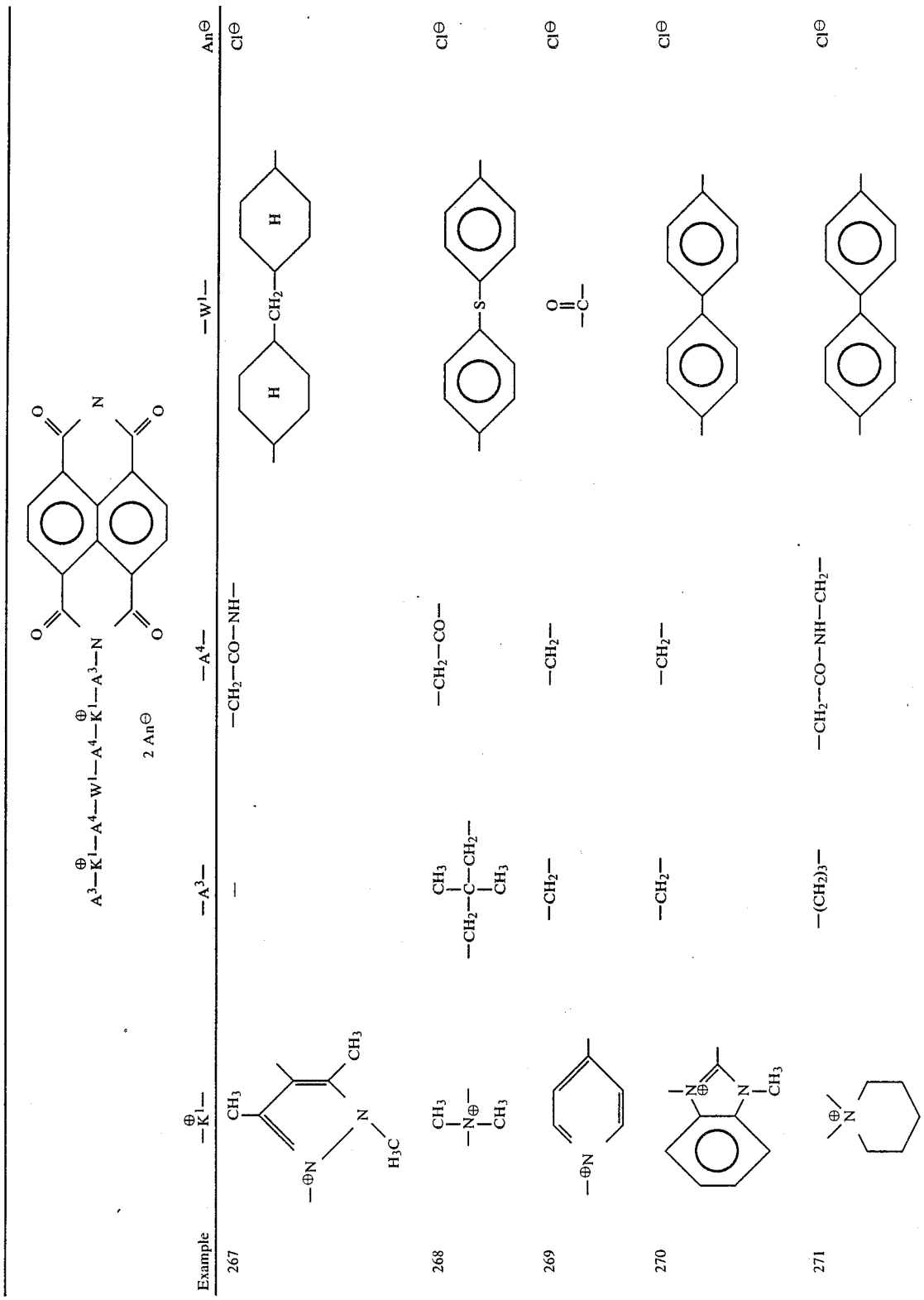

-continued

| Example | $-\overset{\oplus}{K^1}-$ | $-A^3-$ | $-A^4-$ | $-W^1-$ | $An^\ominus$ |
|---|---|---|---|---|---|
| 272 | \* | \* | \* | \* | $Cl^\ominus$ |
| 273 | N-methyl piperidinium with CH₃ | — | —CH₂— | thiophene-like S ring | $Cl^\ominus$ |
| 274 | N,N-dimethyl pyrrolidinium | —CH₂—CO—CH₂— | —CH₂—CO— | diazocane (N...N ring) | $Cl^\ominus$ |
| 275 | $CH_3-\overset{\oplus}{N}-CH_2-C_6H_5$ | —CH₂—CO— (with phenyl) | —CH₂—CO—NH— | 4,4'-sulfonyldiphenyl (tolyl-SO₂-tolyl) | $Br^\ominus$ |
| 276 | $CH_3-\overset{\oplus}{N}-CH_2-CH_2OH$ | —CH₂— (with phenyl) | —CH₂— | tolyl | $Cl^\ominus$ |
| 277 | $CH_3-\overset{\oplus}{N}-CH_2-CH_2OCH_3$ | $-(CH_2)_3-\overset{CH_3}{N}-CO-CH_2-$ | —CH₂—CO—NH— | N,O-heterocycle (oxazole-like) | $Cl^\ominus$ |

Example 272: $A^3-\overset{\oplus}{K^1}-A^4-W^1-A^4-\overset{\oplus}{K^1}-A^3-N$ (naphthalene-1,4,5,8-tetracarboximide-type structure), 2 $An^\ominus$ Example 272 $-K^1-$: N-methylpyridinium (3-methyl)

-continued $$A^3-\overset{\oplus}{K^1}-A^4-W^1-A^4-\overset{\oplus}{K^1}-A^3-N\begin{pmatrix}...\end{pmatrix}$$

2 An⁻

| Example | —K¹⁺— | —A³— | —A⁴— | —W¹— | An⁻ |
|---|---|---|---|---|---|
| 278 | $CH_3$-N⁺($CH_3$)- | 2,4-dimethylphenylene | —$CH_2$— | 2,4-dimethylphenylene | Cl⁻ |
| 279 | $CH_3$-S⁺- | —$(CH_2)_2$— | —$CH_2$—CO—NH— | 4,4'-diphenyl ether (p-tolyl-O-p-tolyl) | Cl⁻ |
| 280 | $CH_3$-N⁺($NH_2$)- | 4-($CH_2$)-phenyl | —$CH_2$— | —CO— | Cl⁻ |
| 281 | imidazolinium ($CH_3$) | —$(CH_2)_2$— | —$CH_2$—CO—NH— | 4,4'-diphenyl sulfide (p-tolyl-S-p-tolyl) | Cl⁻ |
| 282 | $CH_3$-N⁺($CH_3$)- | —$(CH_2)_3$— | —$CH_2$—CO—NH— | chloro-triazine bis(p-tolyl-NH-) | Cl⁻ |

-continued
| Example | $-\overset{\oplus}{K^1}-$ | $-A^3-$ | $-A^4-$ | $-W^1-$ | $An^\ominus$ |
|---|---|---|---|---|---|
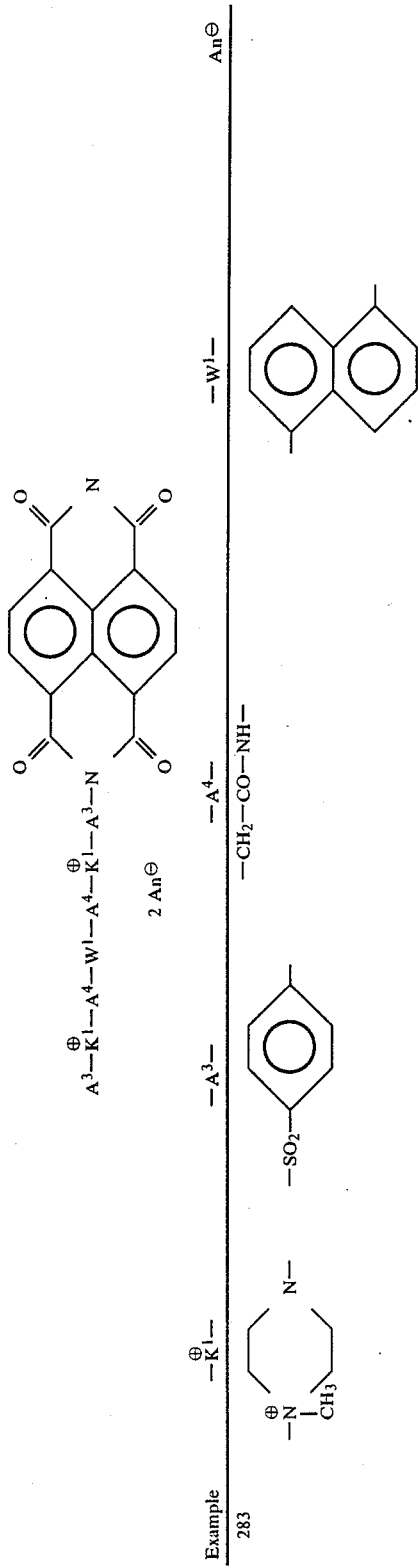

EXAMPLE 284

53.6 g of naphthalene-1,4,5,8-tetracarboxylic acid dianhydride (0.2 mol) are suspended in 400 ml of glacial acetic acid, treated dropwise with 29 g of bis-(3-aminopropyl)-methylamine (0.2 mol) with stirring, boiled for 5 hours with removal by distillation of about 135 ml of acetic acid, cooled at 60° C. and stirred with 650 ml of acetone. The crystalline precipitate is filtered off by suction, washed with acetone and dried at 70° C. in vacuo. 86.5 g (99% of theory) of a high molecular weight compound with repeating structural units of the formula

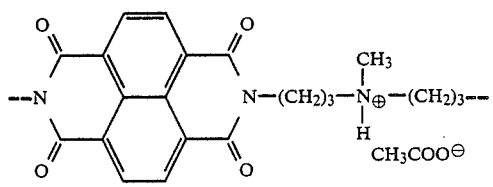

284 are obtained in the form of practically colourless, water-soluble, high-melting-point crystals, which is virtually free from starting components (silica gel, eluant as for compound 1) according to thin-layer chromatography. RF value about 0.

Compound 284 is converted to the base (92% of theory) by dissolving in 2 l of water at room temperature, filtering off a few insoluble components, alkalinizing the filtrate with 25% strength aqueous ammonia, filtering the colourless precipitate off by suction, washing with water and drying at 70° C. in vacuo.

EXAMPLE 285

37.7 g of the abovementioned base (0.1 mol), relative to the repeating structural unit of the high molecular weight compound) in 300 ml of dimethylformamide at 70°–75° C. are treated dropwise with 14 g of dimethyl sulphate and stirred for 6 hours at 70° C. After cooling to room temperature, the crystalline precipitate is filtered off by suction, washed with acetone and dried at 70° C. in vacuo. 48.5 g (96% of theory) of a high molecular weight compound with repeating structural units of the formula

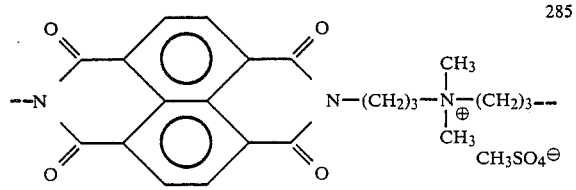

285 are obtained as a colourless, water-soluble, high-melting-point crystalline powder.

High molecular weight compounds with the following repeating structural units of the formula

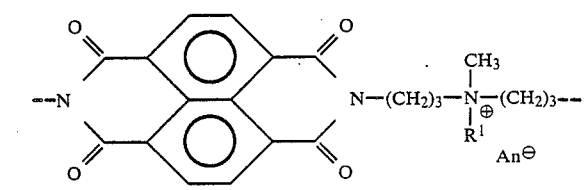

are prepared analogously to 285:

| Example | R¹ | An⊖ |
|---|---|---|
| 286 | ⟨phenyl⟩—CH₂— | Cl⊖ |
| 287 | benzimidazol-2-yl—CH₂— | Cl⊖ |
| 288 | CH₃OCO—CH₂— | Br⊖ |
| 289 | C₂H₅— | CH₃—⟨phenyl⟩—SO₃⊖ |
| 290 | n-C₄H₉— | Br⊖ |
| 291 | HO—CH₂—CH₂— | CH₃COO⊖ |
| 292 | Cl—⟨phenyl⟩—CH₂— | Cl⊖ |
| 293 | CH₂=CH—CH₂— | Br⊖ |
| 294 | ⟨phenyl⟩—CO—CH₂— | Cl⊖ |
| 295 | ⟨phenyl⟩—NH—CO—CH₂— | Cl⊖ |
| 296 | CH₃—CO—CH₂— | Br⊖ |
| 297 | NH₂—CO—CH₂— | Cl⊖ |
| 298 | NC—CH₂— | Cl⊖ |
| 299 | CH₂—CH—CH₂—<br>   \|   \|<br>  OH OH | CH₃COO⊖ |
| 300 | O₂N—⟨phenyl⟩—CH₂— | Cl⊖ |

EXAMPLE 301

42.7 g of N-phenyl-N'-(3-dimethylaminopropyl)-naphthalene-1,4,5,8-tetracarboxylic acid diimide (0.1 mol) and 18 g of 4,4'-bis-(chloroacetoamidophenyl)-methane (0.05 mol) are heated for 15 hours at 100° C. in 1 l of dimethylformamide and cooled. The crystalline precipitate is filtered off by suction, washed with isopropanol and dried at 60° C. in vacuo. 45 g (74% of theory) of compound of the formula

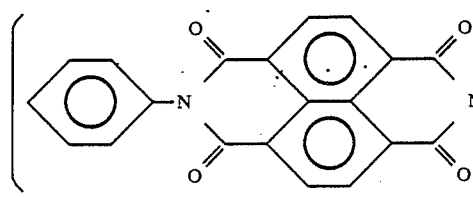 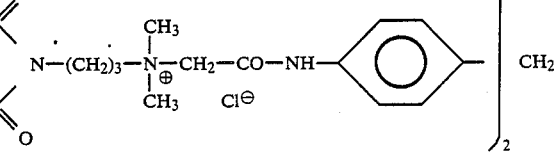 301 are obtained as a virtually colourless, high-melting-point, water-soluble crystalline powder. The compound is virtually pure according to thin-layer chromatography (silica gel, eluant as for compound 1). RF value: 0.14.

Preparation of the Starting Compounds

Naphthalene-1,4,5,8-tetracarboxylic acid monophenylimide 53.6 g of naphthalene-1,4,5,8-tetracarboxylic acid dianhydride (0.2 mol) or 60.8 g of naphthalene-1,4,5,8-tetracarboxylic acid (0.2 mol) are dissolved in 1 l of water at 90° C. with addition of 84 g of triethylamine (0.9 mol), treated with 18.6 g of aniline (0.2 mol) with stirring and adjusted to pH 6 by dropwise addition of about 20 ml of glacial acetic acid at 90° C. The mixture is stirred for about 8 hours at 90° C., the pH value being maintained between 7 and 6 by further dropwise addition of glacial acetic acid (6 ml in total). The mixture is cooled to room temperature, a few undissolved components are filtered off, and the filtrate is adjusted to pH 1 by dropwise addition of about 160 ml of concentrated hydrochloric acid. The crystalline precipitate is filtered off by suction, washed with water until the washings have pH 5, and dried at 70° C. in vacuo. 63 g (87% of theory) of naphthalene-1,4,5,8-tetracarboxylic acid monophenylimide are obtained as an almost colourless crystalline powder of melting point >300° C.

Naphthalene-1,4,5,8-tetracarboxylic acid N-phenyl-N'-(3-dimethylaminopropyl)-diimide 54.2 g of naphthalene-1,4,5,8-tetracarboxylic acid monophenylimide (0.15 mol) are suspended in 1.3 l of toluene, treated dropwise with 15.3 g of 1-amino-3-dimethylamino-propane (0.15 mol) with 1 g of glacial acetic acid with stirring and boiling on the water separator, boiled for a further 10 hours on the water separator and cooled. The crystalline precipitate is filtered off by suction, washed with toluene, recrystallized from 800 ml of boiling dimethylformamide, washed with ethanol and dried at 70° C. in vacuo. 54 g (84% of theory) of naphthalene-1,4,5,8-tetracarboxylic acid N-phenyl-N'-(3-dimethylaminopropyl)-diimide are obtained as a yellowish crystalline powder of melting point 270° C.

The following compounds are prepared analogously to 301:

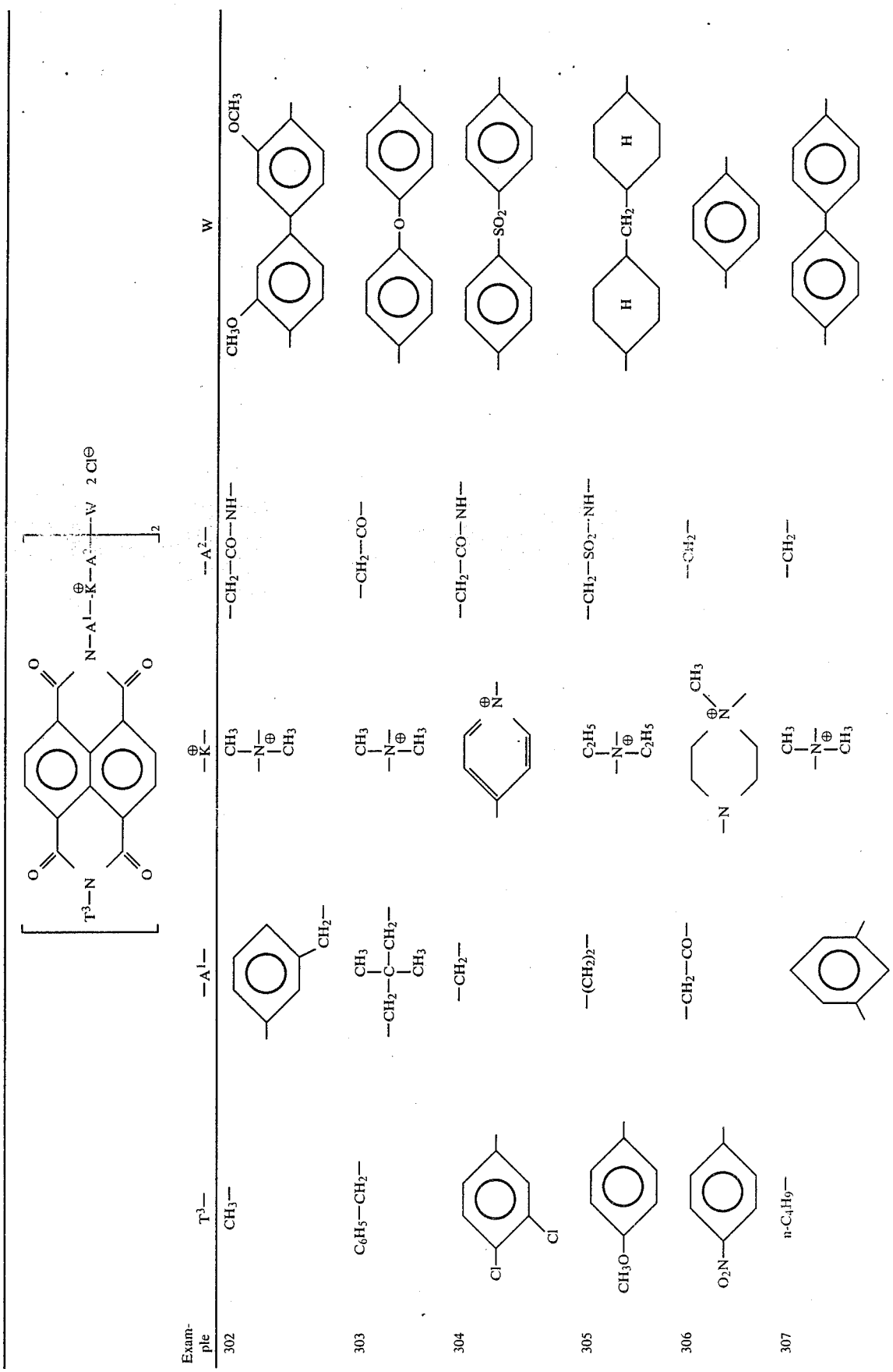

-continued
$$\left[ T^3-N \underset{O}{\overset{O}{\underset{\|}{\underset{\|}{\bigcirc\bigcirc}}}} N-A^1-\overset{\oplus}{K}-A^2-W \right]_2 \; 2Cl^{\ominus}$$
| Example | $T^3-$ | $-A^1-$ | $-\overset{\oplus}{K}-$ | $-A^2-$ | W |
|---|---|---|---|---|---|
| 308 |  | —NH—CO—CH$_2$— |  | —CH$_2$—CO—NH— | 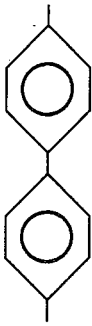 |
| 309 | H | 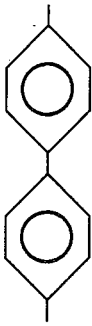 | 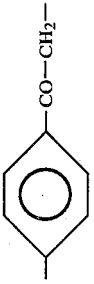 | —CH$_2$— | —CO— |
| 310 | 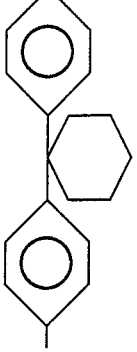 | —(CH$_2$)$_2$— | 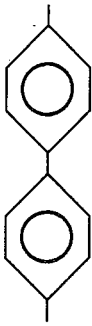 | —CH$_2$—CO—NH—CH$_2$— |  |
| 311 | HO—(CH$_2$)$_2$— | —(CH$_2$)$_3$—N(CH$_3$)—CO—CH$_2$— | 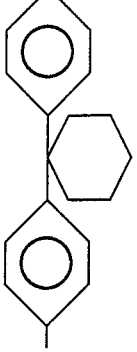 | —(CH$_2$)$_3$—NH—CO—NH— | 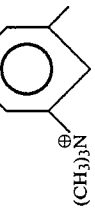 |
| 312 | 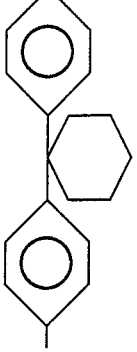 | — | 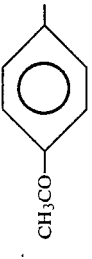 | —CH$_2$—CO—NH— | 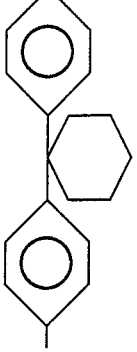 |

-continued
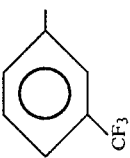
| Example | T³— | —A¹— | ⊕K | —A²— | W |
|---|---|---|---|---|---|
| 313 | 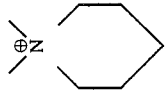 | 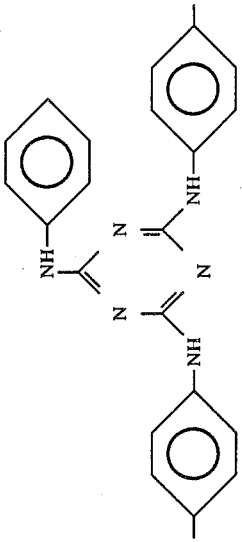 | 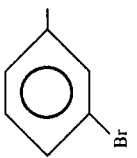 | —CH₂—CO—NH— | 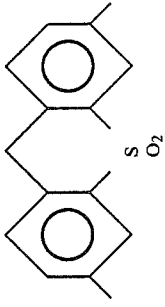 |
| 314 | 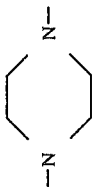 | —(CH₂)₃— | 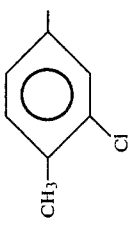 | —CH₂—CO—O— | 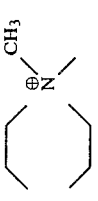 |
| 315 | | | | —CH₂—CO—NH— | |
| 316 | | | | —CH₂—CO— | |

-continued
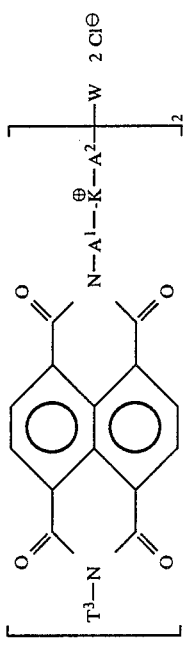
| Example | T³— | —A¹— | ⊕K⊕ | —A²— | W |
|---|---|---|---|---|---|
| 317 | CH₃—SO₂—⌬— | —CH₂— |  | —A²— | 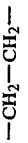 |
| 318 | CH₃O—⌬— | — | 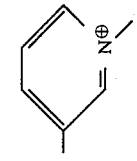 | —CH₂—CO—NH— | —CH₂—CH₂— |
| 319 | C₂H₅O—⌬— | — | 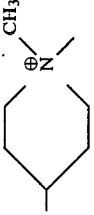 | —CH₂—CO—NH— | — |
| 320 | CH₃CO—NH— | —NH—CO—CH₂— |  | —CH₂— | —CO— |
| 321 | CH₃O— | —CH(CH₃)—(CH₂)₃— |  | —CH₂— | 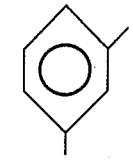 |

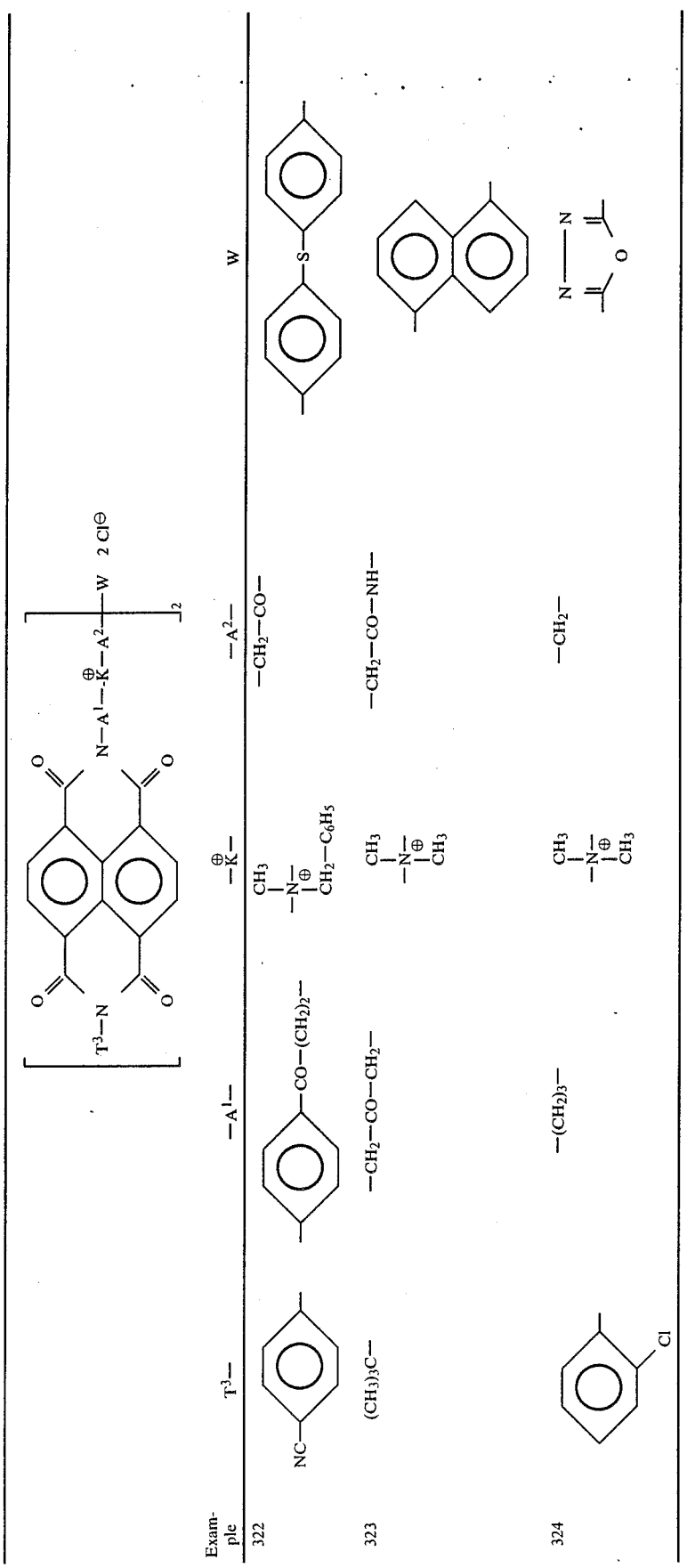

High molecular weight compounds with the repeating structural units 325–329 are also prepared analogously to 301 from the educts 325E–329E:

| Example | Educt |
|---|---|
| 325E | Cl—CH₂—CO—NH—N⟨naphthalenetetracarboxydiimide⟩N—(CH₂)₃—N(CH₃)₂ |
| 326E | Br—CH₂—CO—⟨C₆H₄⟩—N⟨naphthalenetetracarboxydiimide⟩N—⟨C₆H₄⟩—CH₂—N(CH₃)₂ |
| 327E | Br—CH₂—CO—CH₂—N⟨naphthalenetetracarboxydiimide⟩N—CH₂—⟨4-pyridyl⟩ |
| 328E | Cl—CH₂—CO—N(CH₃)—(CH₂)₃—N⟨naphthalenetetracarboxydiimide⟩N—CH₂—C(CH₃)₂—CH₂—N(CH₃)₂ |
| 329E | Cl—CH₂—CO—NH—⟨C₆H₄⟩—N⟨naphthalenetetracarboxydiimide⟩N—CH₂—CO—N⟨piperazine⟩N—CH₃ |
| 325 | —(CH₂)₃—N⁺(CH₃)₂—CH₂—CO—NH—N⟨naphthalenetetracarboxydiimide⟩N— , Cl⁻ |
| 326 | —⟨C₆H₄⟩—CH₂—N⁺(CH₃)₂—CH₂—CO—⟨C₆H₄⟩—N⟨naphthalenetetracarboxydiimide⟩N— , Br⁻ |

| Example | Educt |
|---|---|
| 327 | 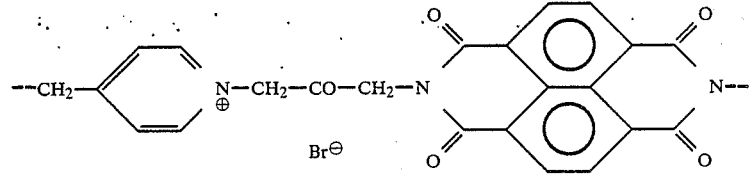 |
| 328 | 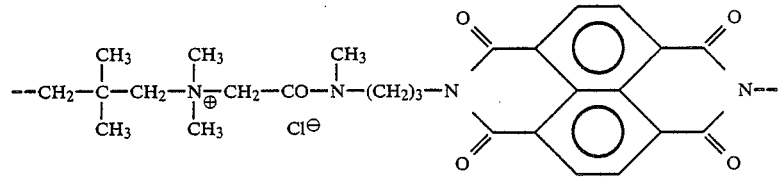 |
| 329 | 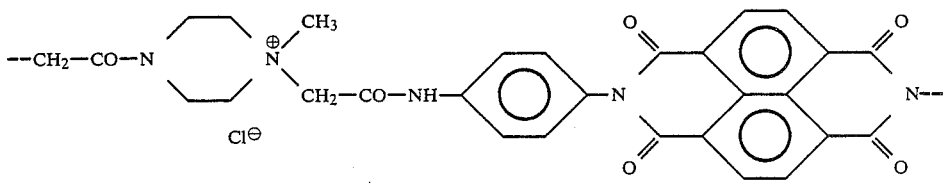 |

EXAMPLE 330

41.8 g of naphthalene-1,4,5,8-tetracarboxylic acid N-(4-ω-dimethylaminobenzyl)-monoimide (0.1 mol), prepared analogously to the monophenylimide described in Example 301, are suspended in 600 ml of toluene and treated with 1 g of glacial acetic acid. 10.2 g of 1-amino-3-dimethylamino-propane (0.1 mol) are then added dropwise with stirring and boiling on the water separator and the mixture is allowed to boil for a further 7 hours on the water separator, cleared while hot with 2 g of Tonsil and filtered, and the filtrate is evaporated to dryness on the rotary evaporator. A residue of 43 g (about 89% of theory) of naphthalene-1,4,5,8-tetracarboxylic acid N-(4-ω-dimethylaminobenzyl)-N'-(3-dimethylaminopropyl)-diimide is obtained as a yellow crystalline powder with melting point 90° C.; m/e=484 (M⊕).

29 g of this compound (0.06 mol) and 13 g of amidosulphonic acid (about 0.13 mol) are refluxed for 5 hours in 400 ml of acetone and cooled. 40 g (about 99% of theory) of compound of the formula

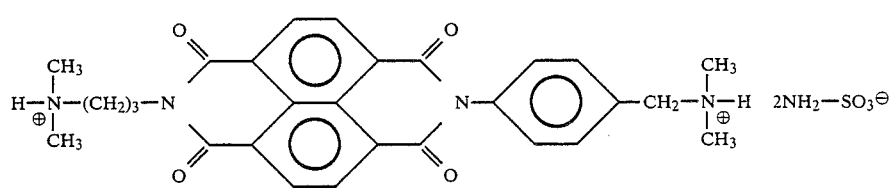

330 are obtained in the form of colourless, water-soluble crystals.

The following compounds are prepared analogously to Example 330 (basic precursor) and Example 193 (quaternization reaction):

| Example | ⊕E— | —A³— | ⊕E—A³—N   N—A¹—(E)'  2 An⊖ (naphthalene diimide core) | —A¹— | ⊕(E)' | An⊖ |
|---|---|---|---|---|---|---|
| 331 | CH₃–N⊕(CH₃)(CH₃)–CH₂–C₆H₄– | —(CH₂)₃— | | —C₆H₄–CH₂— | —CH₂–N⊕(CH₃)(CH₃)(CH₃) (on C₆H₄–Cl) | Cl⊖ |
| 332 | CH₃–N⊕(CH₃)(CH₃)–CH₂–CO–C₆H₄– | —CH₂–C(CH₃)₂–CH₂— | | —CH₂— | C₆H₅–N⊕(pyridinium with –CH₂–CO–NH–) toluene ring | Br⊖ |
| 333 | benzimidazol-2-yl–CH₂–N⊕(C₂H₅)(C₂H₅)– | —(CH₂)₂— | | —C₆H₄–CO— | benzimidazole–CH₂–N⊕(CH₃)(piperidine) on toluene | Cl⊖ |
| 334 | H₂N–CO–CH₂–N⊕(pyridinium, p-tolyl) | —CH₂— | | —(CH₂)₂— | CH₂–CO–NH₂, CH₃–N⊕(morpholine) | Cl⊖ |
| 335 | (CH₃)₃N⊕— | xylyl (dimethylphenyl) | | —C₆H₄–CO–CH₂— | —N⊕(CH₃)₃ | CH₃SO₄⊖ |

-continued

| Example | ⊕E— | —A³— | —A¹— | ⊕(E)'— | Anᐩ |
|---|---|---|---|---|---|
| 336 | (structure: E—A³—N(C=O)₂-naphthalene-(C=O)₂N—A¹—(E)' 2 An⊖ with ⊕E— = Cl-C₆H₄-NH-CO-CH₂-N⁺(CH₃)₂-CH₃) | —(CH₂)₃— | phenyl (—C₆H₄—) | imidazolium N-CH₂-CO-NH-C₆H₄-Cl | Cl⊖ |
| 337 | CH₂=CH-CH₂-N⁺(pyridinium with CH₃) | —CH₂— | —CH₂—CO—CH₂— | —N⁺(CH₃)(CH₂—CH=CH₂)(CH₂CH₂OH) | Br⊖ |
| 338 | cyclohexyl-N⁺(CH₃)₂ (H on ring) | —(CH₂)₃— | —CH₂—C₆H₄—CH₂— | cyclohexyl-N⁺(CH₃)₃ (H on ring) | Br⊖ |

The high molecular weight compounds with the following repeating structural units are prepared analogously to Example 330 (basic precursor) and Example 261 (bisquaternization):

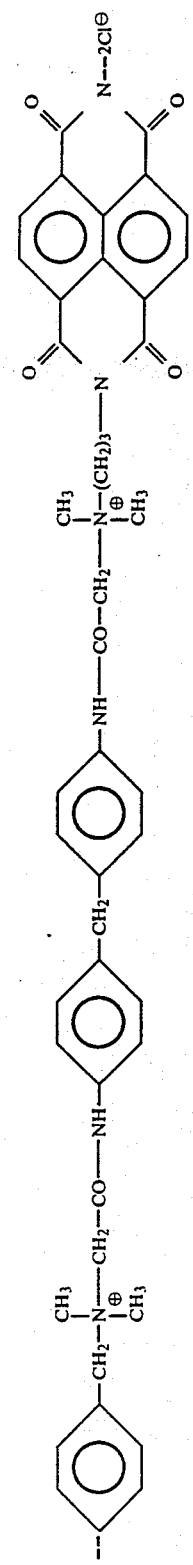
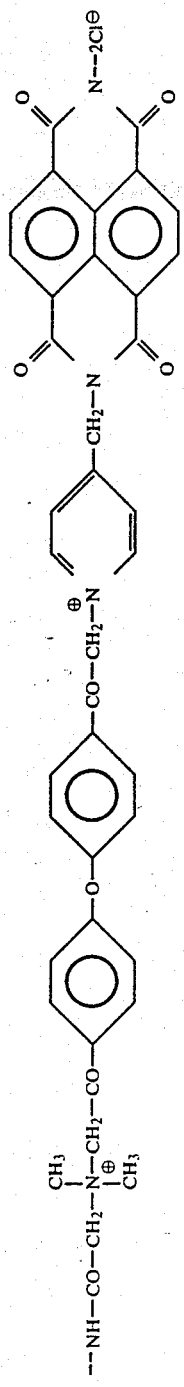
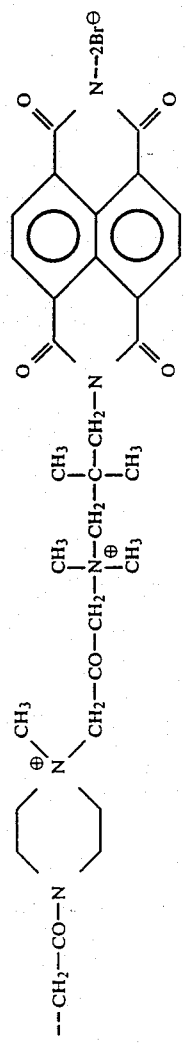

EXAMPLE 342

Naphthalene-1,4,5,8-tetracarboxylic acid is reacted with 1 equivalent of 1-amino-(b 3-diethylamino-propane and analogously to Example 301, and the monoimide obtained is subsequently condensed with 1,2-diaminoethane in the molar ratio 2:1 and converted to the amidosulphonate of the following formula:

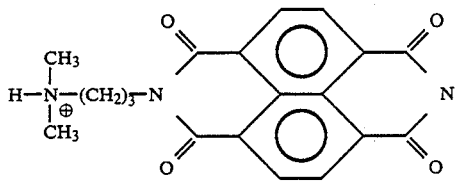

using amidosulphonic acid.

Colourless water-soluble crystals.

The reaction sequence above is repeated, but, in place of 1,2-diaminoethane, an equivalent amount of

| (a) p-phenylenediamine | (Example 343) |
| (b) 1,3-diaminocyclohexane | (Example 344) |
| (c) 4,4'-diaminodiphenylmethane | (Example 345) | is used.

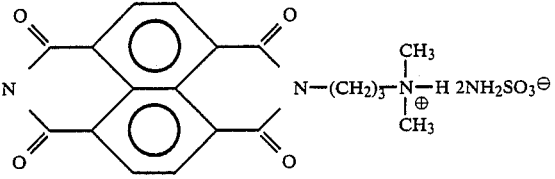

342

The reaction sequence above is repeated again, but, in place of 1,2-diaminoethane, an equivalent amount of bis-(3-aminopropyl)-methylamine is used this time and the reaction product subsequently reacted with 3 equivalents of amidosulphonic acid. The compound of the formula

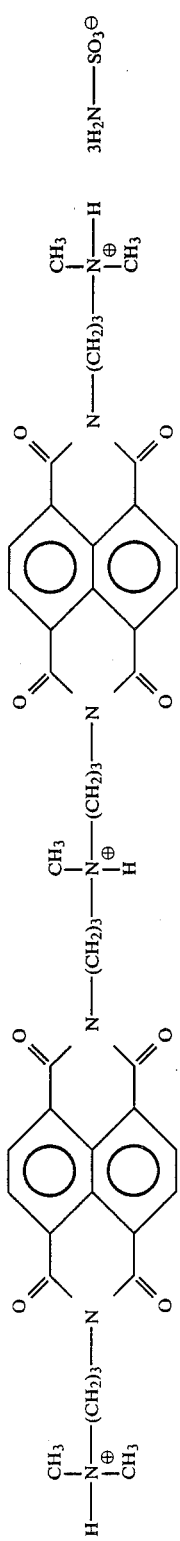

is obtained. Colourless water-soluble crystals.

EXAMPLE 347

Compound 342, in the form of the free base, is quaternized, analogously to Example 193, with 2 equivalents of 4-chlorobenzyl chloride. The compound of the formula

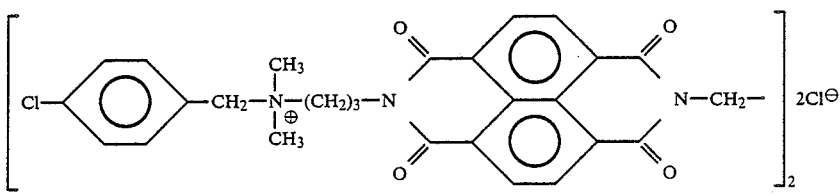

is obtained as colourless water-soluble crystals.

EXAMPLE 348

Naphthalene-1,4,5,8-tetracarboxylic acid monophenylimide, the preparation of which is described in Example 301, is condensed with triethylenetetramine in the molar ratio 2:1 analogously to Example 176 and the base obtained is subsequently quaternized with 2 equivalents of dimethyl sulphate analogously to Example 158. The compound of the formula

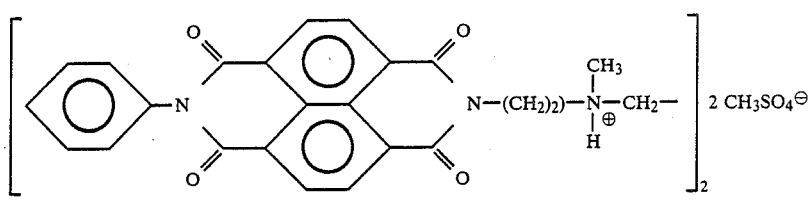

is obtained in the form of almost colourless, water-soluble crystals.

EXAMPLE 349

Compound of the formula 342, in the form of the free base, is bisquaternized in boiling acetonitrile with an equivalent amount of 4,4'-bis-(chloroacetamidophenyl)-methane analogously to Example 261. The high molecular weight compound with the repeating structural unit of the formula 349
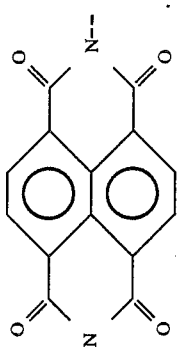
|
N—(CH₂)₂—N
|
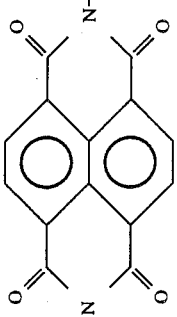
|
N—(CH₂)₃—N⁺(CH₃)(CH₃)—CH₂—CO—NH
|
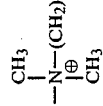
|
CH₂
|
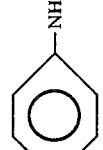
|
NH—CO—CH₂—N⁺(CH₃)(CH₃)—(CH₂)₃⟶ is obtained as colourless crystals which are soluble in hot water.

EXAMPLE 350

The compound of the formula 346, in the form of the free base, is trisquaternized with the three-fold amount of dimethyl sulphate analogously to Example 285. The compound of the formula

EXAMPLE 359

Naphthalene-1,4,5,8-tetracarboxylic acid is initially reacted with 1 equivalent of 1-amino-3-dimethylaminopropane analogously to Example 301, the monoimide obtained is subsequently condensed with triethylenetetramine in the molar ratio 2:1 and the colourless, high-melting-point water-insoluble condensation product

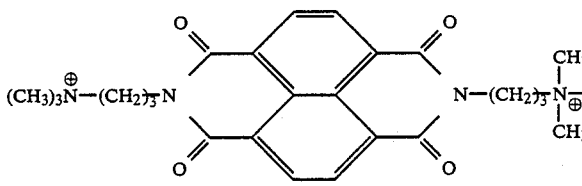

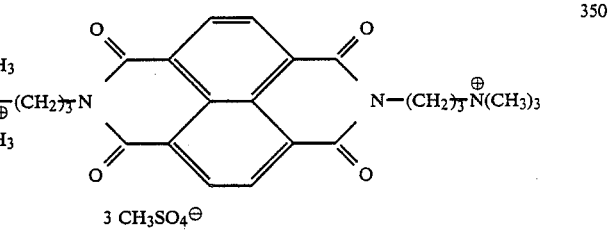

350 is obtained as almost colourless, water-soluble crystalline powder.

In an analogous fashion, but at the somewhat higher reaction temperatures specified, the following compounds are obtained:

obtained is finally reacted with 7 (theoretically 6) equivalents of dimethyl sulphate analogously to Example 285, but with addition of 2.5 equivalents of triisopropanolamine as proton scavenger. The compound of the formula

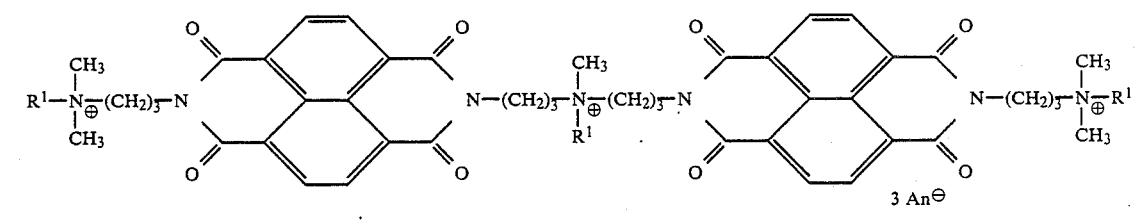

| Example | $R^1$ | $An^\ominus$ | Reaction temperature |
|---|---|---|---|
| 351 | $C_2H_5-$ | $C_2H_5SO_4^\ominus$ | 80–85° C. |
| 352 | $C_6H_5-CH_2-$ | $Cl^\ominus$ | 110–120° C. |
| 353 | $n-C_4H_9-$ | $Br^\ominus$ | 140–145° C. |
| 354 | $C_6H_5-CO-CH_2-$ | $Cl^\ominus$ | 90–100° C. |
| 355 | $C_6H_5-NH-CO-CH_2-$ | $Cl^\ominus$ | 100° C. |
| 356 | $H_2N-CO-CH_2-$ | $Cl^\ominus$ | 100° C. |
| 357 | $CH_3OCO-CH_2-$ | $Br^\ominus$ | 110° C. |
| 358 | benzimidazol-2-yl-$CH_2-$ | $Cl^\ominus$ | 110° C. |

359
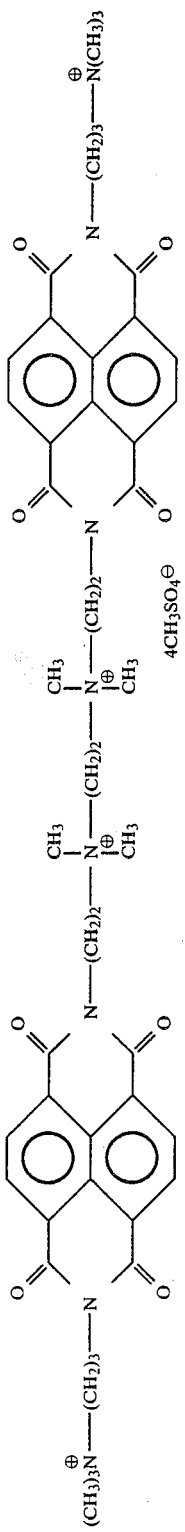

is obtained as colourless, easily water-soluble crystalline powder.

APPLICATION EXAMPLE A 5000 parts of paper pulp from bleached sulphite cellulose with a degree of beating of 40° Schopper-Riegler and a dry component content of 2% (corresponding to 100 parts of sulphite cellulose) are adjusted to pH 7.5 using sodium hydroxide solution with stirring, treated with a solution of 0.2 part of the optical brightener of the formula

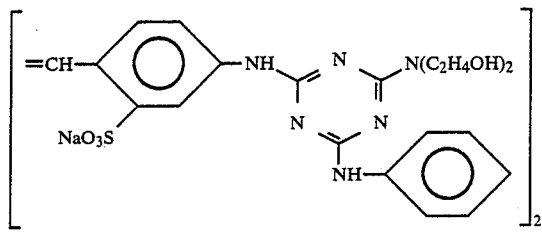

in 100 parts of water and stirred for 5 minutes. Subsequently, 100 parts of an aqueous solution containing 1.0 parts of the 20% strength solution of the fluorescence quencher of formula 1 described in Preparation Example 1 is added, the mixture stirred for 1 minute and the paper sheet formed. After drying, a paper is obtained which hardly differs from the non-brightened paper.

In contrast, if the same amount of a fluorescence quencher prepared according to DE-A, 1,912,647, Example A or B, or DE-A 2,448,293, Preparation Example 1, is used, a paper is obtained with clearly perceptible brightness.

If the comparison experiments are repeated in the region of pH 9, the difference is even larger.

APPLICATION EXAMPLE B 5000 parts of paper pulp from bleached sulphite cellulose with a degree of beating of 40° Schopper-Riegler and a dry component content of 2% are stirred for several minutes with 3 parts of crystallized aluminum sulphate and treated with a solution of 0.1 part of the optical brightener of the formula

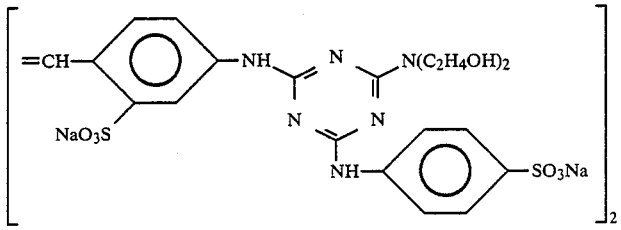

in 100 parts of water. After 15 minutes, 2 parts of size milk are added. After mixing thoroughly, the pH is adjusted to 4.5 using sulphuric acid. 100 parts of an aqueous solution containing 1.0 part of the 20% strength solution of the fluorescence quencher of the formula 1 described in Example 1 are now added, the mixture is stirred for 1 minute and diluted to 20,000 parts using water, and the paper sheet is formed. After drying, a sized paper is obtained which hardly differs from non-brightened paper.

Similarly strong fluorescence quenching effects are obtained when one of the fluorescence quenchers described in the other preparation examples is used.

APPLICATION EXAMPLE C

Paper with a weight of 80 g/m$^2$ is produced on a Fourdrinier machine using brightened scrap paper as raw material.

To quench the fluorescence of the optical brightener contained in this, the paper web is sprayed in the second half of the wet end with a diluted aqueous solution of the compounds described in Preparation Example 1 in such a way that the dry paper contains 0.02 to 0.1% (depending on the concentration of the brightener in the raw material) of fluorescence quencher.

The paper thus manufactured corresponds, in the optical properties, to a paper quality which does not contain optical brightener.

The fluorescence quenchers described in the remaining preparation examples are employed with the same success.

APPLICATION EXAMPLE D 10 g of bleached nettle cotton fabric is treated for 30 minutes at 50° C. with a solution of 0.1% BLANKOPHOR ® BA 267% in the float ratio 1:20. After rinsing and drying, a Berger whiteness of 150 is measured (base white about 80).

The fabric whitened in this fashion is subsequently treated for 30 minutes at 50° C. with 0.1% of the fluorescence quencher described in Preparation Example 1 in the float ratio 1:20. After rinsing and drying, the Berger whiteness is again determined. It is in the region of 100. Visually, only a slight brightening effect is still perceptible.

Other compounds described in the preparation examples can also be employed with similar success.

APPLICATION EXAMPLE E

The possibility of neutralizing undesired residues of aqueous solutions of anionic whiteners in dyeing equipment, dyeing machines, storage vessels and supply lines by using fluorescence quenchers of Examples 1 to 359 may be demonstrated by means of the following quantitative model experiment:

(a) 0.03 mmol of an optical brightener of the formula

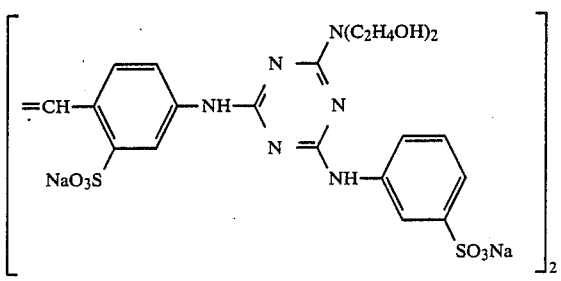

(42.2 mg of 86.5% strength = 36.5 mg of 100% strength) are dissolved in 100 ml of water.

(b) 0.1 mmol of fluorescence quencher of the formula 1 (91.5 mg) are dissolved in 100 ml of water.

(c) 5 ml of the solution prepared under (a) are made up to 100 ml.

(d) 5 ml of the solution prepared under (a) and x ml of that prepared under (b) are mixed and made up to 100 ml (x = 1, 2, 3, 4).

The intensity of the fluorescence emission of the following solutions is measured at 436 nm in sequence in a Zeiss DMR 21 spectrophotometer with 1 ml quartz cell and ZF M4 supplementary fluorescence instrument (450 W xenon lamp) with fluorescence excitation using UV light of 345 nm:

| | |
|---|---|
| Solution (c) ($1.5 \cdot 10^{-5}$ mol/l brightener) | 100% fluorescence intensity |
| Solution (d), x = 1 ($10^{-5}$ mol/l) | 61% fluorescence intensity |
| Solution (d), x = 2 ($2.0 \cdot 10^{-5}$ mol/l) | 27% fluorescence intensity |
| Solution (d), x = 3 ($3.0 \cdot 10^{-5}$ mol/l) | 3% fluorescence intensity |
| Solution (d), x = 4 ($4.0 \cdot 10^{-5}$ mol/l) | 0% fluorescence intensity |

The experiment shows that fluorescence quenchers, in dilute aqueous solution at room temperature, neutralize the abovementioned optical brightener to a large extent at a molar ratio of 2:1, and completely at a molar ratio of 2.7:1.

If, in place of compound 1, one of the compounds described in DE-A 1,912,647 or 2,448,293 is employed, complete quenching of fluorescence is not achieved, even when the concentration of the quencher applied are even higher.

I claim:

1. A process for the quenching of the fluorescence created by anionic optical brighteners said process comprising adding a substrate containing said optical brighteners virtually colorless, water-soluble, cationic compounds, wherein said compounds contain at least one cationic group per molecule and at least two naphthalene-peri-dicarboxylic acid imide groups which are nitro group free per molecule.

2. A process according to claim 1 wherein the compounds have the formula

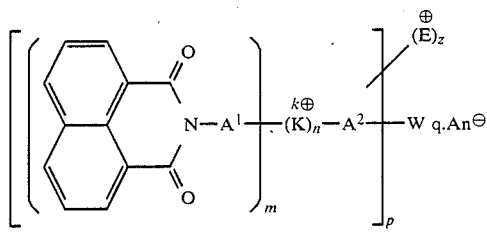

in which

A$^1$, A$^2$ and W represent a bridging member or a single bond,

W also represents hydrogen,

E$^\oplus$ represents a terminal ammonium or sulphonium group,

K$^\oplus$ represents a doubly bridging ammonium or sulphonium group,

An$^\ominus$ represents an anion, m and k represent 1 or 2, z represents 0, 1, 2, 3 or 4, n represents 0 or 1 and p represents 1, 2 or 3, q corresponds to the sum of the free cationic charges, where $n + z \neq 0$, in which the naphthalene ring can also be substituted in the second peri-position by —CH$_2$—CH$_2$—, —CO—O—CO— or —CO—NH—CO—, the naphthalene ring system, A$^1$, A$^2$, W, -E$^\oplus$ and -K$^\oplus$- and the second peridicarboxlic acid imide nitrogen atom can be substituted by non-ionic radicals.

3. A process according to claim 2, wherein the compounds have the formula

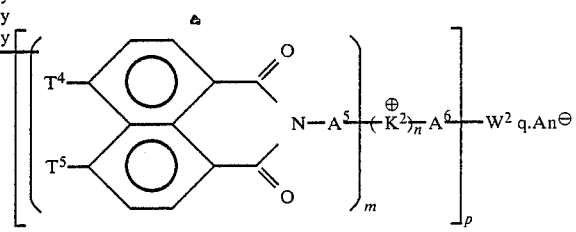

in which

T$^4$ and T$^5$ together represent a —CO—N(T$^6$)—CO— group,

T$^6$ represents hydrogen, OH, C$_1$-C$_6$-alkyl which is optionally substituted by 1 to 2 OH groups, chlorine, C$_1$-C$_4$-alkoxy or COOH, allyl, phenyl or benzyl which can be substituted by 1 or 2 C$_1$-C$_4$-alkyl, chlorine, C$_1$-C$_2$-alkoxy, bromine, carboxy, cyano, C$_1$-C$_2$-alkoxycarbonyl, C$_1$-C$_2$-alkylsulphonyl, carbamoyl or sulphamoyl, β-aminoethylphenyl, pyridyl-(2)-or-(3)-, benzothiazol-(2)-yl, 1,2,4-triazol-3-yl, cyclohexyl, -A$^5$-E$^2\oplus$ or, in the case where m = 1, n = 0 and p = 1, represents a grouping of the formula -A$^5$-K$^2\oplus$-A$^6$- or -A$^5$-K$^2\oplus$-A$^6$-W$^2$-A$^6$-K$^2\oplus$-A$^5$-

A$^5$ and A$^6$ or the two radicals A$^5$ being bonded to 2 different 1,4,5,8-naphthalene tetracarboxylic acid diimide molecules, A$^5$ represents a single bond, C$_1$-C$_5$-alkylene, m- or p-C$_6$H$_4$-CH$_2$-, A$^6$ represents a single bond, —CH$_2$—, —CH$_2$—CO—O—, —CH$_2$—CO—N(R)—, —CH$_2$—SO$_2$—N(R)—, —(CH$_2$)$_2$—CO—N(R)—, —CH$_2$—CO—NH—CH$_2$—, C$_1$-C$_5$-alkylene—N(R)—CO—, C$_1$-C$_5$-alkylene-N(R)—SO$_2$—, C$_1$-C$_5$-alkylene—N(R)—CO—NH—, —CH$_2$—C$_6$H$_4$—NH—CO—, —CH$_2$—C$_6$H$_4$—NH—SO$_2$—, —CH- 2—C₆H₄—NH—CO—NH—, —(CH₂)$_w$—CO—,
—(CH₂)$_w$—CO—C₆H₄—NH—CO—, —(CH₂)$_w$—CO—C₆H₄—NH—SO₂—, —(CH₂)$_w$—CO—C₆H₄—NH—CO—NH—, in addition: —SO₂—, —CO— or —CONH—, when K²⊕=piperazinium, and —NH—CO—NH—, when K²⊕=pyridinium, K²⊕ represents

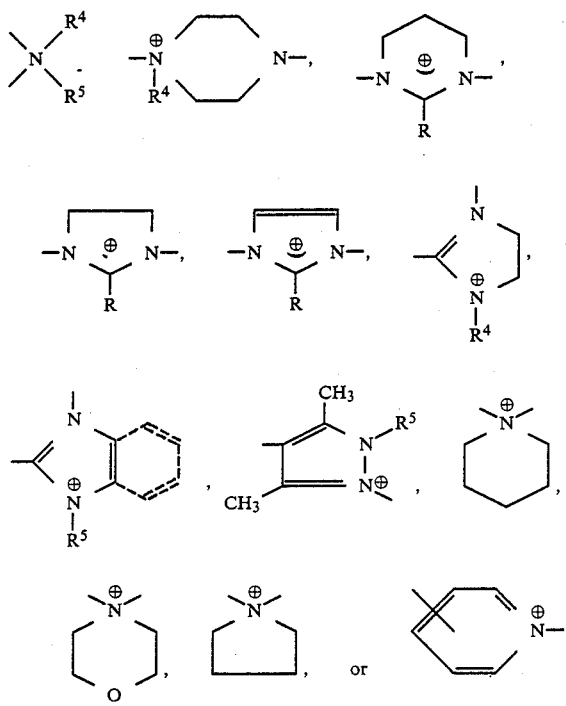

-E²⊕ represents

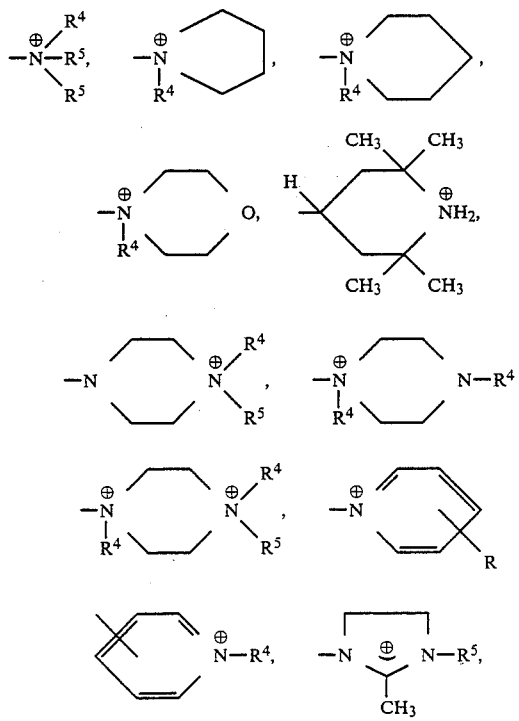

-continued

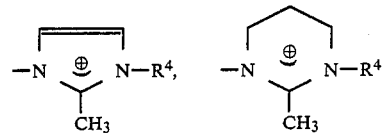

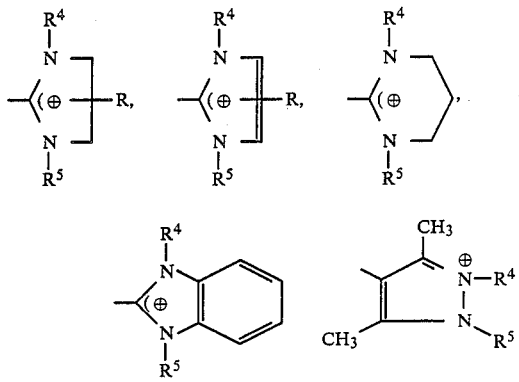

R⁴ and R⁵ each represent C₁–C₄-alkyl, which can be substituted by OH, CONH₂, C₁–C₂-alkoxycarbonyl or C₁–C₂-alkylcarbonyl, or allyl, R⁴, in addition, represents hydrogen, cyclohexyl, benzoyl- or benzoylmethyl radicals, which can be substituted on the nucleus by 1 or 2 radicals from the series comprising methyl, chlorine, methoxy, ethoxy, cyano, C₁–C₂-alkoxycarbonyl or nitro, or benzimidazol-2-ylmethyl, R⁵, in addition, represents benzyl or one radical R⁵ in each case also represents phenyl, W² represents —CO—, a p-bonded benzene, naphthalene, cyclohexane, piperazine, thiophene-(2,5)-, 1,3,4-oxadiazole-(2,5)-, s-triazine,-(2,4 or 2,4,6) radical or a radical of the formulae

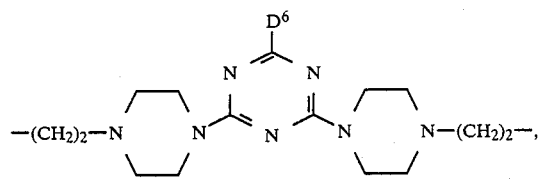

or

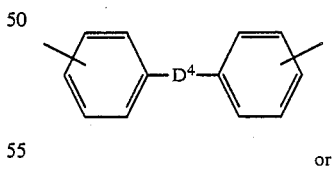

in which, in the case where p=1, one of the specified free valences is saturated by hydrogen, D⁴ and D⁵ each represent CH₂, a C₂–C₅-alkylene which is optionally interrupted by —O—, —O—, —N(R)—, —O—C₂–C₄-alkylene—O— or a radical of the formula

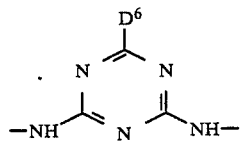

where
$D^6 = Cl$, $OR$, $-N(R^4R^5)$,

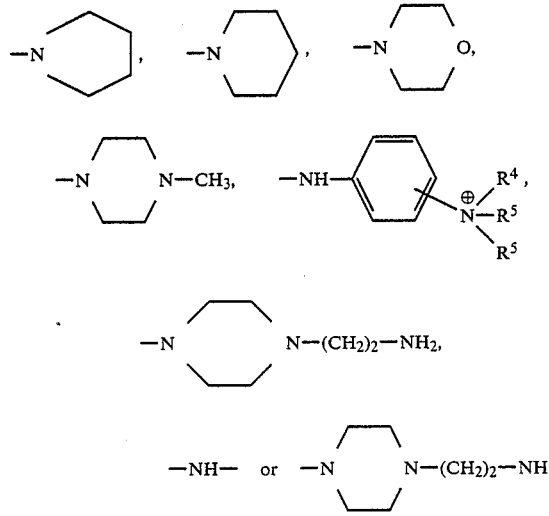

$D^4$, in addition, represents 1,1-cyclohexylene, p-phenylene, $-CH(C_6H_5)-$, $-CH(C_6H_4-)-$, $-S-$, $-SO_2-$, $-CO-NH-$, $-NH-CO-NH-$, $$-O-PO-O-$$
$$\overset{|}{O-}$$

or a single bond, it being possible for the rings mention in $D^4$, $D^5$, and also in $W^2$, to be substituted by $CH_3$, $CH_3O$ or $Cl$, in which, in the case where $p=2$, the grouping $-K^2\oplus-A^6-W^2-A^6-K^2\oplus-$ as a whole can also represent

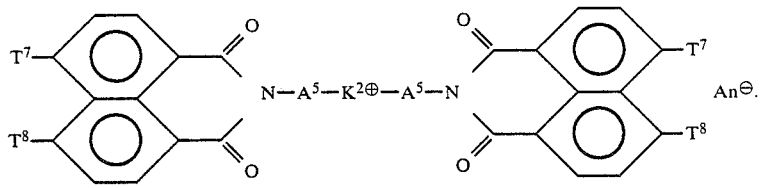

in which the indices m and p only denote 1 simultaneously when $T^4$ and $T^5$ form a cyclic peridicarboxylic acid imide grouping, and in which n can only be zero when $T^6$ contains a cationic group $-K^2\oplus-$ or $-E^2\oplus$.

4. A process according to claim 3, wherein the compounds have the formula $$\left[\left(\begin{array}{c}T^7\\T^8\end{array}\bigcirc\bigcirc\begin{array}{c}\overset{O}{\diagdown}\\\overset{O}{\diagup}\end{array}N-A^5\right)_m K^2\oplus-A^6\right]_r W^2\, r'An^\ominus$$

with
$T^7$ $T^8$ = hydrogen, chlorine or bromine,
$r = 2$ or $3$,
in which the radicals $A^6$ and —when $m=2$—the radicals $A^5$ can be different from one another.

5. A process according to claim 4, wherein the compounds correspond to the formula $$T^7\bigcirc\bigcirc\begin{array}{c}\overset{O}{\diagdown}\\\overset{O}{\diagup}\end{array}N-A^5-K^2\oplus-A^5-N\begin{array}{c}\overset{O}{\diagdown}\\\overset{O}{\diagup}\end{array}\bigcirc\bigcirc T^7 \quad An^\ominus.$$

* * * * *

UNITED STATES PATENT AND TRADEMARK OFFICE
CERTIFICATE OF CORRECTION

PATENT NO. : 4,919,848

DATED : April 24, 1990

INVENTOR(S) : Horst Harnisch

Page 1 of 6

It is certified that error appears in the above-identified patent and that said Letters Patent is hereby corrected as shown below:

Col. 4, line 28    Delete " 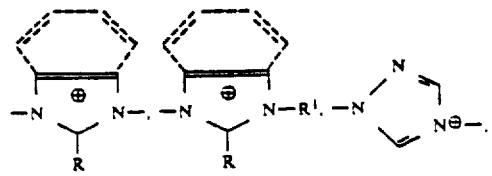 " and substitute -- 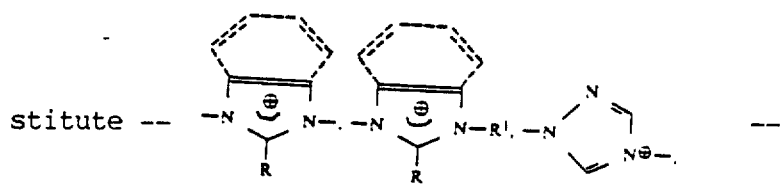 --

Signed and Sealed this

Fourth Day of January, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 4,919,848

DATED : April 24, 1990

INVENTOR(S) : Horst Harnisch

It is certified that error appears in the above-identified patent and that said Letters Patent is hereby corrected as shown below:

Col. 19, line 15    Delete " 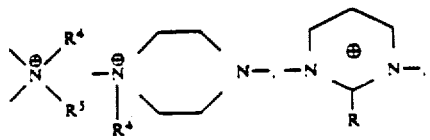 " and substitute

-- 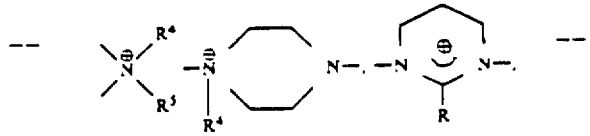 --

Col. 19, line 23    Delete " 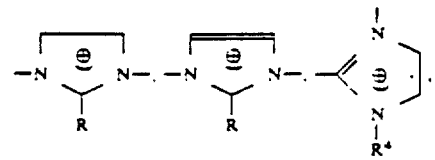 " and substitute

-- 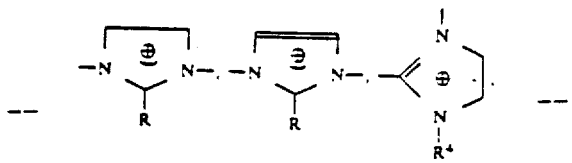 --

Col. 20, line 6    Delete " 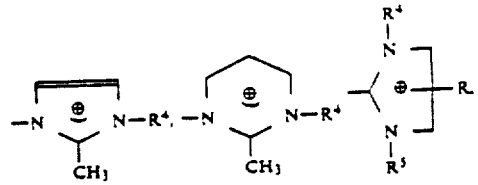 " and substitute

UNITED STATES PATENT AND TRADEMARK OFFICE
CERTIFICATE OF CORRECTION

PATENT NO. : 4,919,848

DATED : April 24, 1990

INVENTOR(S) : Horst Harnisch

Page 3 of 6

It is certified that error appears in the above-identified patent and that said Letters Patent is hereby corrected as shown below:

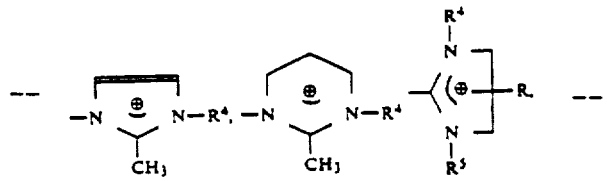

Col. 20, line 14  Delete " 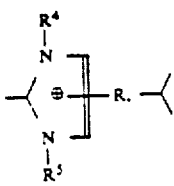 " and substitute

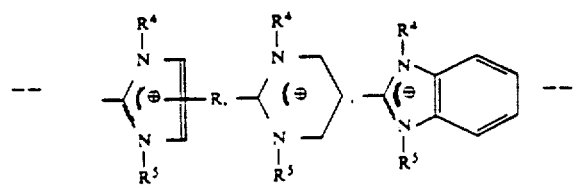

Col. 43, Ex 29  Under "⊕" delete " 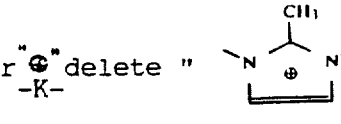 " and substitute -- 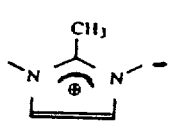 --
-K-

UNITED STATES PATENT AND TRADEMARK OFFICE
CERTIFICATE OF CORRECTION

PATENT NO. : 4,919,848

DATED : April 24, 1990

INVENTOR(S) : Horst Harnisch

It is certified that error appears in the above-identified patent and that said Letters Patent is hereby corrected as shown below:

Col. 72, Ex 146 Under "⊕" delete " 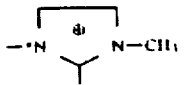 " and substitute --  --
-K-

Col. 73, Ex 147 Under "⊕" delete " 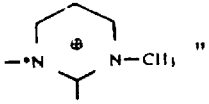 " and substitute -- 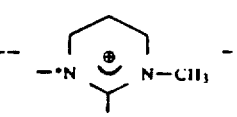 --
-K-

Col. 81, Ex 177 Delete " 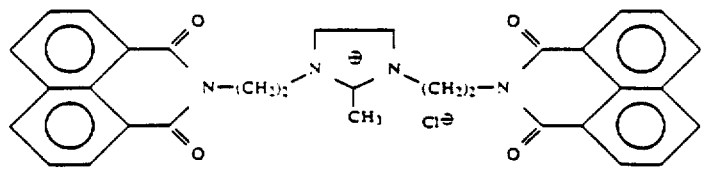 "

and substitute --

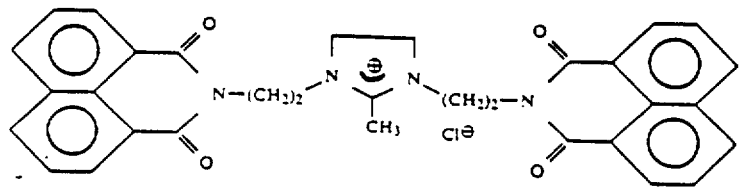 --

UNITED STATES PATENT AND TRADEMARK OFFICE
CERTIFICATE OF CORRECTION

PATENT NO. : 4,919,848

DATED : April 24, 1990

INVENTOR(S) : Horst Harnisch

It is certified that error appears in the above-identified patent and that said Letters Patent is hereby corrected as shown below:

Col. 108, Ex 281 Under " ⊕ " delete " 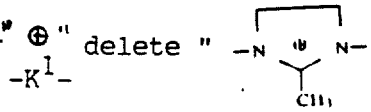 " and substitute $-K^1-$

-- 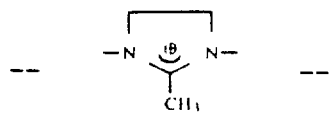 --

Col. 153, line 20 Delete " 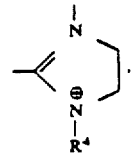 " and substitute -- 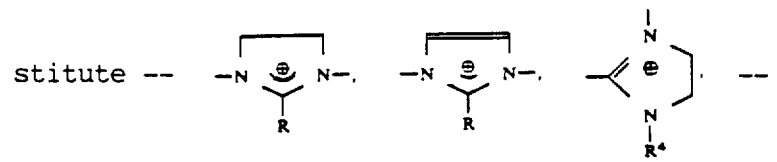 --

UNITED STATES PATENT AND TRADEMARK OFFICE
CERTIFICATE OF CORRECTION

PATENT NO. : 4,919,848

DATED : April 24, 1990

INVENTOR(S) : Horst Harnisch

It is certified that error appears in the above-identified patent and that said Letters Patent is hereby corrected as shown below:

Col. 154, lines 28- Delete " benzoyl " and substitute -- benzyl --

Col. 156, line 34  After " $T^7$ " insert -- and --